United States Patent
Yeo et al.

(10) Patent No.: US 9,962,401 B2
(45) Date of Patent: *May 8, 2018

(54) CHITOSAN DERIVATIVES FOR INACTIVATION OF ENDOTOXINS AND SURFACE PROTECTION OF NANOPARTICLES

(71) Applicant: Purdue Research Foundation, West Lafayette, IN (US)

(72) Inventors: Yoon Yeo, West Lafayette, IN (US); Gaurav Bajaj, West Lafayette, IN (US); Peisheng Xu, Lafayette, IN (US); Karen Liu, Lafayette, IN (US); Eun Jung Cho, West Lafayette, IN (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/345,870

(22) Filed: Nov. 8, 2016

(65) Prior Publication Data
US 2017/0143755 A1    May 25, 2017

Related U.S. Application Data

(63) Continuation-in-part of application No. 15/212,771, filed on Jul. 18, 2016, now Pat. No. 9,517,246, which is a continuation of application No. 13/628,991, filed on Sep. 27, 2012, now Pat. No. 9,393,262.

(60) Provisional application No. 61/539,557, filed on Sep. 27, 2011.

(51) Int. Cl.
| | |
|---|---|
| *A61K 31/722* | (2006.01) |
| *C08L 5/08* | (2006.01) |
| *C08B 37/08* | (2006.01) |
| *C08J 3/16* | (2006.01) |
| *C08L 79/02* | (2006.01) |
| *C08L 101/00* | (2006.01) |
| *A61K 9/00* | (2006.01) |
| *A61K 9/19* | (2006.01) |

(52) U.S. Cl.
CPC .......... *A61K 31/722* (2013.01); *A61K 9/0019* (2013.01); *A61K 9/19* (2013.01); *C08B 37/003* (2013.01); *C08J 3/16* (2013.01); *C08L 5/08* (2013.01); *C08L 79/02* (2013.01); *C08L 101/005* (2013.01); *C08J 2300/202* (2013.01); *C08J 2405/08* (2013.01); *C08L 2205/18* (2013.01)

(58) Field of Classification Search
CPC ........ A61K 31/722; C08L 5/08; C08B 37/003
See application file for complete search history.

(56) References Cited

U.S. PATENT DOCUMENTS

| | | | | |
|---|---|---|---|---|
| 3,879,376 A | * | 4/1975 | Vanlerberghe | A61K 8/736 536/20 |
| 5,821,221 A | * | 10/1998 | Shalaby | A61K 38/31 514/10.1 |
| 6,358,889 B2 | * | 3/2002 | Waggenspack | C08B 37/003 507/110 |
| 6,635,684 B2 | * | 10/2003 | Lai | C07K 17/08 521/50 |
| 6,780,822 B2 | * | 8/2004 | Cowan | C07H 3/10 507/110 |
| 2007/0213258 A1 | * | 9/2007 | Nakayama | A61M 1/3672 514/54 |
| 2008/0207561 A1 | * | 8/2008 | Utecht | A61K 9/0048 514/55 |
| 2013/0078210 A1 | * | 3/2013 | Yeo | C08L 5/08 424/78.17 |

OTHER PUBLICATIONS

Xu, Peisheng, et al. "Zwitterionic chitosan derivatives for pH-sensitive stealth coating." Biomacromolecules 11.9 (2010): 2352-2358.*
Opal, Steven M. "Endotoxins and other sepsis triggers." Endotoxemia and Endotoxin Shock. vol. 167. Karger Publishers, 2010. 14-24.*
Bajaj, Gaurav, William G. Van Alstine, and Yoon Yeo. "Zwitterionic chitosan derivative, a new biocompatible pharmaceutical excipient, prevents endotoxin-mediated cytokine release." PLoS One 7.1 (Jan. 2012): e30899.*
Kojima, Chic, et al. "Synthesis of polyamidoamine dendrimers having poly (ethylene glycol) grafts and their ability to encapsulate anticancer drugs." Bioconjugate Chemistry 11.6(2000): 910-917.
Mourya, V. K., and Nazma N. Inamdar. "Chitosan-modifications and applications: opportunities galore." Reactive and Functional polymers 68.6 (2008): 1013-1051.
Oliveira, Joaquim M., et al. "Surface engineered carboxymethylchitosan/poly(amidoamine) dendrimer nanoparticles for intracellular targeting." Advanced Functional Materials 18.12 (2008): 1840-1853.
Wiegand, C. et al., Molecular-weight-dependent toxic effects of chitosans on the human keratinocyte cell line HaCaT, Skin Pharmacal Physiol (2010) 23:164-170.
The United States Pharmacopeia: The National Formulary (USP33/NF28), Rockville, MD: The United States Pharmacopeial Convention, Inc. (2010).
Illum, L., Chitosan and its use as a pharmaceutical excipient, Pharmaceutical Research (1998) 15(9):1326-1331.
Baldrick, P., The safety of chitosan as a pharmaceutical excipient, Regulatory Toxicology and Pharmacology (2010) 56:290-299.
Qin, C. et al., Safety evaluation of short-term exposure to chitooligomers from enzymic preparation, Food and Chemical Toxicology (2006) 44:855-861.

(Continued)

*Primary Examiner* — Bethany P Barham
*Assistant Examiner* — Peter Anthopolos
(74) *Attorney, Agent, or Firm* — Wenderoth, Lind & Ponack, L.L.P.

(57) ABSTRACT

The present disclosure provides a polymer comprising a derivative of chitosan, wherein the derivative is zwitterionic, as well as methods of using the polymer. In addition, the present disclosure provides a nanoparticle structure comprising a derivative of chitosan and a dendrimer, as well as methods of utilizing the nanoparticle structure.

20 Claims, 25 Drawing Sheets

(56) References Cited

OTHER PUBLICATIONS

Hirano, S., Chitin biotechnology applications, Biotechnology Annual Review (1996) 2:237-258.
Obara, K. et al., Photocrosslinkable chitosan hydrogel containing fibroblast growth factor-2 stimulates wound healing in healing-impaired db/db mice, Biomaterials (2003) 24:3437-3444.
Ishihara, M. et al., Photocrosslinkable chitosan as a dressing for wound occlusion and accelerator in healing process, Biomaterials (2002) 23:833-840.
Ono, K. et al., Experimental evaluation of photocrosslinkable chitosan as a biologic adhesive with surgical applications, Surgery (2001) 130(5):844-850.
Kawashima, Y. et al., Mucoadhesive DL•lactide/glycolide copolymer nanospheres coated with chitosan to improve oral delivery of elcatonin, Pharmaceutical Development and Technology, (2000) 5(1):77-85.
Bowman, K. et al., Chitosan nanoparticles for oral drug and gene delivery, International Journal of Nanomedicine (2006) 1(2):117-128.
Roy, K. et al., Oral gene delivery with chitosan-DNA nanoparticles generates immunologic protection in a murine model of peanut allergy, Nature Medicine, (1999) 5(4):387-391.
Van Der Merwe, S.M. et al., Trimethylated chitosan as polymeric absorption enhancer for improved peroral delivery of peptide drugs, European Journal of Pharmaceutics and Biopharmaceutics (2004) 58:225-235.
Vandevord, P.J. et al., Evaluation of the biocompatibility of a chitosan scaffold in mice, Journal of Biomedical Materials Research (2002) 59:585-590.
Nettles, D.L. et al., Potential use of chitosan as a cell scaffold material for cartilage tissue engineering, Tissue Engineering (2002) 8(6):1009-1016.
Muzzarelli, R.A. Chitins and chitosans as immunoadjuvants and non-allergenic drug carriers, Marine Drugs (2010) 8:292-312.
Ono, K. et al., Photocrosslinkable chitosan as a biological adhesive, J Biomed Mater Res (2000) 49:289-295.
Amsden, B.G. et al., Methacrylated Glycol Chitosan as a Photopolymerizable Biomaterial, Biomacromolecules (2007) 8:3758-3766.
Park, J.H. et al., Self-assembled nanoparticles based on glycol chitosan bearing 5[beta]-cholanic acid for RGD peptide delivery, Journal of Controlled Release (2004) 95:579-588.
Park, K. et al., Effect of polymer molecular weight on the tumor targeting characteristics of self-assembled glycol chitosan nanoparticles, Journal of Controlled Release (2007) 122:305-314.
Min, K.H. et al., Hydrophobically modified glycol chitosan nanoparticles-encapsulated camptothecin enhance the drug stability and tumor targeting in cancer therapy, Journal of Controlled Release (2008) 127:208-218.
Dobrovolskaia, M.A. et al., Preclinical Studies to Understand Nanoparticle Interaction with the Immune System and Its Potential Effects on Nanoparticle Biodistribution, Molecular Pharmaceutics (2008) 5(4):487-495.
Mathews, S. et al., Cell mimetic monolayer supported chitosan•haemocompatibility studies, J Biomed Mater Res A (2006) 79:147-152.
Sagnella, S. et al., Chitosan based surfactant polymers designed to improve blood compatibility on biomaterials, Colloids and Surfaces B: Biointerfaces (2005) 42:147-155.
Minami, S. et al., Chitin and chitosan activate complement via the alternative pathway, Carbohydrate Polymers (1998) 36:151-155.
Yeo, Y. et al., Peritoneal application of chitosan and UV-cross-linkable chitosan, Journal of Biomedical Materials Research Part A (2006) 78A:668-675.
Peluso, G. et al., Chitosan-mediated stimulation of macrophage function, Biomaterials (1994) 15(15): 1215-1220.
Nishimura, K. et al., Stimulation of cytokine production in mice using deacetylated chitin, Vaccine (1986) 4:151-156.
Mori, T. et al., Endothelial cell responses to chitin and its derivatives, J Biomed Mater Res (1998) 43:469-472.
Mori, T. et al., Effects of chitin and its derivatives on the proliferation and cytokine production of fibroblasts in vitro, Biomaterials (1997) 18:94 7-951.
Canali, M.M. et al., Signals elicited at the intestinal epithelium upon chitosan feeding contribute to immunomodulatory activity and biocompatibility of the polysaccharide, Vaccine (2010) 28:5718-5724.
Tanaka, Y. et al., Effects of chitin and chitosan particles on BALB/c mice by oral and parenteral administration, Biomaterials (1997) 18:591-595.
Chellat, F. et al., Metalloproteinase and cytokine production by THP-1 macrophages following exposure to chitosan-DNA nanoparticles, Biomaterials (2005) 26:961-970.
Risbud, M. et al., Chitosan-polyvinyl pyrrolidone hydrogel does not activate macrophages: potentials for transplantation applications, Cell Transplantation (2001) 10:195-202.
Risbud, M. et al., Effect of chitosan-polyvinyl pyrrolidone hydrogel on proliferation and cytokine expression of endothelial cells: implications in islet immunoisolation, J Biomed Mater Res (2001) 57:300-305.
Kim, M.S. et al., Water-soluble chitosan inhibits the production of pro-inflammatory cytokine in human astrocytoma cells activated by amyloid [beta] peptide and interleukin-1[beta], Neuroscience Letters (2002) 321:105-109.
Liu, H.T. et al., Chitosan oligosaccharides inhibit the expression of interleukin-6 in lipopolysaccharide-induced human umbilical vein endothelial cells through p38 and ERK 1/2 protein kinases, Basic & Clinical Pharmacology & Toxicology (2009) 106:362-371.
Chen, C.L. et al., The effect of water-soluble chitosan on macrophage activation and the attenuation of mite allergen-induced airway inflammation, Biomaterials (2008) 29:2173-2182.
Nam, K.S. et al., Inhibition of proinflammatory cytokine-induced invasiveness of HT-29 cells by chitosan oligosaccharide, J Microbial Biotechnol (2007) 17(12):2042-2045.
Yoon, H.J. et al., Chitosan oligosaccharide (COS) inhibits LPS-induced inflammatory effects in RAW 264.7 macrophage cells, Biochemical and Biophysical Research Communications (2007) 358:954-959.
Azab, A.K. et al., Biocompatibility evaluation of crosslinked chitosan hydrogels after subcutaneous and intraperitoneal implantation in the rat, Journal of Biomedical Materials Research Part A (2007) 83A:414-422.
Kohane, D.S. et al., Biodegradable polymeric microspheres and nanospheres for drug delivery in the peritoneum, Journal of Biomedical Materials Research Part A (2006) 77A:351-361.
Guha, M. et al., LPS induction of gene expression in human monocytes, Cellular Signalling (2001) 13:85-94.
Dufrane, D. et al., The influence of implantation site on the biocompatibility and survival of alginate encapsulated pig islets in rats, Biomaterials (2006) 27:3201-3208.
Hall, J.C. et al., The pathobiology of peritonitis, Gastroenterology (1998) 114(1):185-196.
Anderson, J.M. et al., Foreign body reaction to biomaterials, Seminars in Immunology (2008) 20:86-100.
Usami, Y. et al., Migration of canine neutrophils to chitin and chitosan, J Vet Med Sci (1994) 56:1215-1216.
Lee, J. et al., Chemokine binding and activities mediated by the mouse IL-8 receptor, Journal of Immunology (1995) 155:2158-2164.
Chellat, F. et al., In vitro and in vivo biocompatibility of chitosan-xanthan polyionic complex, Journal of Biomedical Materials Research (2000) 51:107-116.

* cited by examiner

CHITOSAN DERIVATIVES FOR INACTIVATION OF ENDOTOXINS AND SURFACE PROTECTION OF NANOPARTICLES

STATEMENT OF FEDERALLY SPONSORED RESEARCH AND DEVELOPMENT

This invention was made with government support under grant number NIH R21CA135130 awarded by the National Institutes of Health. The U.S. Government has certain rights in the invention.

BACKGROUND OF INVENTION

Chitosan is a linear copolymer of D-glucosamine (2-amino-2-deoxy-D-glucose) and N-acetyl-D-glucosamine (2-acetamido-2-deoxy-D-glucose), obtained by partial (usually >80%) deacetylation of chitin, the main component of exoskeletons of insects and crustaceans. Chitosan has a low oral toxicity (oral $LD_{50}$: >10,000 mg/kg in mouse and >1500 mg/kg in rats) and has been used as a component in various dietary supplements. In addition, chitosan is safe for topical use and has been used as an ingredient of medical devices or cosmetics. Chitosan is considered to be a safe and biocompatible material, and has been widely explored as a pharmaceutical excipient for a variety of applications such as wound healing, surgical adhesives, mucoadhesive oral drug/gene delivery, gene delivery, and tissue engineering.

Furthermore, chitosan is known to have a pKa of approximately 6.5. Therefore, chitosan is insoluble at a neutral pH but is positively charged and water-soluble at an acidic pH. Although the limited solubility of chitosan at a neutral pH is hypothesized to allow for formation of nanoparticle drug/gene delivery platforms, such limited solubility is disadvantageous for applications of a solution of chitosan at physiological conditions.

In addition, some studies suggest that chitosans exhibit harmful biological effects when administered parenterally. For example, chitosan has been shown in some studies to cause a haemostatic effect and activation of complement following administration to an animal. Moreover, some studies suggest that chitosan induces pro-inflammatory cytokines or chemokines after administration. For example, intraperitoneal (IP) administration of chitosan has been shown to induce a large number of macrophages with hyperplasia in the mesenterium of mice and causes severe peritoneal adhesions in rabbits. In order for nanoparticles to be compatible with parenteral applications, the nanoparticles should not activate immune cells in the bloodstream (monocytes, platelets, leukocytes, and dendritic cells) or in tissues (resident phagocytes) because such activation could cause premature removal of the nanoparticles from the body, and/or elicit inflammatory responses in the body, following administration.

Therefore, there exists a need for chitosan derivatives that can be safely and effectively used as nanoparticles for parenteral administration to animals. Moreover, new and effective methods of utilizing a chitosan derivative, or compositions containing a chitosan derivative, are also very desirable. Accordingly, the present disclosure provides chitosan derivatives and methods of using the chitosan derivatives that exhibit desirable properties and provide related advantages for improvement in safety and efficacy after administration.

Additionally, chitosan derivatives may be advantageously utilized to aid in the delivery of other pharmaceutical compositions, such as dendrimers. Polyamidoamine ("PAMAM") dendrimers have previously been explored as pharmaceutical compositions for the delivery of therapeutic or imaging agents. PAMAM dendrimers can have various functional groups on their surface, for example amines, carboxylates, and amidoethylethanolamines. In particular, amine-terminated PAMAM dendrimers may be useful for gene delivery to animals because of their cationic charge, which allows for complexation of nucleic acids and for cellular uptake of the dendrimers. Moreover, protonation of tertiary amines in the interior of PAMAM dendrimers may facilitate endosomal escape via a "proton sponge" effect. Amine-termini of PAMAM dendrimers may also be useful for covalent conjugation of drugs via linkers cleaved by a condition unique to target tissues.

However, despite their ability to carry various agents, amine-terminated PAMAM dendrimers are generally not useful for systemic applications because of the non-specific toxicity and high risk associated with uptake by the reticuloendothelial system (RES). In an attempt to reduce the charge-related toxicity and prevent opsonization of cationic PAMAM dendrimers, a portion of their amine termini may be modified with polyethylene glycol (PEG), a hydrophilic linear polymer that masks the cationic charge. However, even after modification with polyethylene glycol (i.e., "pegylation"), modified PAMAM dendrimers can be disadvantageous due to the interference of PEG with the target cells. For example, PEG can interfere with important interactions between the carrier and the target cell, causing cellular uptake of the dendrimers to potentially be reduced. Even further modification of the pegylated PAMAM dendrimers with folate, transferrin, or RGD peptide (i.e., ligands known to enhance interactions with target cells) does not solve the problems because the fraction of target cells that express corresponding cellular receptors is not always predictable, and the expression level can change during progression of the disease(s) to be treated.

Therefore, there exists a need for the modification of dendrimers (e.g., PAMAM dendrimers) to provide for their safe and effective administration to animals. Moreover, new and effective methods of utilizing such modified dendrimers are also very desirable. Accordingly, the present disclosure also provides a nanoparticle structure comprising a derivative of chitosan and a dendrimer, as well as methods of using the nanoparticle structure, that exhibit desirable properties and provide related advantages for improvement in administering dendrimers to animals.

BRIEF SUMMARY OF INVENTION

The present disclosure provides a zwitterionic derivative of chitosan, polymers comprising the zwitterionic chitosan derivative, and methods of using the zwitterionic chitosan derivative and the polymers. In addition, the present disclosure provides a nanoparticle structure comprising the zwitterionic chitosan derivative and a dendrimer, as well as methods of utilizing the nanoparticle structure.

The zwitterionic chitosan derivative, the nanoparticle structure, and the methods according to the present disclosure provide several advantages compared to other compositions and methods in the art.

First, the zwitterionic chitosan derivative has a unique pH-dependent charge profile, with isoelectric points (pI) that are tunable among a pH range from about 4 to about 7. Because the chitosan derivative is zwitterionic, it is soluble in water at pHs below and above the pI, according to the change of its net charge. As a result, the zwitterionic chitosan derivative can be used for parenteral applications, specifically as a component of nanoparticulate drug delivery systems.

Second, the zwitterionic chitosan derivative demonstrates excellent compatibility with blood components and is well tolerated following IP injection. Compared to its precursors (e.g., low molecular weight chitosan), the zwitterionic chitosan derivative has a reduced potential to cause hemolysis, complement activation, and pro-inflammatory response.

Third, the zwitterionic chitosan derivative demonstrates a lower incidence of causing tissue reactions and has a reduced propensity to induce pro-inflammatory cytokine production from macrophages. The zwitterionic chitosan derivative surprisingly suppresses pro-inflammatory responses of activated macrophages.

Fourth, the zwitterionic chitosan derivative can advantageously be used to decrease endotoxins in a composition or in a subject. Endotoxins are a product of the cell wall of gram-negative bacteria and are a common cause of toxic reactions due to their potent stimulation of the mammalian immune system. It is believed that the zwitterionic chitosan derivative may be able to bind to lipopolysaccharides in order to decrease endotoxin levels. Thus, the zwitterionic chitosan derivative may provide an efficient and cost-effective way of removing endotoxin from pharmaceutical products or may serve as a portable reagent for water treatment, such as in war zones or underdeveloped countries.

Fifth, the zwitterionic chitosan derivative can be used to provide safe delivery of cationic polymer nanoparticles to cells by shielding them in normal conditions and activating them only upon exposure to common features of diseased tissues or organs. For example, the microenvironment of a tumor could advantageously be used in this regard. Cancer cells distant from blood vessels are typically deprived of oxygen and undergo anaerobic glycolysis to generate excess lactic acid. As a result, hypoxic tumors tend to develop a weakly acidic microenvironment (e.g., a pH of about 6.5 to about 7.2) compared to normal tissues. Accordingly, the zwitterionioc chitosan derivative of the present disclosure can be used to modify the surface of an amine-terminated PAMAM dendrimer and shield its cationic surface of the dendrimer allow cellular entry in a pH-responsive manner. In an acidic environment, the zwitterionic chitosan derivative can undergo charge reversal, thus allowing PAMAM to interact with tumor cells. For example, following charge reversal, the dendrimer could be effectively delivered to the cell, an agent carried by the dendrimer could be effectively delivered to the cell, or a combination of both.

Sixth, the nanoparticles and the zwitterionic chitosan derivatives of which the nanoparticles are comprised can be used in methods of treating certain diseases and conditions in a subject, such as a human or other mammal. For example, because the zwitterionic chitosan derivative can suppress the pro-inflammatory responses of activated macrophages, the zwitterionic chitosan derivative can be used in methods of suppressing an inflammatory response in a subject. Because the zwitterionic chitosan derivative binds to lipopolysaccharides (LPS), the zwitterionic chitosan derivative can be used in methods of suppressing cytokine or chemokine production in a subject. Further in light of the ability of the zwitterionic chitosan derivative to bind LPS, the zwitterionic chitosan derivative can also be used in methods of treating or preventing a septic condition in a subject.

The following numbered embodiments are contemplated and are non-limiting:

1. A nanoparticle structure comprising a derivative of chitosan and a dendrimer.

2. The nanoparticle of clause 1, wherein the nanoparticle structure is a complex of the derivative of chitosan and the dendrimer.

3. The nanoparticle of clause 2, wherein the complex is an electrostatic complex.

4. The nanoparticle of any one of clauses 1 to 3, wherein the nanoparticle structure has a ratio of derivative:dendrimer at about 1:1.

5. The nanoparticle of any one of clauses 1 to 3, wherein the nanoparticle structure has a ratio of derivative:dendrimer at about 2:1.

6. The nanoparticle of any one of clauses 1 to 3, wherein the nanoparticle structure has a ratio of derivative:dendrimer at about 3:1.

7. The nanoparticle of any one of clauses 1 to 3, wherein the nanoparticle structure has a ratio of derivative:dendrimer at about 4:1.

8. The nanoparticle of any one of clauses 1 to 7, wherein the nanoparticle structure has a critical association concentration between about 2.0 µg/mL and about 3.0 µg/mL.

9. The nanoparticle of any one of clauses 1 to 8, wherein the nanoparticle structure has a critical association concentration of about 2.5 µg/mL.

10. The nanoparticle of any one of clauses 1 to 8, wherein the nanoparticle structure has a critical association concentration of about 2.7 µg/mL.

11. The nanoparticle of any one of clauses 1 to 10, wherein the size of the nanoparticle structure is between about 100 nm and about 500 nm.

12. The nanoparticle of any one of clauses 1 to 10, wherein the size of the nanoparticle structure is between about 200 nm and about 400 nm.

13. The nanoparticle of any one of clauses 1 to 12, wherein the size of the nanoparticle structure is about 200 nm.

14. The nanoparticle of any one of clauses 1 to 12, wherein the size of the nanoparticle structure is about 250 nm.

15. The nanoparticle of any one of clauses 1 to 12, wherein the size of the nanoparticle structure is about 300 nm.

16. The nanoparticle of any one of clauses 1 to 12, wherein the size of the nanoparticle structure is about 350 nm.

17. The nanoparticle of any one of clauses 1 to 12, wherein the size of the nanoparticle structure is about 400 nm.

18. The nanoparticle of any one of clauses 1 to 17, wherein the derivative is zwitterionic.

19. The nanoparticle of any one of clauses 1 to 18, wherein the derivative has an isoelectric point (pI) between about 4 and about 7.

20. The nanoparticle of any one of clauses 1 to 19, wherein the derivative has a pI of about 4.5.

21. The nanoparticle of any one of clauses 1 to 19, wherein the derivative has a pI of about 5.0.

22. The nanoparticle of any one of clauses 1 to 19, wherein the derivative has a pI of about 5.5.

23. The nanoparticle of any one of clauses 1 to 19, wherein the derivative has a pI of about 6.0.

24. The nanoparticle of any one of clauses 1 to 19, wherein the derivative has a pI of about 6.5.

25. The nanoparticle of any one of clauses 1 to 19, wherein the derivative has a pI of about 6.8.

26. The nanoparticle of any one of clauses 1 to 19, wherein the derivative has a pI of about 7.0.

27. The nanoparticle of any one of clauses 1 to 26, wherein the derivative has an An/Am ratio between 0.3 to 0.7.

28. The nanoparticle of any one of clauses 1 to 27, wherein the derivative has an An/Am ratio of about 0.3.

29. The nanoparticle of any one of clauses 1 to 27, wherein the derivative has an An/Am ratio of about 0.4.

30. The nanoparticle of any one of clauses 1 to 27, wherein the derivative has an An/Am ratio of about 0.5.

31. The nanoparticle of any one of clauses 1 to 27, wherein the derivative has an An/Am ratio of about 0.6.

32. The nanoparticle of any one of clauses 1 to 27, wherein the derivative has an An/Am ratio of about 0.7.

33. The nanoparticle of any one of clauses 1 to 32, wherein the dendrimer is poly(amidoamine) ("PAMAM").

34. The nanoparticle of clause 33, wherein the PAMAM dendrimer is an amine-terminated G5 PAMAM dendrimer.

35. A method of delivering a dendrimer to a cell, said method comprising the step of administering a nanoparticle structure comprising a derivative of chitosan and a dendrimer to the cell.

36. The method of clause 35, wherein the cell is a cancer cell.

37. The method of clause 35 or clause 36, wherein the nanoparticle structure releases the dendrimer to the cell.

38. The method of clause 37, wherein the release occurs at an acidic pH.

39. The method of clause 38, wherein the acidic pH is caused by hypoxia.

40. The method of clause 38, wherein the acidic pH is caused by the Warburg effect.

41. The method of any one of clauses 36 to 40, wherein the delivery to the cell is entry into the cell.

42. The method of clause 41, wherein the entry into the cell results in apoptosis of the cell.

43. The method of clause 42, wherein the apoptosis results from delivery of the dendrimer to the cell.

44. The method of clause 42, wherein the apoptosis results from delivery of an agent to the cell and wherein the agent is contained within the dendrimer or covalently conjugated to the dendrimer.

45. A method of delivering a dendrimer to a cell in a subject, said method comprising the step of administering an effective amount of a nanoparticle structure to the subject, wherein the nanoparticle structure comprises a derivative of chitosan and a dendrimer.

46. The method of clause 45, wherein the cell is associated with a tumor in the subject.

47. The method of clause 46, wherein the tumor is a solid tumor.

48. The method of any one of clauses 45 to 47, wherein the nanoparticle structure releases the dendrimer to the cell in the subject.

49. The method of clause 48, wherein the release occurs at an acidic pH.

50. The method of clause 49, wherein the acidic pH is caused by hypoxia.

51. The method of clause 50, wherein the acidic pH is caused by the Warburg effect.

52. The method of any one of clauses 45 to 51, wherein the delivery to the cell is entry into the cell.

53. The method of clause 52, wherein the entry into the cell results in apoptosis of the cell.

54. The method of clause 53, wherein the apoptosis results from delivery of the dendrimer to the cell.

55. The method of clause 54, wherein the apoptosis results from delivery of an agent to the cell and wherein the agent is contained within the dendrimer or covalently conjugated to the dendrimer.

56. A method of delivering an agent to a subject, said method comprising the step of administering a nanoparticle structure to the subject, wherein the nanoparticle structure comprises a derivative of chitosan, a dendrimer, and the agent.

57. The method of clause 56, wherein the agent is contained within the dendrimer or covalently conjugated to the dendrimer.

58. The method of clause 56 or clause 57, wherein the agent is delivered to a cell in the subject.

59. The method of any one of clauses 56 to 58, wherein the agent is a pharmaceutical compound.

60. The method of clause 59, wherein the pharmaceutical compound is an anticancer drug.

61. The method of any one of clauses 56 to 58, wherein the agent is an imaging agent.

62. The method of any one of clauses 56 to 61, wherein the cell is a cancer cell.

63. The method of any one of clauses 56 to 62, wherein the cell is associated with a tumor in the subject.

64. The method of clause 63, wherein the tumor is a solid tumor.

65. The method of any one of clauses 56 to 64, wherein the nanoparticle structure releases the dendrimer to the cell in the subject.

66. The method of clause 65, wherein the release occurs at an acidic pH.

67. The method of clause 66, wherein the acidic pH is caused by hypoxia.

68. A polymer comprising a derivative of chitosan, wherein the derivative is zwitterionic.

69. The polymer of clause 68, wherein the derivative has an isoelectric point (pI) between about 4 and about 7.

70. The polymer of clause 68 or clause 69, wherein the derivative has a pI of about 4.5.

71. The polymer of clause 68 or clause 69, wherein the derivative has a pI of about 5.0.

72. The polymer of clause 68 or clause 69, wherein the derivative has a pI of about 5.5.

73. The polymer of clause 68 or clause 69, wherein the derivative has a pI of about 6.0.

74. The polymer of clause 68 or clause 69, wherein the derivative has a pI of about 6.5.

75. The polymer of clause 68 or clause 69, wherein the derivative has a pI of about 6.8.

76. The polymer of clause 68 or clause 69, wherein the derivative has a pI of about 7.0.

77. The polymer of any one of clauses 68 to 76, wherein the derivative has an An/Am ratio between 0.3 to 0.7.

78. The polymer of any one of clauses 68 to 77, wherein the derivative has an An/Am ratio of about 0.3.

79. The polymer of any one of clauses 68 to 77, wherein the derivative has an An/Am ratio of about 0.4.

80. The polymer of any one of clauses 68 to 77, wherein the derivative has an An/Am ratio of about 0.5.

81. The polymer of any one of clauses 68 to 77, wherein the derivative has an An/Am ratio of about 0.6.

82. The polymer of any one of clauses 68 to 77, wherein the derivative has an An/Am ratio of about 0.7.

83. A method of suppressing an inflammatory response in a subject, said method comprising the step of administering an effective amount of a polymer to the subject, wherein the polymer comprises a zwitterionic derivative of chitosan.

84. The method of clause 83, wherein the inflammatory response is associated with activated macrophages in the subject.

85. The method of clause 83 or clause 84, wherein the inflammatory response is pro-inflammatory cytokine production.

86. The method of clause 85, wherein the cytokine production is IL-6 production.

87. The method of clause 85, wherein the cytokine production is TNF-α production.

88. The method of clause 83 or clause 84, wherein the inflammatory response is pro-inflammatory chemokine production.

89. The method of clause 88, wherein the chemokine production is MIP-2 production. 90. The method of any one of clauses 83 to 89, wherein the derivative has an isoelectric point (pI) between about 4 and about 7.

91. The method of any one of clauses 83 to 90, wherein the derivative has a pI of about 4.5.

92. The method of any one of clauses 83 to 90, wherein the derivative has a pI of about 5.0.

93. The method of any one of clauses 83 to 90, wherein the derivative has a pI of about 5.5.

94. The method of any one of clauses 83 to 90, wherein the derivative has a pI of about 6.0.

95. The method of any one of clauses 83 to 90, wherein the derivative has a pI of about 6.5.

96. The method of any one of clauses 83 to 90, wherein the derivative has a pI of about 6.8.

97. The method of any one of clauses 83 to 90, wherein the derivative has a pI of about 7.0.

98. The method of any one of clauses 83 to 97, wherein the derivative has an An/Am ratio between 0.3 to 0.7.

99. The method of any one of clauses 83 to 98, wherein the derivative has an An/Am ratio of about 0.3.

100. The method of any one of clauses 83 to 98, wherein the derivative has an An/Am ratio of about 0.4.

101. The method of any one of clauses 83 to 98, wherein the derivative has an An/Am ratio of about 0.5.

102. The method of any one of clauses 83 to 98, wherein the derivative has an An/Am ratio of about 0.6.

103. The method of any one of clauses 83 to 98, wherein the derivative has an An/Am ratio of about 0.7.

104. A method of suppressing cytokine or chemokine production in a subject, said method comprising the step of administering a therapeutically effective amount of a polymer to the subject, wherein the polymer comprises a zwitterionic derivative of chitosan.

105. The method of clause 104, wherein the cytokine or chemokine production is associated with activated macrophages.

106. The method of clause 104 or clause 105, wherein the cytokine or chemokine production is induced by lipopolysaccharide (LPS).

107. The method of clause 106, wherein the polymer binds directly to the LPS.

108. The method of any one of clauses 104 to 107, wherein the cytokine is IL-6.

109. The method of any one of clauses 104 to 107, wherein the cytokine is TNF-α.

110. The method of any one of clauses 104 to 107, wherein the chemokine is MIP-2.

111. The method of any one of clauses 104 to 110, wherein the derivative has an isoelectric point (pI) between about 4 and about 7.

112. The method of any one of clauses 104 to 111, wherein the derivative has a pI of about 4.5.

113. The method of any one of clauses 104 to 111, wherein the derivative has a pI of about 5.0.

114. The method of any one of clauses 104 to 111, wherein the derivative has a pI of about 5.5.

115. The method of any one of clauses 104 to 111, wherein the derivative has a pI of about 6.0.

116. The method of any one of clauses 104 to 111, wherein the derivative has a pI of about 6.5.

117. The method of any one of clauses 104 to 111, wherein the derivative has a pI of about 6.8.

118. The method of any one of clauses 104 to 111, wherein the derivative has a pI of about 7.0.

119. The method of any one of clauses 104 to 118, wherein the derivative has an An/Am ratio between 0.3 to 0.7.

120. The method of any one of clauses 104 to 119, wherein the derivative has an An/Am ratio of about 0.3.

121. The method of any one of clauses 104 to 119, wherein the derivative has an An/Am ratio of about 0.4.

122. The method of any one of clauses 104 to 119, wherein the derivative has an An/Am ratio of about 0.5.

123. The method of any one of clauses 104 to 119, wherein the derivative has an An/Am ratio of about 0.6.

124. The method of any one of clauses 104 to 119, wherein the derivative has an An/Am ratio of about 0.7.

125. A method of binding a lipopolysaccharide, said method comprising the step of contacting the lipopolysaccharide with a polymer comprising a zwitterionic derivative of chitosan.

126. The method of clause 125, wherein the derivative has an isoelectric point (pI) between about 4 and about 7.

127. The method of clause 125 or clause 126, wherein the derivative has a pI of about 4.5.

128. The method of any one of clauses 125 to 127, wherein the derivative has a pI of about 5.0.

129. The method of any one of clauses 125 to 127, wherein the derivative has a pI of about 5.5.

130. The method of any one of clauses 125 to 127, wherein the derivative has a pI of about 6.0.

131. The method of any one of clauses 125 to 127, wherein the derivative has a pI of about 6.5.

132. The method of any one of clauses 125 to 127, wherein the derivative has a pI of about 6.8.

133. The method of any one of clauses 125 to 127, wherein the derivative has a pI of about 7.0.

134. The method of any one of clauses 125 to 133, wherein the derivative has an An/Am ratio between 0.3 to 0.7.

135. The method of any one of clauses 125 to 134, wherein the derivative has an An/Am ratio of about 0.3.

136. The method of any one of clauses 125 to 134, wherein the derivative has an An/Am ratio of about 0.4.

137. The method of any one of clauses 125 to 134, wherein the derivative has an An/Am ratio of about 0.5.

138. The method of any one of clauses 125 to 134, wherein the derivative has an An/Am ratio of about 0.6.

139. The method of any one of clauses 125 to 134, wherein the derivative has an An/Am ratio of about 0.7.

140. A method of decreasing the amount of a bacterial toxin in a subject, said method comprising the step of administering an effective amount of a polymer to the subject, wherein the polymer comprises a zwitterionic derivative of chitosan.

141. The method of clause 140, wherein the bacterial toxin is an endotoxin.

142. The method of clause 140 or clause 141, wherein the derivative has an isoelectric point (pI) between about 4 and about 7.

143. The method of any one of clauses 140 to 142, wherein the derivative has a pI of about 4.5.

144. The method of any one of clauses 140 to 142, wherein the derivative has a pI of about 5.0.

145. The method of any one of clauses 140 to 142, wherein the derivative has a pI of about 5.5.

146. The method of any one of clauses 140 to 142, wherein the derivative has a pI of about 6.0.

147. The method of any one of clauses 140 to 142, wherein the derivative has a pI of about 6.5.

148. The method of any one of clauses 140 to 142, wherein the derivative has a pI of about 6.8.

149. The method of any one of clauses 140 to 142, wherein the derivative has a pI of about 7.0.

150. The method of any one of clauses 140 to 149, wherein the derivative has an An/Am ratio between 0.3 to 0.7.

151. The method of any one of clauses 140 to 150, wherein the derivative has an An/Am ratio of about 0.3.

152. The method of any one of clauses 140 to 150, wherein the derivative has an An/Am ratio of about 0.4.

153. The method of any one of clauses 140 to 150, wherein the derivative has an An/Am ratio of about 0.5.

154. The method of any one of clauses 140 to 150, wherein the derivative has an An/Am ratio of about 0.6.

155. The method of any one of clauses 140 to 150, wherein the derivative has an An/Am ratio of about 0.7.

156. A method of decreasing the amount of a bacterial toxin in a composition, said method comprising the step of administering an effective amount of a polymer to the composition, wherein the polymer comprises a zwitterionic derivative of chitosan.

157. The method of clause 156, wherein the bacterial toxin is an endotoxin. 158. The method of clause 156 or clause 157, wherein the composition is a pharmaceutical composition.

159. The method of clause 156 or clause 157, wherein the composition is water. 160. The method of any one of clauses 156 to 159, wherein the derivative has an isoelectric point (pI) between about 4 and about 7.

161. The method of any one of clauses 156 to 160, wherein the derivative has a pI of about 4.5.

162. The method of any one of clauses 156 to 160, wherein the derivative has a pI of about 5.0.

163. The method of any one of clauses 156 to 160, wherein the derivative has a pI of about 5.5.

164. The method of any one of clauses 156 to 160, wherein the derivative has a pI of about 6.0.

165. The method of any one of clauses 156 to 160, wherein the derivative has a pI of about 6.5.

166. The method of any one of clauses 156 to 160, wherein the derivative has a pI of about 6.8.

167. The method of any one of clauses 156 to 160, wherein the derivative has a pI of about 7.0.

168. The method of any one of clauses 156 to 167, wherein the derivative has an An/Am ratio between 0.3 to 0.7.

169. The method of any one of clauses 156 to 168, wherein the derivative has an An/Am ratio of about 0.3.

170. The method of any one of clauses 156 to 168, wherein the derivative has an An/Am ratio of about 0.4.

171. The method of any one of clauses 156 to 168, wherein the derivative has an An/Am ratio of about 0.5.

172. The method of any one of clauses 156 to 168, wherein the derivative has an An/Am ratio of about 0.6.

173. The method of any one of clauses 156 to 168, wherein the derivative has an An/Am ratio of about 0.7.

174. A method of suppressing an inflammatory response in a subject, said method comprising administering a therapeutically effective amount of a zwitterionic derivative of chitosan to a subject in need thereof.

175. The method of clause 174, wherein the inflammatory response is induced in the subject by a bacterial infection.

176. The method of clause 174 or 175, wherein the inflammatory response is induced in the subject by bacterial lipopolysaccharide (LPS).

177. A method of suppressing cytokine or chemokine production in a subject, said method comprising administering a therapeutically effective amount of a zwitterionic derivative of chitosan to a subject in need thereof.

178. The method of clause 177, wherein cytokine or chemokine production is induced in the subject by a bacterial infection.

179. The method of clause 177 or 178, wherein cytokine or chemokine production is induced in the subject by bacterial lipopolysaccharide (LPS).

180. A method of treating a septic condition in a subject, said method comprising administering a therapeutically effective amount of a zwitterionic derivative of chitosan to a subject in need thereof.

181. The method of clause 180, wherein the septic condition is induced in the subject by a bacterial infection.

182. The method of clause 180 or 181, wherein the septic condition is induced in the subject by bacterial lipopolysaccharide (LPS).

183. The method of any one of clauses 180 to 182, wherein the septic condition is one or more of sepsis, severe sepsis, and septic shock.

184. The method of any one of clause 174 to 183, wherein the zwitterionic derivative of chitosan exhibits an anhydride to amine (An/Am) ratio of 0.3 to 0.7.

185. The method of any one of clause 174 to 184, wherein the zwitterionic derivative of chitosan was synthesized by partial amidation of a chitosan with succinic anhydride.

186. A method of suppressing cytokine or chemokine production in a subject, said method comprising the step of administering a therapeutically effective amount of a nanoparticle of any one of clauses 1 to 34 to a subject in need thereof, wherein the nanoparticle comprises a zwitterionic derivative of chitosan.

187. The method of clause 186, wherein the cytokine or chemokine production is associated with activated macrophages.

188. The method of clause 186 or 187, wherein the cytokine or chemokine production is induced by lipopolysaccharide (LPS).

189. The method of clause 188, wherein the polymer binds directly to the LPS.

190. The method of any one of clauses 186 to 189, wherein the cytokine is IL-6.

191. The method of any one of clauses 186 to 189, wherein the cytokine is TNF-α.

192. The method of any one of clauses 186 to 189, wherein the chemokine is MIP-2.

193. The method of any one of clauses 186 to 189, wherein the derivative has an isoelectric point (pI) between about 4 and about 7.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

Figure 1:
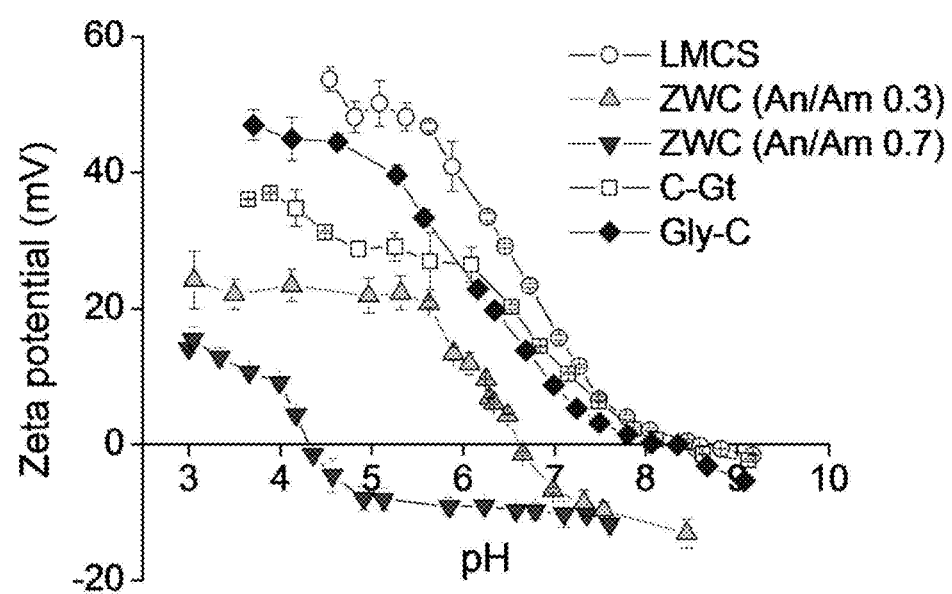
FIG. 1 shows pH-dependent zeta-potential profiles of unmodified low molecular weight chitosan (LMCS) and zwitterionic chitosan (ZWC) derivatives prepared with different anhydride to amine (An/Am) ratios, chitosan glutamate (C-Gt), and glycol chitosan (Gly-C). Data are expressed as averages with standard deviations of 3 repeated measurements.

Various embodiments of the invention are described herein as follows. In one embodiment described herein, a nanoparticle structure is provided. The nanoparticle structure comprises a derivative of chitosan and a dendrimer.

In another embodiment, a method of delivering a dendrimer to a cell is provided. The method comprises the step of administering a nanoparticle structure comprising a derivative of chitosan and a dendrimer to the cell.

In yet another embodiment, a method of delivering a dendrimer to a cell in a subject is provided. The method comprises the step of administering an effective amount of a nanoparticle structure to the subject, wherein the nanoparticle structure comprises a derivative of chitosan and a dendrimer.

In a further embodiment, a method of delivering an agent to a subject is provided. The method comprises the step of administering a nanoparticle structure to the subject, wherein the nanoparticle structure comprises a derivative of chitosan, a dendrimer, and the agent.

In another embodiment, a zwitterionic derivative of chitosan is provided. In a related embodiment, a polymer comprising the zwitterionic derivative of chitosan is provided.

In yet another embodiment, a method of suppressing an inflammatory response in a subject is provided. The method comprises the step of administering a therapeutically effective amount of a zwitterionic derivative of chitosan or a nanoparticle as defined herein comprising a zwitterionic derivative of chitosan to a subject in need thereof, such as a subject experiencing a dysregulated or uncontrolled inflammatory response. In certain aspects of this embodiment, the inflammatory response is induced in the subject by a bacterial infection. In certain aspects of this embodiment, the inflammatory response is induced in the subject by bacterial lipopolysaccharide (LPS). In certain aspects of this embodiment, the inflammatory response is associated with activated macrophages in the subject. The phrase "activated macrophage" is well known in the art, and includes cells that secrete inflammatory mediators and target and/or kill intracellular pathogens in the subject. In some aspects, the inflammatory response is pro-inflammatory cytokine production. Pro-inflammatory cytokines are well known in the field of immunology and include, but are not limited to, Interleukin-1β (IL-1β), interleukin-6 (IL-6), interleukin-12 (IL-12), interferon-γ (IFN-γ), and tumor necrosis factor alpha (TNF-α). In aspect, the cytokine production is IL-6 production. In another aspect, the cytokine production is TNF-α production. In some aspects, the inflammatory response is pro-inflammatory chemokine production. Pro-inflammatory chemokines are well known in the art of immunology. In one aspect, the chemokine production is Macrophage Inflammatory Protein 2 (MIP-2) production.

In a further embodiment, a method of suppressing cytokine or chemokine production in a subject is provided. The method comprises the step of administering an effective amount of a zwitterionic derivative of chitosan or a nanoparticle as defined herein comprising a zwitterionic derivative of chitosan to a subject in need thereof, such as a subject experiencing dysregulated or uncontrolled cytokine or chemokine production. In certain aspects of this embodiment, cytokine or chemokine production is by white blood cells. In certain aspects of this embodiment, cytokine or chemokine production is by one or more of monocytes, neutrophils, eosinophils, basophils, lymphocytes, macrophages, B cells, T cells, natural killer cells, dendritic cells, and follicular dendritic cells. In certain aspects of this embodiment, cytokine or chemokine production is induced in the subject by a bacterial infection. In certain aspects of this embodiment, cytokine or chemokine production is induced in the subject by bacterial lipopolysaccharide (LPS). In some aspects, cytokine production is the production of pro-inflammatory cytokines. Pro-inflammatory cytokines are well known in the field of immunology and include, but are not limited to, Interleukin-1β (IL-1β), interleukin-6 (IL-6), interleukin-12 (IL-12), interferon-γ (IFN-γ), and tumor necrosis factor alpha (TNF-α). In aspect, the cytokine production is IL-6 production. In another aspect, the cytokine production is TNF-α production. In some aspects, chemokine production is the production of pro-inflammatory chemokine. Pro-inflammatory chemokines are well known in the art of immunology. In one aspect, the chemokine production is Macrophage Inflammatory Protein 2 (MIP-2) production.

In another embodiment, a method of binding a lipopolysaccharide is provided. The method comprises the step of contacting the lipopolysaccharide with a zwitterionic derivative of chitosan or a nanoparticle as defined herein comprising a zwitterionic derivative of chitosan.

In yet another embodiment, a method of decreasing the amount of a bacterial toxin in a subject is provided. The method comprises the step of administering an effective amount of a zwitterionic derivative of chitosan or a nanoparticle as defined herein comprising a zwitterionic derivative of chitosan to a subject in need thereof, such as a subject infected with a bacterial toxin. In certain aspects of this embodiment, the bacterial toxin is lipopolysaccharide (LPS). In certain aspects, the bacterial toxin is an endotoxin. As used herein, the term "endotoxin" refers to a toxin that is present inside a bacterial cell (for example, a cell wall) and is released when the cell is broken down (e.g., dies).

In a further embodiment, a method of decreasing a bacterial toxin in a composition is provided. The method comprises the step of contacting a bacterial toxin in a composition with an effective amount of a zwitterionic derivative of chitosan or a nanoparticle as defined herein comprising a zwitterionic derivative of chitosan. The contacting may be in vitro, ex vivo or in vivo.

In another embodiment, a method of treating a septic condition in a subject is provided. The method comprises administering a therapeutically effective amount of a zwitterionic derivative of chitosan or a nanoparticle as defined herein comprising a zwitterionic derivative of chitosan to a subject in need thereof, such as a subject experiencing a septic condition. In certain aspects of this embodiment, the septic condition is sepsis (systemic inflammatory response syndrome (SIRS) in response to an infectious process), severe sepsis (sepsis with sepsis-induced organ dysfunction or tissue hypoperfusion), or septic shock (severe sepsis plus persistently low blood pressure despite the administration of intravenous fluids). In some aspects of this embodiment, the septic condition is induced by a bacterial infection, such as an infection by a strain of a gram-negative bacteria. In certain aspects of this embodiment, the septic condition is included in the subject by lipopolysaccharide (LPS).

In the various embodiments, the nanoparticle structure comprises a derivative of chitosan and a dendrimer. As used herein, the term "nanoparticle" refers to a particle having a size measured on the nanometer scale. As used herein, the "nanoparticle" refers to a particle having a structure with a size of less than about 1,000 nanometers. As used herein, the term "chitosan" refers to a linear copolymer of D-glucosamine (2-amino-2-deoxy-D-glucose) and N-acetyl-D-glucosamine (2-acetamido-2-deoxy-D-glucose), obtained by partial deacetylation of chitin, the main component of exoskeletons of insects and crustaceans. A "derivative" of chitosan refers to refers to compound or portion of a compound that is derived from or is theoretically derivable from chitosan. As used herein, the term "dendrimer" refers to a molecule built up from a single starting molecule by sequential covalent reactions with a molecule having reactive sites to produce a branched molecule including terminal reactive groups. An example of the synthesis of a dendrimer is the synthesis of poly(amido-amine) ("PAMAM") dendrimers including terminal amine groups, as described in Tomalia et al., Macromolecules, 19 2466 (1986); and U.S. Pat. No. 4,568,737 to Tomalia et al., the disclosures of which are incorporated herein. For example dendrimers may be synthesized with 4, 8, 16, 32, 64, 128, 256, or more primary amine groups.

In some embodiments described herein, the nanoparticle structure is a complex of the derivative of chitosan and the dendrimer. As used herein, the term "complex" refers to a molecular association, which can be non-covalent, between two molecular or atomic entities. In various embodiments, the complex is an electrostatic complex.

In various embodiments described herein, the nanoparticle structure can comprise various ratios of derivative to dendrimer (derivative:dendrimer). In one embodiment, the nanoparticle structure has a ratio of derivative:dendrimer at about 1:1. In another embodiment, the nanoparticle structure has a ratio of derivative:dendrimer at about 2:1. In yet another embodiment, the nanoparticle structure has a ratio of derivative:dendrimer at about 3:1. In another embodiment, the nanoparticle structure has a ratio of derivative:dendrimer at about 4:1.

In some embodiments described herein, the nanoparticle structure has a specified critical association concentration (CAC). As used herein, the term "critical association concentration" refers to the lowest concentration at which components of the nanoparticle structure are able to form a complex, for example an electrostatic complex. In one embodiment, the nanoparticle structure has a critical association concentration of about 2.5 µg/mL. In another embodiment, the nanoparticle structure has a critical association concentration of about 2.7 µg/mL.

In various embodiments described herein, the nanoparticle structures can have a specified size. In one embodiment, the size of the nanoparticle structure is between about 100 nm and about 500 nm. In another embodiment, the size of the nanoparticle structure is between about 200 nm and about 400 nm. In yet another embodiment, the size of the nanoparticle structure is about 200 nm. In one embodiment, the size of the nanoparticle structure is about 250 10 nm. In another embodiment, the size of the nanoparticle structure is about 300 nm. In yet another embodiment, the size of the nanoparticle structure is about 350 nm. In another embodiment, the size of the nanoparticle structure is about 400 nm.

In some embodiments described herein, the derivative of chitosan is zwitterionic. As used herein, the term "zwitterionic" refers to a molecule that has both a negative and positive charges in the molecule, for example where the negative charge comes from the carboxyl group and the positive charge comes from the amine group. For example, a "zwitterion" of chitosan may be produced by partial amidation of chitosan with one or more compounds that provide anionic groups (e.g., succinic anhydride). In some embodiments, the derivative has an isoelectric point (pI) between about 4 and about 7. In one embodiment, the derivative has a pI of about 4.5.

In another embodiment, the derivative has a pI of about 5.0. In yet another embodiment, the derivative has a pI of about 5.5. In one embodiment, the derivative has a pI of about 6.0. In another embodiment, the derivative has a pI of about 6.5. In another embodiment, the derivative has a pI of about 6.8. In yet another embodiment, the derivative has a pI of about 7.0.

In various embodiments described herein, the chitosan derivatives can have a specified molar feed ratio of anhydride to amine (An/Am ratio). In one embodiment, the derivative has an An/Am ratio between 0.3 and 0.7. In another embodiment, the derivative has an An/Am ratio of about 0.3. In yet another embodiment, the derivative has an An/Am ratio of about 0.4. In another embodiment, the derivative has an An/Am ratio of about 0.5. In another embodiment, the derivative has an An/Am ratio of about 0.6. In yet another embodiment, the derivative has an An/Am ratio of about 0.7.

In various embodiments described herein, the dendrimer is poly(amidoamine) ("PAMAM"). The core of a PAMAM dendrimer is a diamine (such as ethylenediamine), which is reacted with methyl acrylate, and then another ethylenediamine to make the generation-0 (G-0) PAMAM. Successive reactions create higher generations. In some embodiments, the PAMAM dendrimer is an amine-terminated generation 5 (G5) PAMAM dendrimer.

In one embodiment described herein, a method of delivering a dendrimer to a cell is provided. The method comprises the step of administering a nanoparticle structure comprising a derivative of chitosan and a dendrimer to the cell. The previously described embodiments of the nanoparticle structure are applicable to the method of delivering a dendrimer to a cell described herein.

The zwitterionic chitosan derivative may be administered to a subject as an aqueous or non-aqueous solution, such as an isotonic sterile saline solution. The zwitterionic chitosan derivative may also be formulated with a pharmaceutically acceptable carrier or diluent. The specific components included in formulations comprising the zwitterionic chitosan derivative will depend on such facts as the means of administration to the subject. For example, formulations comprising the zwitterionic chitosan derivative suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. These formulations can be presented in unit-dose or multi-dose sealed containers, such as ampules and vials. Formulations comprising the zwitterionic chitosan derivative can also be presented in syringes, such as prefilled syringes.

Formulations comprising the zwitterionic chitosan derivative can be administered by a number of routes including, but not limited to oral, intravenous, intraperitoneal, intramuscular, transdermal, subcutaneous, topical, sublingual, intravascular, intramammary, or by rectal means. Formulations comprising the zwitterionic chitosan derivative can also be administered via liposomes. Such administration routes and appropriate formulations are generally known to those of skill in the art. Formulations comprising the zwitterionic chitosan derivative, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

As described herein, the step of "administering" may be accomplished by any conventional route suitable for administration of the zwitterionic chitosan derivative dendrimers of the invention to a subject, including, but not limited to, intravenous, intraperitoneal, intramuscular, subcutaneous and intradermal routes of administration. In certain aspects, administration is accomplished parenterally, e.g. injections including, but not limited to, subcutaneously or intravenously or any other form of injections or infusions.

Formulations containing dendrimers can be administered by a number of routes including, but not limited to oral, intravenous, intraperitoneal, intramuscular, transdermal, subcutaneous, topical, sublingual, intravascular, intramammary, or rectal means. Formulations containing dendrimers can also be administered via liposomes. Such administration routes and appropriate formulations are generally known to those of skill in the art. Formulations containing dendrimers, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations containing dendrimers suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations containing dendrimers can be presented in unit-dose or multi-dose sealed containers, such as ampules and vials. The formulations containing dendrimers can also be presented in syringes, such as prefilled syringes.

In various embodiments described herein, the cell is a cancer cell. In other embodiments, the nanoparticle structure releases the dendrimer to the cell. As used herein, the term "release" refers to any mechanism by which the dendrimer can be delivered to the cell or cells of interest. In some embodiments, the release occurs at an acidic pH. The term "acidic pH" is well known in the art and includes any pH value below 7.0. In some embodiments, the acidic pH is caused by hypoxia. The term "hypoxia" is well known in the art and refers to a lack of oxygen supply to a particular area, for example to a cell or to a tissue. In other embodiments, the acidic pH is caused by the Warburg effect. The Warburg effect refers to a hypothesis that most cancer cells predominantly produce energy by a high rate of glycolysis followed by lactic acid fermentation in the cytosol, rather than by a comparatively low rate of glycolysis followed by oxidation of pyruvate in mitochondria as in most normal cells.

In some embodiments described herein, the method of delivering a dendrimer to a cell results in entry of the dendrimer into the cell. In various embodiments, the entry into the cell results in apoptosis of the cell. In one embodiment, the apoptosis results from delivery of the dendrimer to the cell. In another embodiment, the apoptosis results from delivery of an agent to the cell, wherein the agent is contained within the dendrimer or covalently conjugated to the dendrimer.

In one embodiment described herein, a method of delivering a dendrimer to a cell in a subject is provided. The method comprises the step of administering an effective amount of a nanoparticle structure to the subject, wherein the nanoparticle structure comprises a derivative of chitosan and a dendrimer. The previously described embodiments of the nanoparticle structure and of the method of delivering a dendrimer to a cell are applicable to the method of delivering a dendrimer to a cell in a subject described herein.

As used herein, the "subject" refers to a mammal, such as human, a non-human primate, bird, horse, cow, goat, sheep, a companion animal, such as a dog, cat or rodent, or other mammal. In a specific aspect, the subject is a human.

As used herein, the term "effective amount" and "therapeutically effective amount" refers to an amount which gives the desired benefit or therapeutic effective to a subject and includes both treatment, prophylactic, and preventative administration. The amount will vary from one subject to another and will depend upon a number of factors, including the overall physical condition of the subject, it identity of the disease or condition to be treated, and the underlying cause of the condition to be treated. The amount of zwitterionic chitosan derivative or dendrimer used for therapy gives an acceptable rate of change and maintains desired response at a beneficial level. An effective amount or therapeutically effective amount of the zwitterionic chitosan derivative and dendrimers may be readily ascertained by one of ordinary skill in the art using publicly available materials and procedures.

In some aspects, the effective or therapeutically effective amount of the zwitterionic chitosan derivative administered to a subject ranges between about 1 and 5000 mg/kg body weight of the subject. Other suitable ranges include, but are not limited to, about 100 and 4000 mg/kg, about 200 and 3000 mg/kg, about 300 and 2000 mg/kg, about 400 and 1200 mg/kg, about 500 and 1100 mg/kg, and about 600 and 1000 mg/kg. Specific suitable amounts include about 400 mg/kg, about 500 mg/kg, about 600 mg/kg, about 700 mg/kg, about 800 mg/kg, about 900 mg/kg, about 1000 mg/kg, about 1100 mg/kg, and about 1200 mg/kg.

In various embodiments described herein, the cell is associated with a tumor in the subject. In other embodiments, the tumor is a solid tumor. The terms "tumor" and "solid tumor" are well understood in the art of oncology.

In one embodiment described herein, a method of delivering an agent to a subject is provided. The method comprises the step of administering a nanoparticle structure to the subject, wherein the nanoparticle structure comprises a derivative of chitosan, a dendrimer, and the agent. The previously described embodiments of the nanoparticle structure, of the method of delivering a dendrimer to a cell, and of the method of delivering a dendrimer to a cell in a subject are applicable to the method of delivering an agent to a subject described herein.

In some embodiments described herein, the agent is contained within the dendrimer or covalently conjugated to the dendrimer. In other embodiments, the agent is delivered to a cell in the subject. In one embodiment, the agent is a pharmaceutical compound. In another embodiment, the pharmaceutical compound is an anticancer drug. In yet another embodiment, the agent is an imaging agent. The phrases "pharmaceutical compound," "anticancer drug," and "imaging agent" are well understood in the art. For example, a "pharmaceutical compound" refers to a substance used as a medication according to the Food, Drug and Cosmetic Act. The term "anticancer agent" includes any agent that exhibits anti-tumor activity. Such agents include, without limitation, chemotherapeutic agents (i.e., a chemical compound or combination of compounds useful in the treatment of cancer), anticancer antibodies, agents that disrupt nucleic acid transcription and/or translation, such as antisense oligonucleotides, small interfering RNA (siRNA), and the like. The term "imaging agent" refers to a compound that is capable of localizing selectively at sites of diagnostic interest in vivo such as at a particular organ, tissue or cell type.

In one embodiment described herein, a polymer is provided. The polymer comprises a derivative of chitosan, wherein the derivative is zwitterionic. The previously described embodiments of the nanoparticle structure with respect to the derivative of chitosan are applicable to the polymer described herein.

In one embodiment described herein, a method of suppressing an inflammatory response in a subject is provided. The method comprises the step of administering an effective amount of a polymer to the subject, wherein the polymer comprises a zwitterionic derivative of chitosan. The previously described embodiments of the polymer are applicable to the method of suppressing an inflammatory response in a subject described herein.

In various embodiments described herein, the inflammatory response may be associated with activated macrophages in the subject. The phrase "activated macrophage" is well known in the art, and includes cells that secrete inflammatory mediators and target and/or kill intracellular pathogens in the subject. In some embodiments, the inflammatory response is pro-inflammatory cytokine production. Pro-inflammatory cytokines are well known in the field of immunology and include, but are not limited to, Interleukin-1β (IL-1β), interleukin-6 (IL-6), interleukin-12 (IL-12), interferon-γ (IFN-γ), and tumor necrosis factor alpha (TNF-α). In one embodiment, the cytokine production is IL-6 production. In another embodiment, the cytokine production is TNF-α production.

In some embodiments, the inflammatory response is pro-inflammatory chemokine production. Pro-inflammatory chemokines are well known in the art of immunology. In one embodiment, the chemokine production is Macrophage inflammatory protein 2 (MIP-2) production.

In one embodiment described herein, a method of suppressing cytokine or chemokine production in a subject is provided. The method comprises the step of administering an effective amount of a polymer to the subject, wherein the polymer comprises a zwitterionic derivative of chitosan. The previously described embodiments of the polymer and of the method of suppressing an inflammatory response in a subject are applicable to the method of suppressing cytokine or chemokine production in a subject described herein.

In various embodiments, the cytokine or chemokine production is associated with activated macrophages. In some embodiments, the cytokine or chemokine production is induced by lipopolysaccharide (LPS). The term "lipopolysaccharide" is well known in the art, and refers to a molecule in which lipids and polysaccharides are linked, for example a component of the cell wall of gram-negative bacteria. In some embodiments, the polymer binds directly to the LPS.

In one embodiment described herein, a method of binding a lipopolysaccharide is provided. The method comprises the step of contacting the lipopolysaccharide with a polymer comprising a zwitterionic derivative of chitosan. The previously described embodiments of the polymer, of the method of suppressing an inflammatory response in a subject, and of the method of suppressing cytokine or chemokine production in a subject are applicable to the method of binding a lipopolysaccharide described herein.

In one embodiment described herein, a method of decreasing a bacterial toxin in a subject is provided. The method comprises the step of administering an effective amount of a polymer to the subject, wherein the polymer comprises a zwitterionic derivative of chitosan. The previously described embodiments of the polymer, of the method of suppressing an inflammatory response in a subject, and of the method of suppressing cytokine or chemokine production in a subject are applicable to the method of decreasing a bacterial toxin in a subject described herein.

In various embodiments, the bacterial toxin is an endotoxin. As used herein, the term "endotoxin" refers to a toxin that is present inside a bacterial cell (for example, a cell wall) and is released when the cell is broken down (e.g., dies).

In one embodiment described herein, a method of decreasing a bacterial toxin in a composition is provided. The method comprises the step of administering an effective amount of a polymer to the composition, wherein the polymer comprises a zwitterionic derivative of chitosan. The previously described embodiments of the polymer, of the method of suppressing an inflammatory response in a subject, of the method of suppressing cytokine or chemokine production in a subject, and of decreasing a bacterial toxin in a subject are applicable to the method of decreasing a bacterial toxin in a composition described herein.

In some embodiments, the composition is a pharmaceutical composition. In other embodiments, the composition is water.

While the invention has been illustrated and described in detail in the foregoing description, such an illustration and description is to be considered as exemplary and not restrictive in character, it being understood that only the illustrative embodiments have been described and that all changes and modifications that come within the spirit of the invention are desired to be protected. Those of ordinary skill in the art may readily devise their own implementations that incorporate one or more of the features described herein, and thus fall within the spirit and scope of the present invention.

EXAMPLE 1

Formation and Properties of Chitosan and Chitosan Derivatives

Synthesis of Zwitterionic Chitosan Derivatives and other Chitosans

In this example, chitosan derivatives were formed and analyzed. In particular, a zwitterionic chitosan (ZWC) derivative was synthesized. Briefly, low-molecular-weight chitosan (LMCS; MW: 15 kDa; degree of deacetylation: 87%; Polysciences) was first dissolved in 1% acetic acid to obtain an acetate salt form. LMCS acetate 200 mg was dissolved in 30 mL of deionized water. Succinic anhydride was added as solid to the LMCS solution under vigorous stirring varying the quantities according to the desired molar feed ratio of anhydride to amine (An/Am ratio). The pH of the reaction mixture was maintained at 6-6.5 and subsequently increased to 8-9 with 1 N NaHCO$_3$ After an overnight reaction at room temperature under stirring, the reaction mixture was dialyzed against water (molecular weight cutoff: 3500) maintaining the pH at 8-9 with 1 N NaOH. The purified ZWC was freeze-dried and stored at −20° C.

Chitosan Properties

All chitosan and chitosan derivatives showed pH-dependence in aqueous solubilities and corresponding charge profiles (see FIG. 1). Solutions of chitosan glutamate and LMCS (10 mg/mL) became turbid at pH above 6.5 reaching the maximum turbidity at pH 8, where they had neutral charges. On the other hand, ZWC (10 mg/mL) formed clear solutions at both acidic and basic pHs, indicating aqueous solubility, except at the pI value. The pI value of ZWC decreased with the increase of the An/Am ratio (see FIG. 1). Glycol chitosan was similar to chitosan glutamate and LMCS in that it showed neutral charges around pH 8, but the solution (10 mg/mL) was not turbid. This suggests the aqueous solubility of glycol chitosan.

A summary of chitosan and various chitosan derivatives (collectively referred to as "chitosans") is provided in Table 1

TABLE 1

Properties of Various Chitosans

| | Description | Molecular Weight | Degree of deacetylation (primary amine content) | Aqueous solubility at pH 7.4 |
|---|---|---|---|---|
| Chitosan glutamate | Glutamate salt form | 200 kDa | 75-90% | Insoluble |
| Glycol chitosan | 2-hydroxyethylether derivative of chitosan | 82 kDa | 83% | Soluble |
| LMCS | Parent of ZWC | 15 kDa | 87% | Insoluble |
| ZWC Derivative (An/Am = 0.3) | <29%$^b$ | ~15 kDa | >58% | Soluble |
| ZWC Derivative (An/Am = 0.7) | >52 | ~15 kDa | <35% | Soluble |

EXAMPLE 2

In Vivo Properties of Chitosan and Chitosan Derivatives

In Vivo Biocompatibility and Gross Tissue Responses to Intraperitoneally Administered Chitosans Chitosan glutamate, glycol chitosan, and ZWC were tested for tissue responses following IP administration (800 mg/kg). Chitosan and buffer controls (phosphate buffered saline (PBS), pH 7.4, or glutamate buffer, pH 5) were sterilized by aseptic filtration. Chitosan solutions (20 mg/mL) were prepared by dissolving chitosan glutamate in water or glycol chitosan and ZWC in PBS. ICR mice (25 g) (Harlan, Indianapolis, Ind.) were anesthetized with subcutaneous injection of ketamine 50 mg/kg and xylazine 10 mg/kg. A 0.5 cm skin incision was made in the skin 0.5 cm above the costal margin, and the peritoneum was nicked with a 24-gauge catheter. One milliliter of 20 mg/mL chitosan solutions or control buffers were injected into the peritoneal cavity through the catheter, and the skin was closed with suture.

The animals were sacrificed after 7 days to evaluate the presence of residues, tissue adhesions, and visible signs of inflammation (nodules, increased vascularization) in the peritoneal cavity. Liver and spleen were sampled for histology, and the peritoneal fluid was sampled on a slide for cytological analysis. After fixation in 10% formalin, the sectioned organ samples and peritoneal fluid cells were stained with hematoxylin and eosin (H&E).

Figure 2:
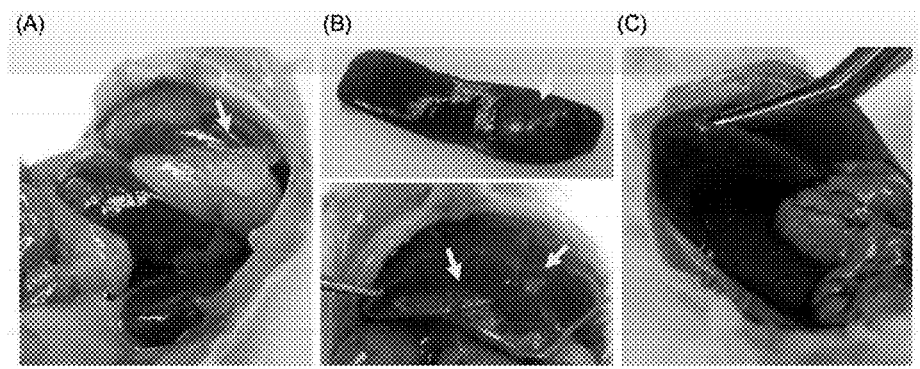
FIG. 2 shows chitosan precipitates (arrows) in the peritoneal cavity. Mice injected with chitosan glutamate intraperitoneally were examined 7 days after injection. (A) Chitosan precipitates found between the liver and the stomach. Chitosan precipitates stuck on the spleen (B) and the liver (D). (C) Lobes of the liver were connected via chitosan residue.

Upon necropsy, the organs of animals treated with ZWC or glycol chitosan were grossly normal. No material was found in the peritoneal cavity of the mouse injected with glycol chitosan or ZWC. On the other hand, white chitosan precipitates were seen in all mice injected with chitosan glutamate due to the near-neutral pH of the peritoneal fluid (see FIG. 2A). The white precipitates were usually present on the liver and spleen (see FIG. 2B). In 3 out of 4 cases, lobes of the liver were connected via the residual materials (see FIG. 2C).

Histological and Cytological Evaluation

Biomaterials delivered to peritoneal cavity often cause inflammatory responses followed by adhesion formation between in peritoneal tissues and abdominal walls. Once entering systemic circulation, they can also cause abnormalities in filtering organs. To estimate the destination and effect of IP chitosan, peritoneal fluid and organs as well as abdominal wall were microscopically examined. Incidence of lesions in peritoneal tissues is summarized in Table 2.

TABLE 2

Incidence of lesions in tissues after intraperitoneal injection of chitosans and buffers.

|  | PBS | Chitosan glutamate | Glycol chitosan | ZWC Derivative (An/Am = 0.7) | Glutamate buffer |
|---|---|---|---|---|---|
| Liver, capsule inflammation | 0/2[a] | 4/4 | 0/4 | 0/5 | 0/3 |
| Liver, capsular chitosan deposits | 0/2 | 4/4 | 0/4 | 0/5 | 0/3 |
| Spleen, capsule inflammation | 0/2 | 3/4 | 0/4 | 0/5 | 0/3 |
| Spleen, capsular chitosan deposits | 0/2 | 3/4 | 0/4 | 0/5 | 0/3 |
| Body wall, inflammation | 0/2 | 3/4 | 1/4 | 0/5 | 0/3 |
| Body wall, chitosan deposits | 0/2 | 0/4 | 0/4 | 0/5 | 0/3 |
| Peritoneal fluid, inflammation | 0/2 | 4/4 | 3/3 | 0/5 | 0/4 |
| Peritoneal fluid, chitosan deposits | 0/2 | 4/4 | 3/3 | 0/5 | 0/4 |

[a]Incidence of occurrence: Number of mice with lesion/total number of mice examined.

Figure 3:
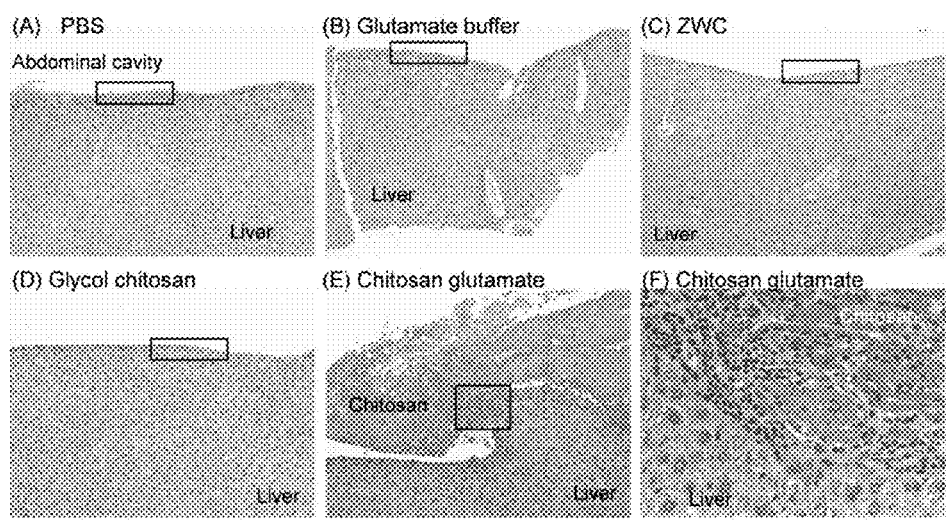
FIG. 3 shows hematoxylin and eosin staining of liver sections of different treatment groups. (A) PBS (100×); (B) Glutamate buffer (100×); (C) ZWC (100×); (D) Glycol chitosan (100×). (A-D) Normal capsular surface (box). (E) Chitosan glutamate (100×): capsular surface of liver markedly thickened with precipitates of chitosan, which are surrounded by chronic inflammation and mild fibrosis (box). (F) Chitosan glutamate (400×): precipitates of chitosan on the liver surface surrounded by macrophages, fibroblasts, and neutrophils.

In mice injected with PBS, glutamate buffer, and ZWC, no significant microscopic differences were seen in the liver (see FIGS. 3A, 3B, and 3C), spleen, and abdominal wall. One mouse treated with glycol chitosan had mild inflammation of the body wall, but liver (see FIG. 3D) and spleen were normal. Peritoneal tissues from other mice in this group were unremarkable. In contrast, mice treated with chitosan glutamate had noticeable chitosan precipitates on the liver, spleen and abdominal wall, which were surrounded by macrophages and neutrophils (see FIGS. 3E and 3F). Capsular surface of the liver adjacent to precipitates of chitosan was thickened and mildly fibrotic (see FIGS. 3E and 3F).

Figure 4:
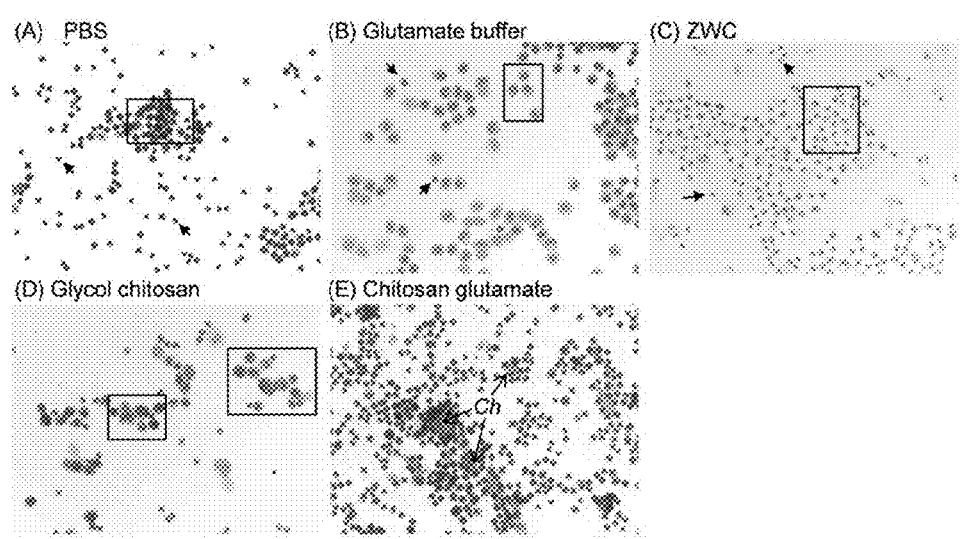
FIG. 4 shows the cytology of the peritoneal fluid from different treatment groups using hematoxylin and eosin staining. (A) PBS; (B) Glutamate buffer; (C) ZWC. (A-C) Peritoneal fluid composed of small macrophages (box) and lymphocytes (arrows). No chitosan precipitates were identified. (D) Glycol chitosan: peritoneal fluid is composed of large macrophages (box) containing chitosan. (E) Chitosan glutamate: peritoneal fluid composed of large macrophages with intracellular eosinophilic chitosan. Extracellular chitosan (Ch) is surrounded by numerous macrophages. All images are of 400× magnification.

No abnormality was observed in peritoneal fluid of the animals injected with PBS, glutamate buffer, or ZWC (see FIGS. 4A, 4B, and 4C). However, chitosan precipitates were detected in peritoneal macrophages in mice treated with glycol chitosan (see FIG. 4D) or chitosan glutamate (see FIG. 4E). Chitosan glutamate was also observed as extracellular residues, surrounded by large activated macrophages (see FIG. 4E). No chitosan precipitates were observed in those treated with ZWC (see FIG. 4C).

EXAMPLE 3

Chitosan Effect on Macrophage Proliferation

In an attempt to understand the difference in IP responses to chitosan glutamate, glycol chitosan, and ZWC, in vitro proliferation of peritoneal macrophages was evaluated in the presence of the three chitosans. Peritoneal macrophages were chosen because they are prevalent in the peritoneal cavity and likely to be an important player in inflammatory responses to IP injected chitosans. Mouse peritoneal macrophages were maintained in Dulbecco's Modified Eagle Medium (DMEM) supplemented with 5% fetal bovine serum and 5 mM HEPES. Cells were seeded in 24 well plates at a density of 50,000 cells per well in 1 mL culture medium. After overnight incubation, chitosan solutions (2 or 20 mg/mL) were added to make a final concentration of the medium 0.2 or 2 mg/mL. PBS and lipopolysaccharide (LPS) (1 µg/mL) were added in control groups. MTT assay was performed after 24 hours of incubation to determine the effects of chitosans on macrophage proliferation.

Figure 5:
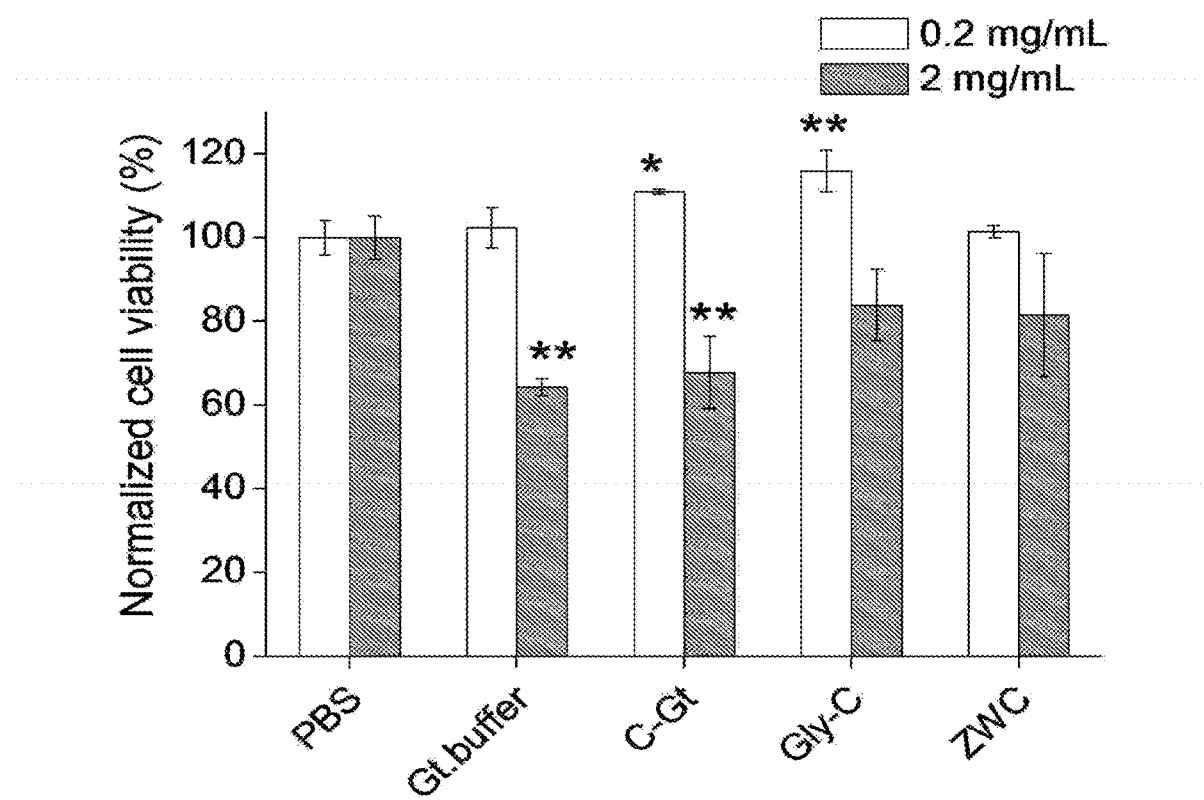
FIG. 5 shows the viability of mouse peritoneal macrophages in the presence of ZWC (An/Am ratio=0.7), chitosan glutamate (C-Gt) and glycol chitosan (Gly-C). Data are expressed as averages with standard deviations of three repeated measurements. *: $p<0.05$; **: $p<0.01$ vs PBS.

For all chitosans, 0.2 mg/mL of chitosan treatment did not negatively influence the macrophage proliferation (see FIG. 5). At 2 mg/mL, there was a moderate reduction in macrophage proliferation with chitosan glutamate ($p<0.01$ vs. PBS). Glutamate buffer (pH 5) added in an equivalent volume showed a similar level of decrease in cell proliferation, indicating that this reduction might be partly due to the acidity of the medium. Neither glycol chitosan nor ZWC significantly reduced the macrophage proliferation at 2 mg/mL.

EXAMPLE 4

Cytokine Release from Peritoneal Macrophages Induced by Chitosans

To investigate whether each chitosan had an intrinsic ability to activate peritoneal macrophages, naïve (non-challenged) peritoneal macrophages were incubated with different chitosans (2 mg/mL), and the medium was analyzed to determine the concentrations of pro-inflammatory cytokines (IL-1β, TNF-α, IL-6 and MIP-2). In this experiment, LMCS, the parent material for ZWC, was also tested.

Peritoneal macrophages were seeded in 24-well plates at a density of 150,000 cells per well in 1 mL of medium. After overnight incubation, 100 µL of the chitosan solution was added to each well to bring the final chitosan concentration in medium to 2 mg/mL. In control groups, 100 µL of PBS or glutamate buffer (pH 5) was added in lieu of chitosan solutions. After 24 hour incubation, the culture media were centrifuged at 2000 rpm for 10 min to separate supernatants. The concentrations of interleukin (IL)-1β, IL-6, tumor necrosis factor (TNF)-α, and macrophage inflammatory protein (MIP)-2 in the supernatant were determined using a Milliplex Multi-Analyte Profiling (MAP) cytokine/chemokine panel (Millipore, Billerica, Mass.).

In another set of experiments, macrophages were first challenged by adding LPS to the media in the final concentration of 1 µg/mL shortly before the chitosans or buffer controls. For selected samples, enzyme-linked immunosorbent assay (ELISA) was performed to determine the MIP-2 levels using an MIP-2 ELISA kit (R&D systems, Minneapolis, Minn.). The detection range of MAP panel was 0-10,000 pg/mL for all analytes. For MIP-2 ELISA, standard curves were prepared in the range of 0-667 pg/mL. In both assays, the supernatant collected from LPS-challenged macrophages was always diluted 10 times prior to the analysis.

To investigate the time course of the ZWC effect on cytokine production, ZWC or LMCS was added in the final concentration of 2 mg/mL at 0, 2, 4, or 8 hours after the LPS addition. After incubating with chitosans for 24 hours, the culture media were collected and diluted 10 times, and the MIP-2 levels were determined using ELISA. For comparison, another set of macrophages was challenged with LPS and incubated for 0, 2, 4, 8, or 24 hours, and the media were sampled without any treatment or further incubation.

Briefly, 10 µg of LPS was mixed with 20 mg of ZWC in 1 mL of 0.9% NaCl and incubated at room temperature for 1 hour. The ratio of LPS to ZWC (10 µg per 20 mg) was consistent with the ratio used in prior experiments (1 µg per 2 mg). ZWC was then precipitated by decreasing the solution pH to 4.8 with 0.1-1 M HCl and removed by 15-min centrifugation at 10,000 rpm. Assuming that the LPS was present in the supernatant, a volume equivalent to 1 µg of LPS was sampled and added to 1 mL of peritoneal macrophage culture. After overnight incubation, MIP-2 levels in the culture media were determined using ELISA.

Figure 6:
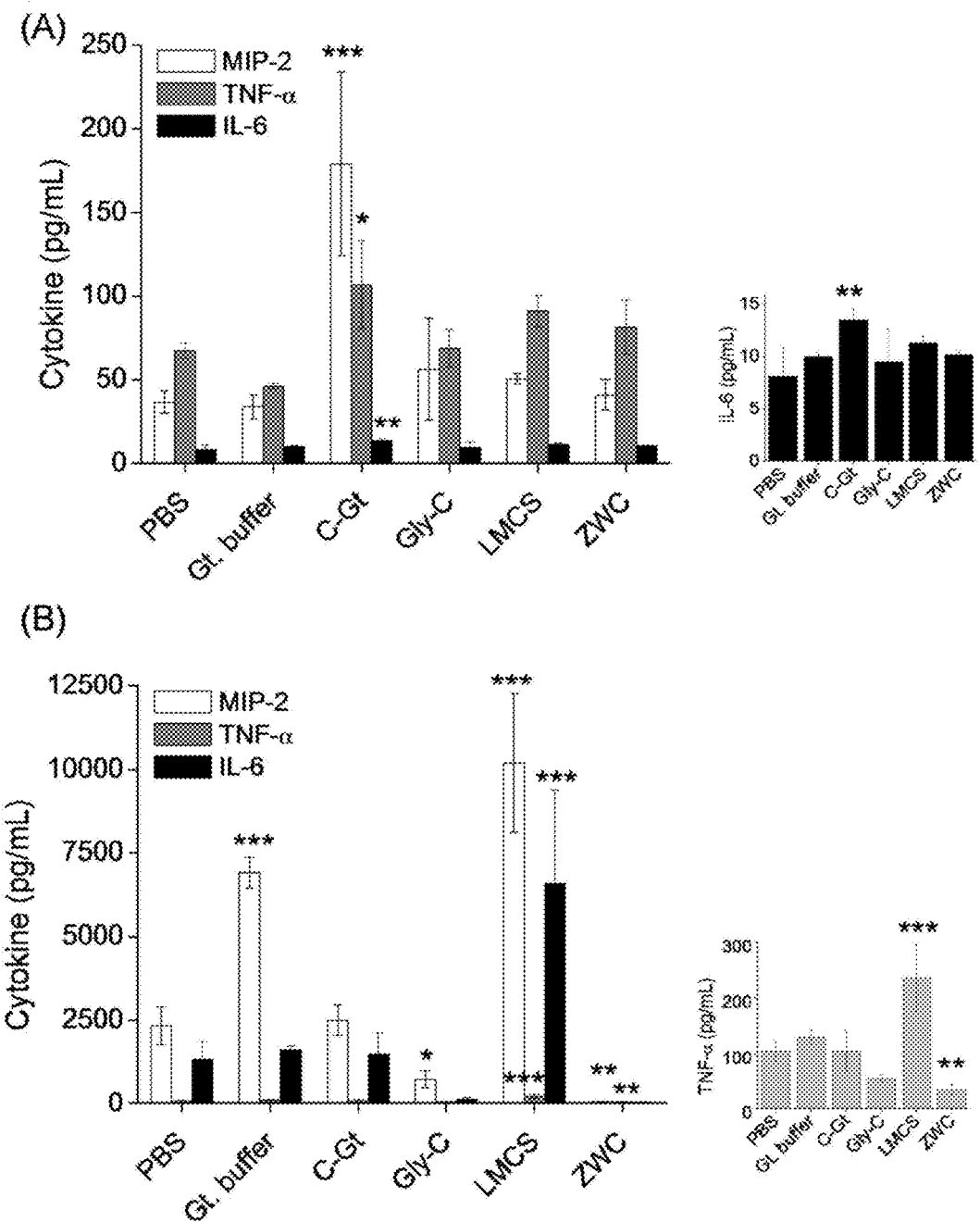
FIG. 6 shows the effect of chitosan treatment (all in 2 mg/mL) on the levels of proinflammatory cytokines released from (A) naïve mouse peritoneal macrophages and (B) LPS-challenged macrophages. Cytokine levels are determined by Milliplex Multi-Analyte Profiling cytokine/chemokine panel. Media of the LPS-challenged macrophages were 10 times diluted prior to analysis. Graphs on the right are displayed in narrow y-scales. ZWC (An/Am=0.7); C-Gt: chitosan glutamate; Gly-C: glycol chitosan. Data are expressed as averages with standard deviations of three repeated measurements. *: $p<0.05$; : $p<0.01$; *: $p<0.001$ vs PBS.

To investigate whether each chitosan had an intrinsic ability to activate peritoneal macrophages, naïve (non-challenged) peritoneal macrophages were incubated with different chitosans (2 mg/mL), and the medium was analyzed to determine the concentrations of pro-inflammatory cytokines (IL-1β, TNF-α, IL-6 and MIP-2). In this experiment, LMCS, the parent material for ZWC, was also tested. Naïve macrophages treated with PBS produced 37±7 pg/mL of MIP-2, 67±5 pg/mL of TNF-α, and 8±3 pg/mL of IL-6, which were considered basal levels of cytokines. There was no additional cytokine release in those treated with glutamate buffer, glycol chitosan, LMCS, and ZWC. There was no difference between LMCS and ZWC-treated groups. On the other hand, chitosan glutamate treatment resulted in significant increases in the levels of MIP-2 ($p<0.001$), TNF-α ($p<0.05$), and IL-6 ($p<0.01$), as compared with PBS-treatment (see FIG. 6A).

To investigate how each chitosan influenced the cytokine production in activated macrophages, the cells were first challenged with LPS, a potent inducer of cytokine release, prior to the addition of chitosans (2 mg/mL). LPS-challenged, then PBS-treated macrophages produced 2341±564 pg/mL of MIP-2, 106±18 pg/mL of TNF-α, and 1346±535 pg/mL of IL-6 (see FIG. 6B). Glutamate buffer caused increase in MIP-2 production, whereas chitosan glutamate did not have any influence. LMCS treatment increased production of all three cytokines from the LPS-challenged macrophages. Interestingly, ZWC caused a marked decrease in the LPS-induced production of MIP-2 ($p<0.01$) and TNF-α ($p<0.01$) as compared with PBS. Glycol chitosan also decreased the production of MIP-2 as compared to PBS. Chitosan treatment did not cause any change in IL-10β levels in either naïve or LPS-challenged macrophages.

EXAMPLE 5

MIP-2 Induction by Chitosans with a Varying Number of Amine Groups

Figure 7:
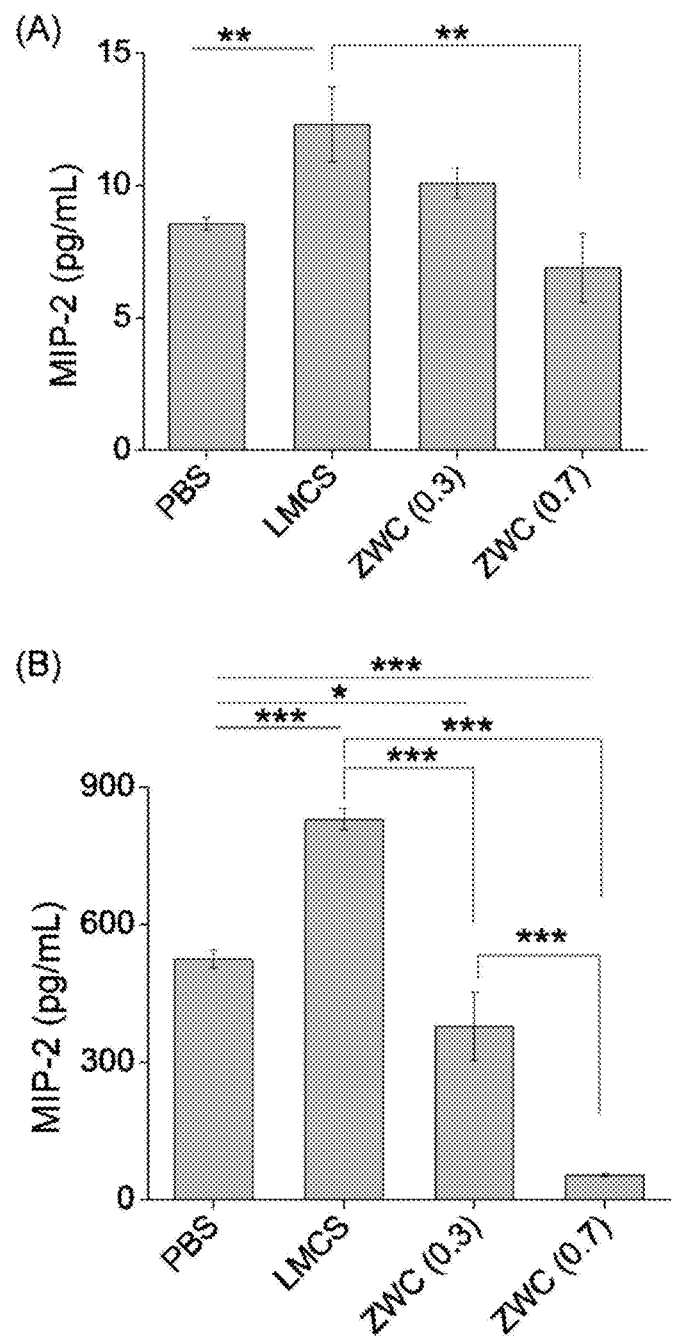
FIG. 7 shows the effect of chitosan treatment (all in 2 mg/mL) on the MIP-2 production from (A) naïve mouse peritoneal macrophages and (B) LPS-challenged macrophages. MIP-2 level is determined by ELISA. Media of the LPS-challenged macrophages were 10 times diluted prior to analysis. Data are expressed as averages with standard deviations of three repeated measurements. : $p<0.01$; *: $p<0.001$.

The effects of chitosans on MIP-2 release from naïve or LPS-challenged macrophages were monitored varying the amine content in the chitosan. LMCS and ZWC were compared with different An/Am ratios (0.3 or 0.7), all at 2 mg/mL, with respect to the ability to induce macrophages to produce MIP-2, the most sensitive response in the prior experiment. From naïve macrophages, LMCS induced a higher level of MIP-2 than PBS ($p<0.01$), but no significant change was observed after ZWC treatment (see FIG. 7A). In LPS-challenged macrophages, LMCS significantly increased the MIP-2 level ($p<0.001$). In contrast, the two ZWCs suppressed MIP-2 production from the LPS-challenged macrophages ($p<0.001$ for An/Am: 0.7, $p<0.05$ for An/Am 0.3 vs. PBS) (see FIG. 7B). ZWC (An/Am: 0.7) decreased the LPS-induced MIP-2 production to a greater extent than ZWC (An/Am: 0.3).

MIP-2 levels measured by ELISA were not identical to the values determined with the MAP panel, most likely due to the difference between the two assay methods in the sensitive detection ranges. However, results of the two assays were consistent in that MIP-2 levels from LPS-challenged macrophages were at least two orders of magnitude higher than those of naïve macrophages and that the MIP-2 production from the LPS-challenged macrophages was significantly reduced by the ZWC treatment.

EXAMPLE 6

Onset of ZWC Derivative Effect on LPS-induced MIP-2 Production

To confirm the ability of ZWC to prevent LPS-induced cytokine production and examine the onset of the action, macrophages were first challenged with LPS for 0, 2, 4, or 8 hours. Subsequently, ZWC or LMCS were added to the challenged macrophages, followed by incubation for additional 24 hours.

Figure 8:
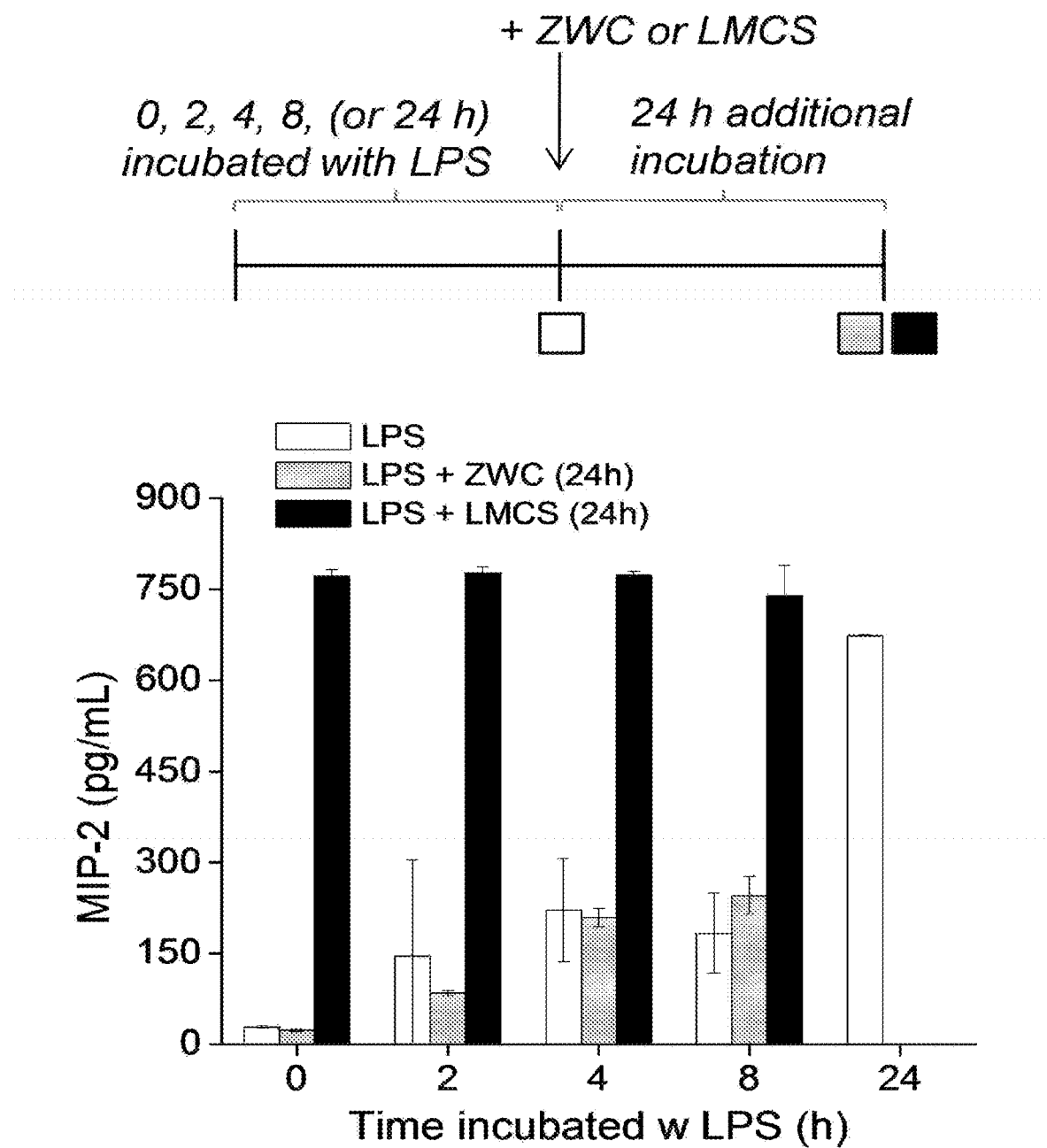
FIG. 8 shows the effect of timed application of ZWC or LMCS (all in 2 mg/mL) on MIP-2 production in the LPS-challenged macrophages. Mouse peritoneal macrophages were incubated with LPS for 0, 2, 4, 8, or 24 hours, and the culture medium was sampled for determination of the MIP-2 level (white bars). In another set, macrophages were incubated with LPS for 0, 2, 4, or 8 hours with LPS and then treated with ZWC or LMCS, and the media were sampled after 24 hours (grey or black bars). Data are expressed as averages with standard deviations of three repeated measurements.

In ZWC-treated macrophages, the MIP-2 levels in the culture media were comparable to those sampled prior to ZWC treatment (see FIG. 8). This result shows that cytokine production was completely blocked from the time ZWC was added to the medium, and proliferating cells did not further produce cytokines. In contrast, LMCS-treated macrophages continued to produce MIP-2, resulting in the same level as those grown for 24 hours without any other treatment after LPS challenge.

EXAMPLE 7

LPS Inactivation by ZWC Derivative

To investigate how ZWC prevented the MIP-2 production from the LPS-challenged macrophages, LPS was incubated with ZWC for 1 hour before it was given to the macrophages. ZWC was removed by precipitation at pH 4.8 (~pI of ZWC) at the end of the 1-h incubation so that the direct effect of ZWC on the cells could be excluded.

Figure 9:
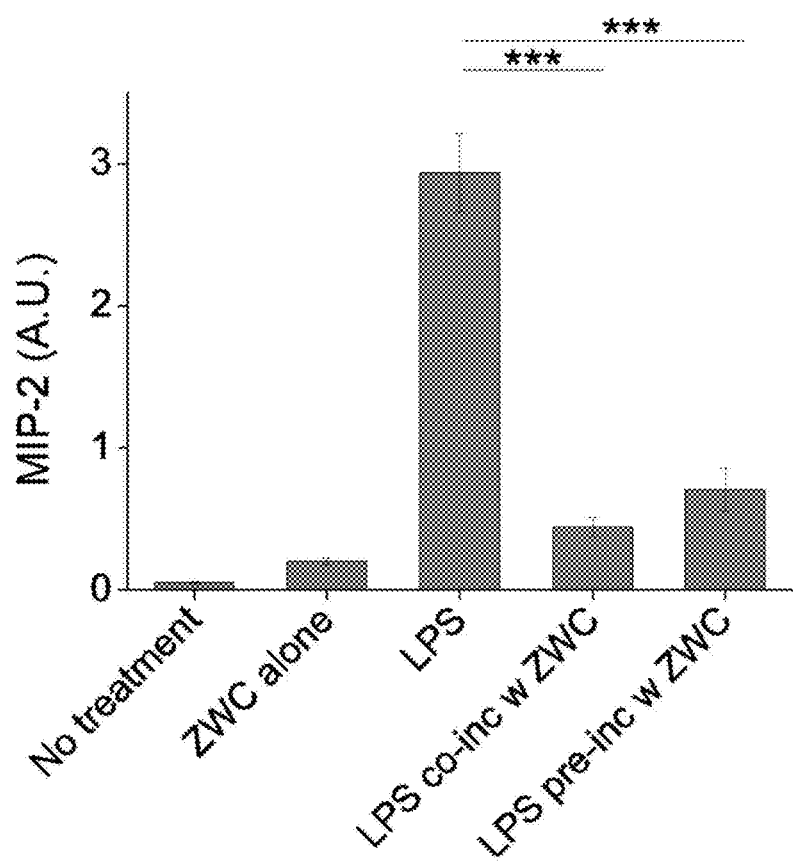
FIG. 9 shows production from macrophages incubated with ZWC (2 mg/mL), LPS (1 µg/mL), a mixture of LPS (1 µg/mL) and ZWC (2 mg/mL) (LPS co-inc w ZWC), or LPS pre-incubated with ZWC (equivalent to 1 µg/mL LPS under an assumption that all the LPS remained in the supernatant; LPS pre-inc w ZWC). ELISA was performed on 10 times-diluted culture media. Data are expressed as averages with standard deviations of three repeated measurements. ***: $p<0.001$.

FIG. 9 shows that the LPS-induced MIP-2 production was reduced when ZWC coexisted in the culture, consistent with prior experiments. The LPS pre-treated with ZWC also lowered the MIP-2 production to a comparable level. This result suggests that the reduction in MIP-2 production was due to the inactivation of LPS by ZWC rather than a direct effect of ZWC on the LPS-challenged cells. A similar trend was observed with LPS pre-incubated at a higher ratio of LPS to ZWC (30 μg LPS per 20 mg ZWC). Further increase of LPS (40 μg LPS per 20 mg ZWC) resulted in a significant production of MIP-2, indicating that there was an upper limit of LPS that a fixed amount of ZWC could inactivate.

EXAMPLE 8

Analysis of Endotoxins Using Chitosans

Biological activity of chitosan may be attributed to the positive charges carried by the amine groups, which can electrostatically interact with cell membranes or circulating plasma proteins and lead to platelet adhesion/activation and thrombus formation. Due to the ability to interact with serum proteins, chitosans activate macrophages and induce cytokine production. Chitosan derivatives with reduced positive charge densities cause much lower platelet adhesion and aggregation than original chitosan. Aqueous solubility of chitosan in physiological pH is also expected to play a role in biological responses, because chitosan precipitates can be subjected to phagocytic uptake and further stimulate macrophages. Therefore, it was hypothesized that the good hemocompatibility of ZWC and the lack of pro-inflammatory effect might be related to the reduced amine contents of ZWC and/or the aqueous solubility at neutral pH.

The amount of endotoxin present in each chitosan was determined by the kinetic turbidometric Limulus Amebocyte Lysate (LAL) assay at Associates of Cape Cod Inc. (East Falmouth, Mass.). Chitosan samples were initially prepared as 1 mg/mL (ZWC, LMCS) or 10 mg/mL (chitosan glutamate, glycol chitosan) solutions in LAL reagent water (LRW) and then serially diluted from 1:20 to 1:8000 to find the minimum concentration that did not interfere with analysis. $E.\ coli$ 0113:H10 was used as a control standard endotoxin and serially diluted from 0.32 to 0.002 EU/mL to construct a calibration curve. Positive product controls were prepared in parallel by fortifying the diluted samples with additional endotoxin equivalent to 0.008 EU/mL. LRW was tested as a negative control and found to contain less than the lowest concentration of the calibration curve (0.002 EU/mL). Pyrotell®-T LAL lysate was reconstituted with Glucashield buffer, a β-glucan inhibiting buffer, and mixed with samples or controls in a 1:1 ratio in a depyrogenated microplate. The absorbance of each well was monitored over time. The time required for the absorbance to increase significantly over background was defined as the onset time. The correlation coefficient for the regression of log of onset time vs. log of endotoxin concentration was ≥0.98. All samples were tested in duplicate. The results were reported as the amount of endotoxin present in each chitosan (EU/g).

TABLE 3

Endotoxin levels in chitosans

| Sample | Endotoxin concentration (EU/g) |
| --- | --- |
| Chitosan glutamate | 247 |
| Glycol chitosan | 311 |
| LMCS | 311 |
| ZWC Derivative(An/Am = 0.3) | 6,860 |
| ZWC Derivative (An/Am = 0.7) | 14,150 |

The levels were comparable among chitosan glutamate, glycol chitosan, and LMCS. However, endotoxin levels in ZWC derivative were one or two orders of magnitude higher than those of other chitosans. ZWC derivative with An/Am ratio 0.7 had highest endotoxin concentration. This result suggests a relatively high affinity of ZWC derivative to endotoxin.

Chitosans have been shown to induce production of pro-inflammatory cytokines or chemokines from macrophages. To examine if ZWC and glycol chitosan were intrinsically less bioactive than other chitosans, the secretion of IL-10, IL-6, TNF-α, and MIP-2 (murine functional homologue of IL-8) from peritoneal macrophages was then monitored after treating with different chitosans. These cytokines or chemokines are responsible for both local and systemic inflammatory responses and have been used in evaluating the safety of other chitosan based formulations. Production of MIP-2, IL-6, and TNF-α in naïve macrophages was increased by treatment with chitosan glutamate but not with glycol chitosan, ZWC, or LMCS (see FIG. 6A). Chitosan glutamate is not particularly more cytotoxic than others; therefore, the difference is unlikely due to the chemotactic effect of dead cells.

The relatively high molecular weight of chitosan glutamate (200 kDa), as compared to glycol chitosan (82 kDa), ZWC (15 kDa), and LMCS (15 kDa), may account for the relatively high pro-inflammatory effect of chitosan glutamate both in vivo and in vitro. The effect of the primary amine content on the intrinsic pro-inflammatory potential of chitosan is not readily apparent from the MAP panel assay given the lack of difference between ZWC and LMCS (see FIG. 6A). ELISA detects a correlation between MIP-2 production and the amine content (LMCS>ZWC (An/Am=0.3)>ZWC (An/Am=0.7)), but the levels of MIP-2 are close to the basal level in all cases (see FIG. 7A). According to these results, ZWC and glycol chitosan have relatively low potential to cause inflammatory reactions in the peritoneal cavity by themselves, and this property can be explained by their aqueous solubility and relatively low molecular weights.

Additionally, chitosan could be administered to tissues with lesions that attract activated macrophages. Interestingly, Interestingly, only ZWC suppressed the cytokine production from LPS-challenged macrophages significantly (see FIGS. 6B and 7B). Timed application of ZWC revealed that MIP-2 production stopped as soon as ZWC was applied (see FIG. 8).

It is hypothesized that ZWC derivative may tightly bind to LPS and inactivate it, as evidenced by the fact that LPS pre-incubated with ZWC derivative lost the ability to induce MIP-2 (see FIG. 9). Moreover, ZWC derivatives show much higher endotoxin content than other chitosans, further suggesting that ZWC derivative has high affinity to LPS. The ZWC derivative-mediated inactivation of LPS appears to be potent and irreversible, given that ZWC derivative with such high endotoxin content did not activate naïve macrophages or induce inflammatory responses in vivo. MIP-2 production from the LPS-challenged macrophages decreased in the order of LMCS, ZWC derivative (An/Am=0.3), and ZWC derivative (An/Am=0.7) (see FIG. 7B), indicating that this ability may be related to the amine content (inversely proportional to the amidation degree, An/Am ratio) in chitosan.

EXAMPLE 9

Formation and Properties of Chitosans, Chitosan Derivatives, and Nanoparticle Structures Synthesis of ZWC Derivative In this example, ZWC derivative was synthesized according to the following method. In short, chitosan acetate was suspended in deionized (DI) water, and succinic anhydride was added to the chitosan mixture while stirring. After an overnight reaction, the solution was dialyzed (molecular-weight cut off: 3500 Da) against water maintaining a pH between 10 and 11, and the purified ZWC derivative was lyophilized. ZWC derivative was re-suspended in deionized water (DI water) and reacted with 30% $H_2O_2$ under vigorous stirring for 1 h at room temperature to produce a lower molecular-weight ZWC derivative. The reaction was quenched by the addition of methanol, and the resulting solution was purified by dialysis. The purified product was lyophilized and stored at −20° C.

Preparation and Characterization of ZWC(PAMAM) Nanoparticle Structures

ZWC derivative solutions were prepared in phosphate buffers (pH 7.4) with ionic strengths, varying the concentration from 0.5 mg/mL to 2 mg/mL. ZWC derivative (PAMAM) ("ZWC(PAMAM)") nanoparticle structures were created by mixing a small volume of PAMAM-methanol solution (40 mg/mL) in the ZWC derivative solution achieving various ZWC derivative to PAMAM ratios (1:1 to 4:1). The formation of ZWC(PAMAM) nanoparticle structures was indicated by the development of turbidity, monitored at 660 nm using a Beckman DU 650 UV-VIS Spectrophotometer (Brea, Calif.). Particle size of ZWC (PAMAM) nanoparticle structures was measured by dynamic light scattering using a Malvern Zetasizer Nano ZS90 (Worchestershire, UK). Count rate (kilo counts per second), proportional to the number of particles in solution, and polydispersity index, an indicator of the extent of particle aggregation, were also noted. Surface charges of ZWC(PAMAM) nanoparticle structures and each components were measured using a Malvern Zetasizer Nano ZS90 at pH ranging from 3 to 9 in ~0.3 increment. For this measurement, all components and nanoparticle structures were prepared in 10 mM NaCl, and the pH was adjusted using 0.1 N HCl or NaOH.

pH-dependent Charge Profiles of PAMAM and ZWC Derivative Components

Zeta potentials of both ZWC derivative and PAMAM were measured at pH values ranging from 3 to 9. PAMAM (0.5 mg/mL) showed positive charges at all pH values (see FIG. 10). ZWC derivatives showed a negative charge at a relatively basic pH and a positive charge at an acidic pH. The pH at which the charge changed (transition pH) appears to correspond on the ratio of succinic anhydride to chitosan. The transition pHs of ZWC derivative prepared with a An/Am ratio of 0.3 ($ZWC_{0.3}$) and 0.7 ($ZWC_{0.7}$) were 6.6 and 4.3, respectively. Since $ZWC_{0.7}$ was more likely to form an electrostatic complex with PAMAM due to the stronger negative charge, $ZWC_{0.7}$ was used in subsequent examples.

Formation of ZWC(PAMAM) Nanoparticle Structures

Upon introduction of ZWC derivative to PAMAM, the mixture immediately became turbid, indicating the formation of nanoparticle structures. The suspension containing 1 mg/mL ZWC derivative and 0.5 mg/mL PAMAM showed an average particle size of 351.8 nm with a relatively narrow size distribution (PDI: 0.16) at a count rate of 1777.3 kilo counts per sound (kcps) (see Table 4). PAMAM as a 0.5 mg/mL colloidal solution in PBS showed a particle size of 184.4 nm, but the count rate and PDI were 42.1 kcps and 0.60, respectively. The low count rate and high PDI indicated that the observed particle size was due to the aggregation of PAMAM in water, which has been reported in the literature. ZWC derivative (1 mg/mL) showed a particle size of 535.2 nm with a similarly low count rate (62.5 kcps) and high PDI (0.76), suggesting that ZWC derivative also aggregated when present alone in this concentration. The high particle count rate of the PAMAM-ZWC mixture indicates that the two components formed nanoparticle structures as complexes, which were distinguished from each component, and the measured particle size reflected that of the complexes rather than a simple sum of the components.

TABLE 4

Particle size, polydispersity index, and derived count rate of ZWC(PAMAM) nanoparticle structures and the components.

| Samples | n | Particle size (diameter, nm) | Polydispersity index (PDI) | Derived count rate (kcps) |
|---|---|---|---|---|
| ZWC(PAMAM) | 9 | 351.8 ± 21.1 | 0.16 ± 0.05 | 1777.3 ± 92.0 |
| PAMAM | 3 | 184.4 ± 25.0 | 0.60 ± 0.01 | 42.1 ± 46.3 |
| ZWC derivative | 3 | 535.2 ± 41.9 | 0.76 ± 0.05 | 62.5 ± 3.8 |

* Samples prepared in phosphate-buffered saline (10 mM phosphate, pH 7.4).
** Each sample contained PAMAM 0.5 mg/mL and/or ZWC 1 mg/mL.

pH-dependent Formation and Dissociation of ZWC(PAMAM) Nanoparticle Structures

Figure 10:
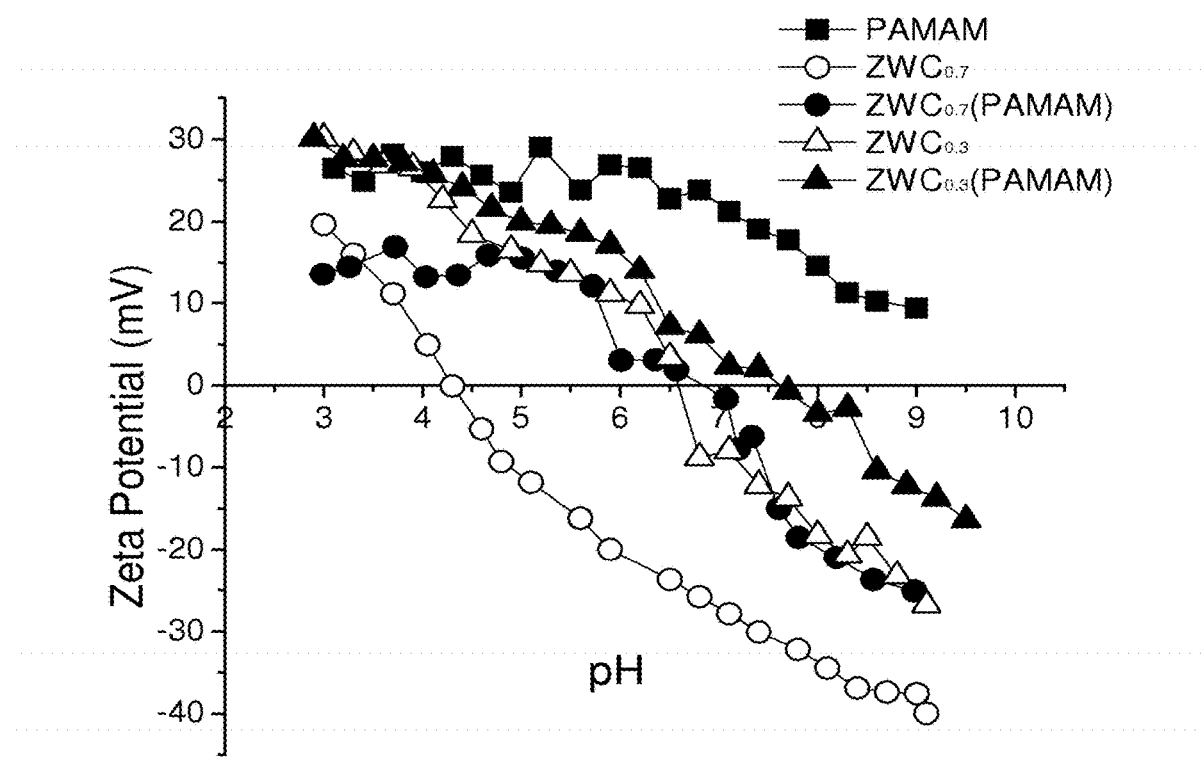
FIG. 10 shows the pH dependent zeta-potential profiles of ZWC derivative, PAMAM, and ZWC(PAMAM). $ZWC_{0.3}$ and $ZWC_{0.7}$ indicate ZWC derivatives prepared with an anhydride to amine ratio of 0.3 and 0.7, respectively. Each curve is a representative of at least 3 runs.

The ZWC(PAMAM) nanoparticle structures demonstrated a pH-dependent charge profile, similar to that of ZWC, but with a transition pH shifted to right from 4.3 to pH 6.8 (see FIG. 10). The increase in transition pH indicates partial neutralization of anionic charge of ZWC by PAMAM. The net charge of ZWC(PAMAM) nanoparticle structures at pH 7.4 was approximately −8 mV.

Figure 11:
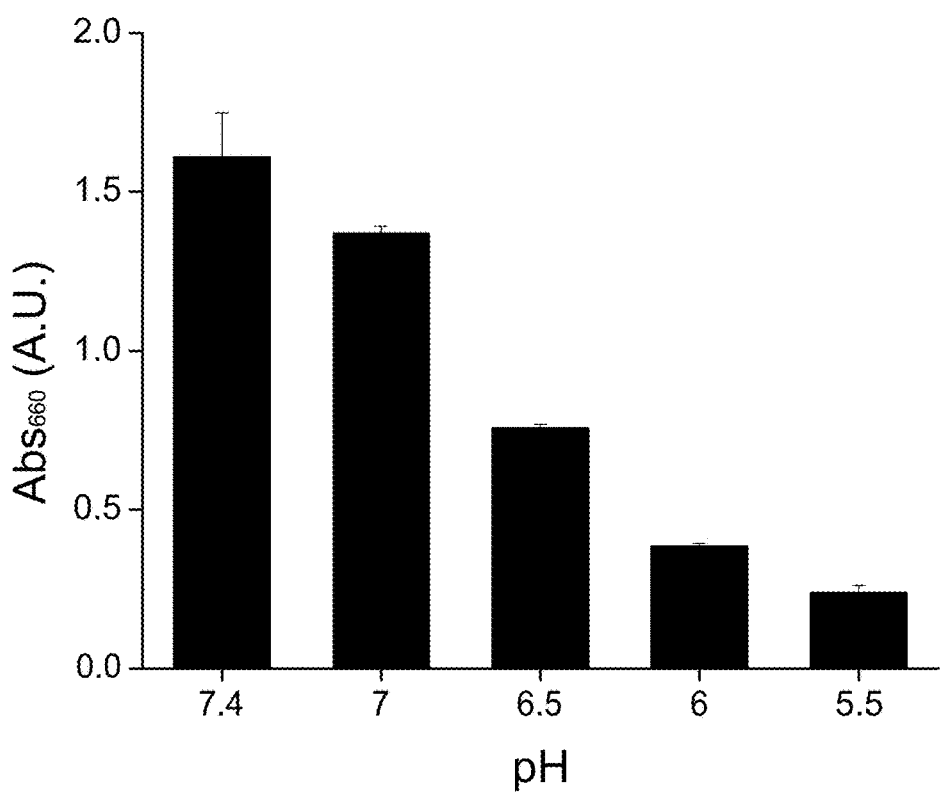
FIG. 11 shows absorbance (@ 660 nm) of ZWC(PAMAM) at different pHs. ZWC(PAMAM) was prepared with ZWC derivative (1 mg/mL) and PAMAM (0.5 mg/mL). Data are expressed as averages with standard deviations of 3 identically and independently prepared samples.
Figure 12:
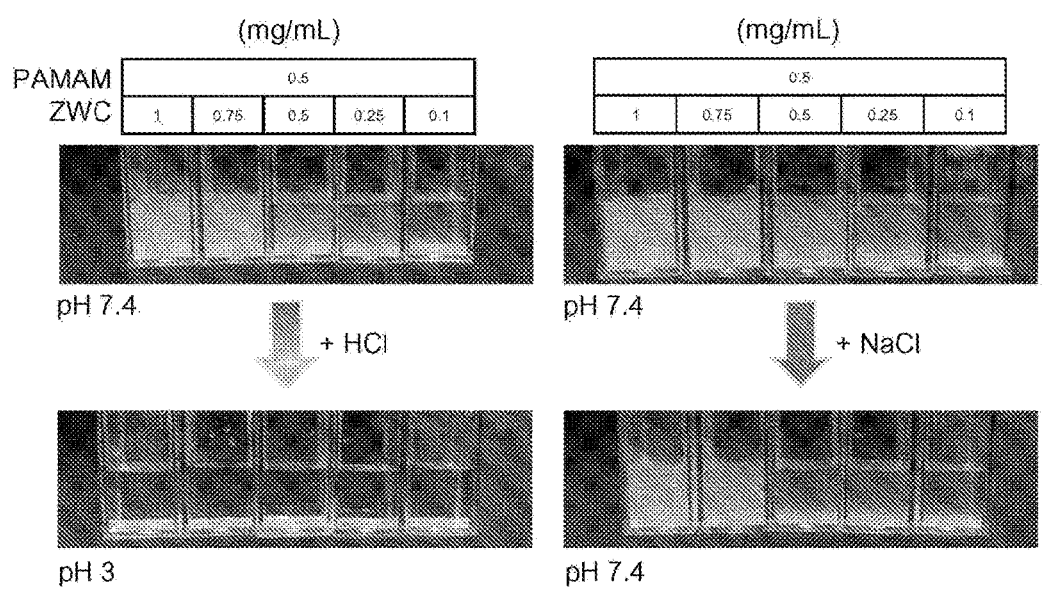
FIG. 12 shows the pH dependent dissociation of ZWC (PAMAM) upon pH decrease from pH 7.4 to 3 by the addition of hydrochloric acid (A). The addition of NaCl that provided the same degree of ion increase and dilution effect without changing the pH did not induce significant decrease in turbidity (B).

Turbidity of the suspension of nanoparticle structures decreased with the decrease of pH (see FIG. 11). When pH was lowered to 3 by the addition of HCl solution, the ZWC(PAMAM) suspension became completely clear, similar to individual ZWC and PAMAM components, indicating dissociation of the nanoparticle structures (see FIG. 12). However, the ZWC(PAMAM) suspension diluted with NaCl solution to a comparable degree while keeping the pH at 7.4 did not show significant change in turbidity. This suggests that the dissociation of nanoparticle structures observed at pH 3 was not due to dilution of the nanoparticle structures or increase of ionic strength in the suspension. Given that ZWC assumes an increasingly positive charge as pH decreases, the dissociation of nanoparticle structures is most likely due to electrostatic repulsion of protonated ZWC and PAMAM.

EXAMPLE 10

Stability Evaluation of ZWC(PAMAM) Nanoparticle Structures

To study the effect of ionic strength on the formation and stability of ZWC(PAMAM) nanoparticle structures, the structures were suspended in pH 7.4 phosphate buffers containing different concentrations of NaCl (10-300 mM) and incubated for 48 hours. ZWC(PAMAM) nanoparticle structures were prepared by mixing 2 mg/mL ZWC solution in phosphate-buffered saline (PBS, 10 mM phosphate, pH 7.4) and 1 mg/mL PAMAM suspension in PBS, in equal volumes. The suspension was serially diluted by factors of 2 and 4 using PBS. Count rate of each suspension was obtained using dynamic light scattering (Malvern Zetasizer) with a 5 mW He—Ne laser operated at 633 nm. Count rates of ZWC and PAMAM solutions were also measured at corresponding concentrations.

Figure 13:
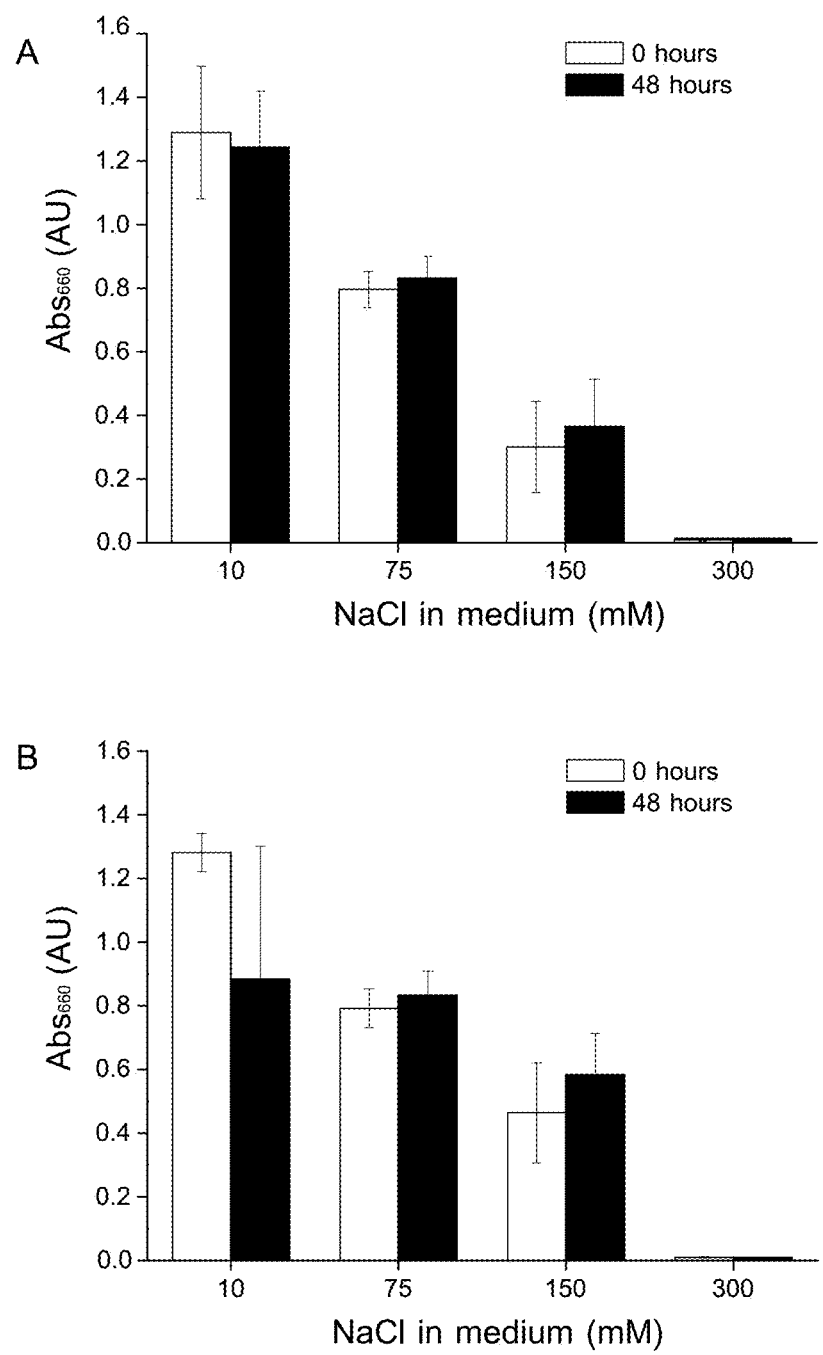
FIG. 13 shows stability of ZWC(PAMAM) incubated in different ionic strengths for 48 hours, as measured with turbidity change. ZWC(PAMAM) prepared with (A) 1 mg/mL ZWC and 0.5 mg/mL PAMAM, and (B) 0.75 mg/mL ZWC and 0.5 mg/mL PAMAM. Data are expressed as averages with standard deviations of 3 identically and independently prepared samples. There was no difference between 0 and 48 hours in all samples ($p>0.05$).

Turbidity of complex suspension decreased as the NaCl concentration increased, reaching a minimal value in 300 mM NaCl solution (see FIG. 13). This result suggests that a large number of ions interfere with the formation of nanoparticle structures and, thus, confirms the electrostatic nature of ZWC(PAMAM) nanoparticle structures. The nanoparticle structures formed and incubated in 150 mM NaCl solution maintained a constant turbidity, particle size, and count rate over 48 hours.

Figure 14:
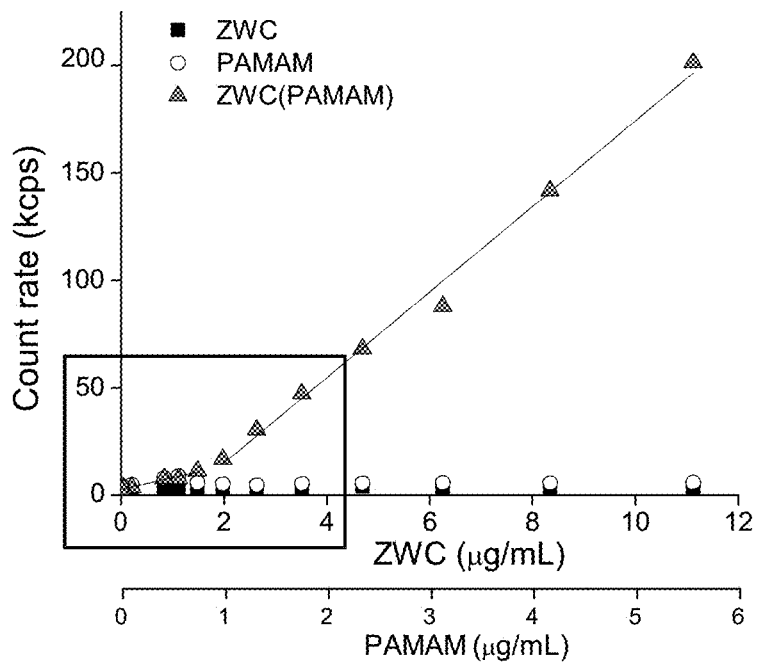
FIG. 14 shows the determination of critical association concentration of ZWC(PAMAM). The result is representative of 3 independently and identically prepared samples. The bottom plot (B) shows a magnified view of the range indicated in the top plot (A).
Figure 14:
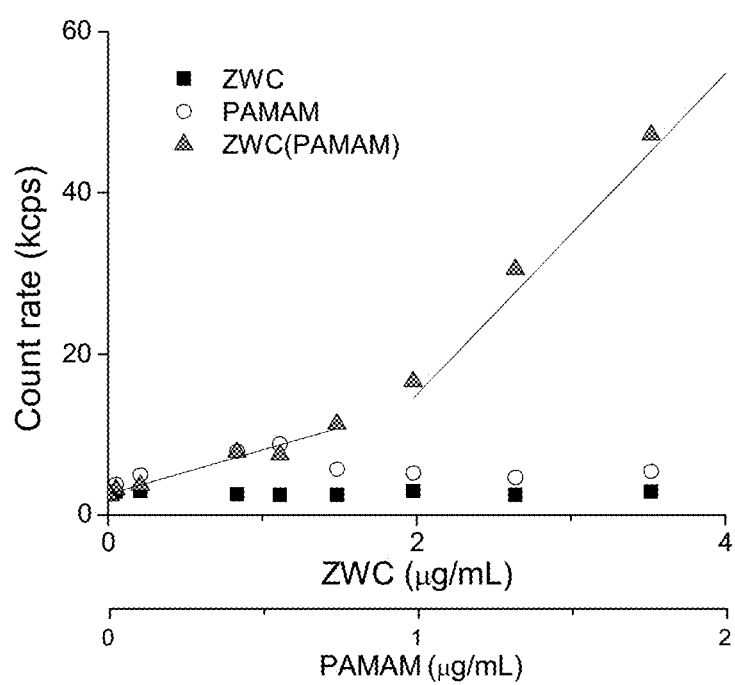

To examine the effect of dilution on stability of ZWC (PAMAM), the critical association concentration (CAC) (i.e., the lowest concentration at which ZWC and PAMAM formed electrostatic complexes) was determined. CAC was determined using dynamic light scattering as the concentration above which the intensity of scattered light (or particle count rate) showed a linear increase with concentration of the components. ZWC or PAMAM alone showed a minimal count rate, which did not change with concentration, indicating the lack of particle formation (see FIG. 14). In contrast, ZWC(PAMAM) nanoparticle structures showed a linear increase in count rate with CAC concentrations corresponding to ZWC 1.8±0.3 µg/mL and PAMAM 0.9±0.2 µg/mL. Below this concentration, the count rate overlapped with those of PAMAM alone, indicating dissociation of ZWC(PAMAM) nanoparticle structures.

EXAMPLE 11

Elucidation of ZWC(PAMAM) Nanoparticle Structure with Fluorescence Spectroscopy

The structure of ZWC(PAMAM) nanoparticles was elucidated by observing changes in fluorescence emission profiles of (i) fluorescently labeled ZWC (ZWC-552) in the presence of unlabeled PAMAM and (ii) fluorescently labeled PAMAM (PAMAM-581) in the presence of unlabeled ZWC. ZWC was labeled with a fluorescent dye FPR-552 ($\lambda_{abs}$: 551 nm; $\lambda_{ex}$: 570 nm) per the manufacturer's protocol. Briefly, 1 mg of FPR-552 was dissolved in a mixture of 50 µL dimethyl sulfoxide (DMSO) and 50 µL DI water, and 1 mg of ZWC was dissolved in 100 µL of phosphate buffer (10 mM, pH 9). One microliter of the FPR-552 solution was incubated with 19 µL of the ZWC solution overnight at room temperature in a dark environment, and excessive dye was removed by dialysis. PAMAM was similarly labeled with an FPR-581 dye ($\lambda_{abs}$: 578 nm; $\lambda_{ex}$: 595 nm). The labeled ZWC and PAMAM were referred to as ZWC-552 and PAMAM-581, respectively.

Fluorescence spectra of ZWC-552, PAMAM-581, ZWC-552 combined with unlabeled PAMAM, and PAMAM-581 combined with unlabeled ZWC solutions were obtained using a Molecular Devices SpectraMax M5 (Sunnyvale, Calif.). Samples containing ZWC-552 were excited at 544 nm with a cutoff of 550 nm, and their emission spectra were read from 550 to 650 nm. Samples containing PAMAM-581 were excited at 578 nm with a 590 nm cutoff, and the emission spectra were read from 590 to 650 nm.

Figure 15:
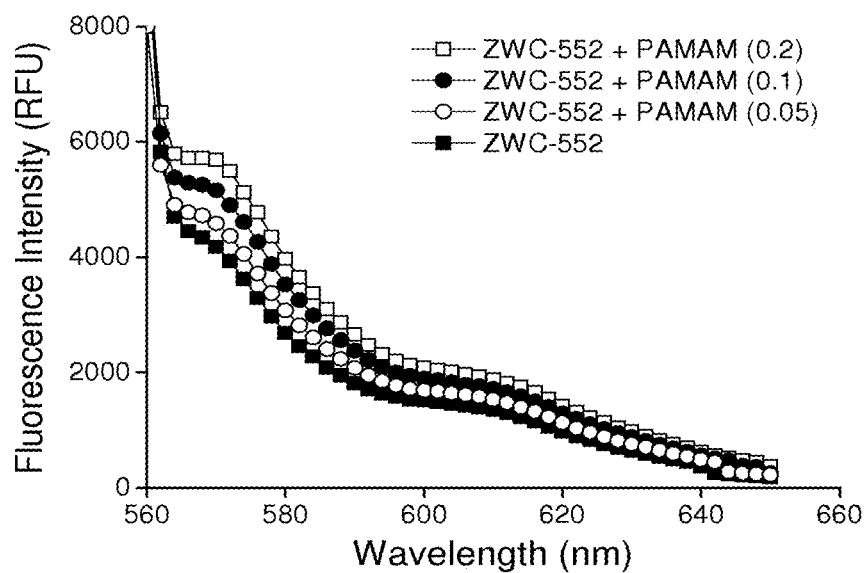
FIG. 15 shows fluorescence profiles of (A) ZWC-552 (0.2 mg/mL) in the presence of unlabeled PAMAM (0.05-0.2 mg/mL) at pH 7.4 (excited at 544 nm; emission scanned from 550 to 650 nm) and (B) PAMAM-581 (0.2 mg/mL) in the presence of unlabeled ZWC (0.05-0.2 mg/mL) at pH 7.4 (excited at 578 nm; emission scanned from 590 to 650 nm). Each plot is representative of three replicates.
Figure 15:
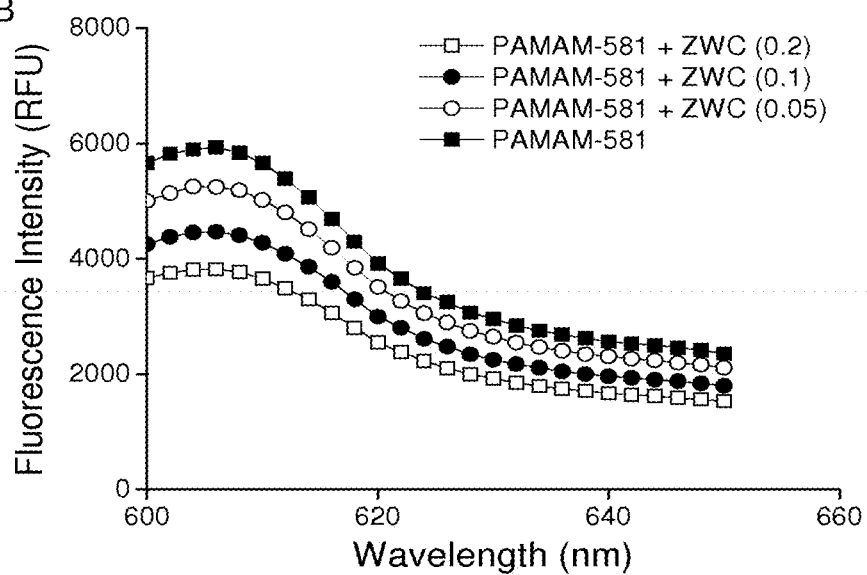

At pH 7.4, a condition that allowed for attractive interaction between ZWC derivative and PAMAM, ZWC-552 showed increasing fluorescence intensity with increasing concentration of unlabeled PAMAM (see FIG. 15A). In contrast, PAMAM-581 incubated with unlabeled ZWC derivative showed decreasing fluorescence intensity with increasing concentration of unlabeled ZWC derivative (see FIG. 15B).

Figure 16:
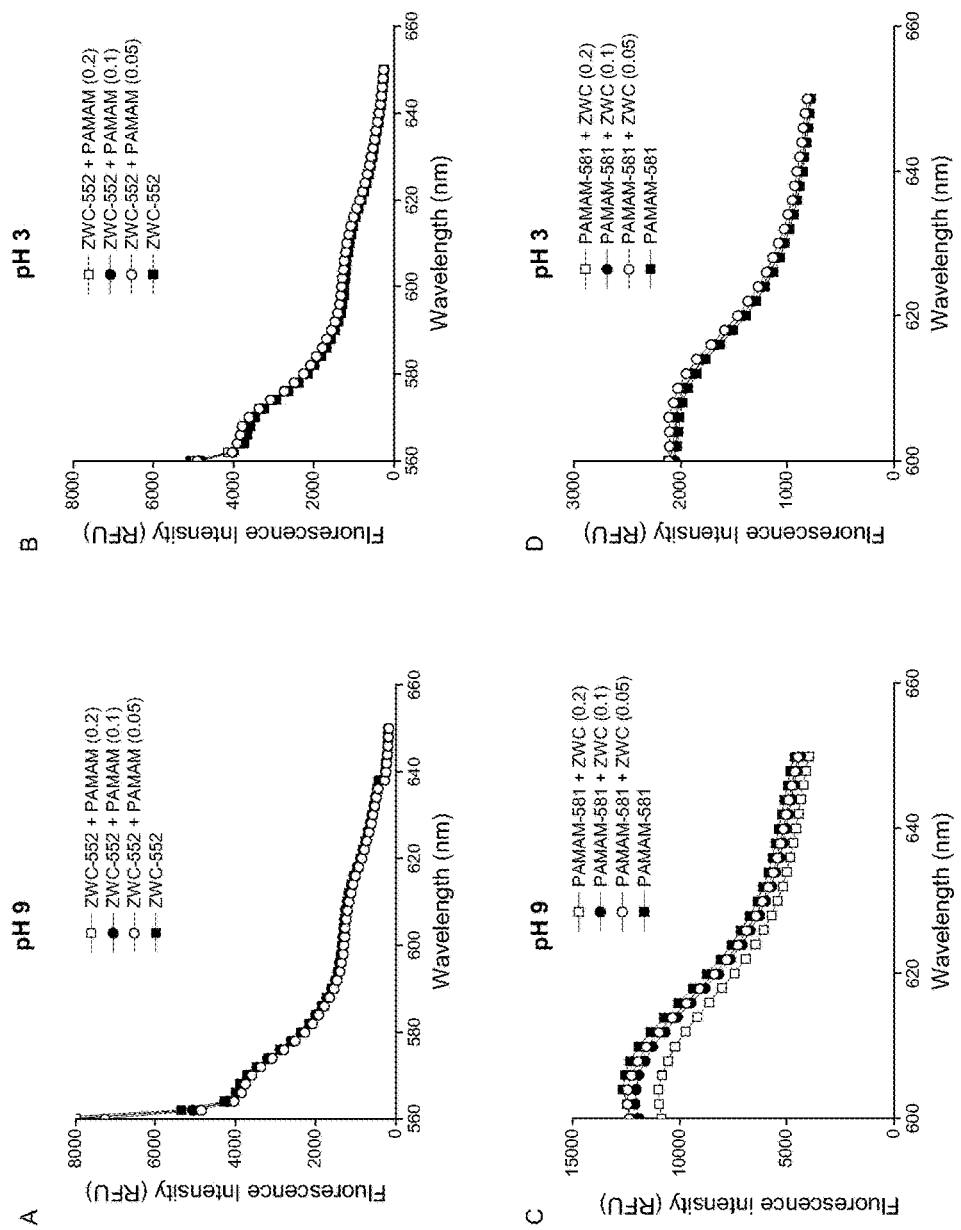
FIG. 16 shows the fluorescence profiles of (A) ZWC-552 (0.2 mg/mL) in the presence of unlabeled PAMAM (0.05-0.2 mg/mL) at pH 9 (excited at 544 nm; emission scanned from 560 to 650 nm), (B) ZWC-552 (0.2 mg/mL) in the presence of unlabeled PAMAM (0.05-0.2 mg/mL) at pH 3 (excited at 544 nm; emission scanned from 560 to 650 nm), (C) PAMAM-581 (0.2 mg/mL) in the presence of unlabeled ZWC (0.05-0.2 mg/mL) at pH 9 (excited at 578 nm; emission scanned from 600 to 650 nm), and (D) PAMAM-581 (0.2 mg/mL) in the presence of unlabeled ZWC (0.05-0.2 mg/mL) at pH 3 (excited at 578 nm; emission scanned from 600 to 650 nm). Each plot is representative of three replicates.

The increasing fluorescence intensity of ZWC-552 with increasing PAMAM may be explained by de-quenching of ZWC-552, which was present as aggregates by themselves but dissociated upon complexation with PAMAM-552. This explanation is supported by the lack of such fluorescence change at pH 9 (see FIG. 16A), where ZWC derivative had a stronger anionic charge and was less likely to self-associate than ZWC derivative at pH 7.4. To the contrary, fluorescence intensity of PAMAM-581 decreased as the amount of ZWC derivative increased. This result suggests that emission of PAMAM-581 fluorescence might have been blocked due to coverage by ZWC derivative. A similar trend was seen at pH 9 (see FIG. 16C), where anionic ZWC derivative and cationic PAMAM-581 were supposed to form an electrostatic complex. These distinct changes in fluorescence intensity of ZWC-552 and PAMAM-581 in the presence of unlabeled counterparts were not seen at pH 3 (see FIGS. 16B and 16D), where both ZWC derivative and PAMAM were charged positively and thus did not form ionic complexes. These results indicate that ZWC(PAMAM) complexes are formed by electrostatic interactions between the two components, in which PAMAM is covered by ZWC derivative.

EXAMPLE 12

Transmission Electron Microscopy (TEM) Evaluation of ZWC(PAMAM) Nanoparticle Structures ZWC (0.5, 1 and 2 mg/mL), PAMAM (0.5 mg/mL), and ZWC(PAMAM) nanoparticle structures (specified concentrations) were prepared in DI water at pH 7.4. Samples were mounted on a 400-mesh Cu grid with formvar and carbon supporting film (not glow-discharged) and stained with 2% uranyl acetate (UA) solution. Excess stain was removed with filter paper, and the grid was dried prior to imaging. Samples were imaged using a Philips CM-100 TEM (FEI Company, Hillsboro, Oreg.) operated at 100 kV, spot size 3, 200 µm condenser aperture, and 70 µm objective aperture. Images were captured using a SIA L3-C 2 megapixel CCD camera (Scientific Instruments and Application, Duluth, Ga.) at original microscope magnifications ranging from 25,000× to 180,000×.

Figure 17:
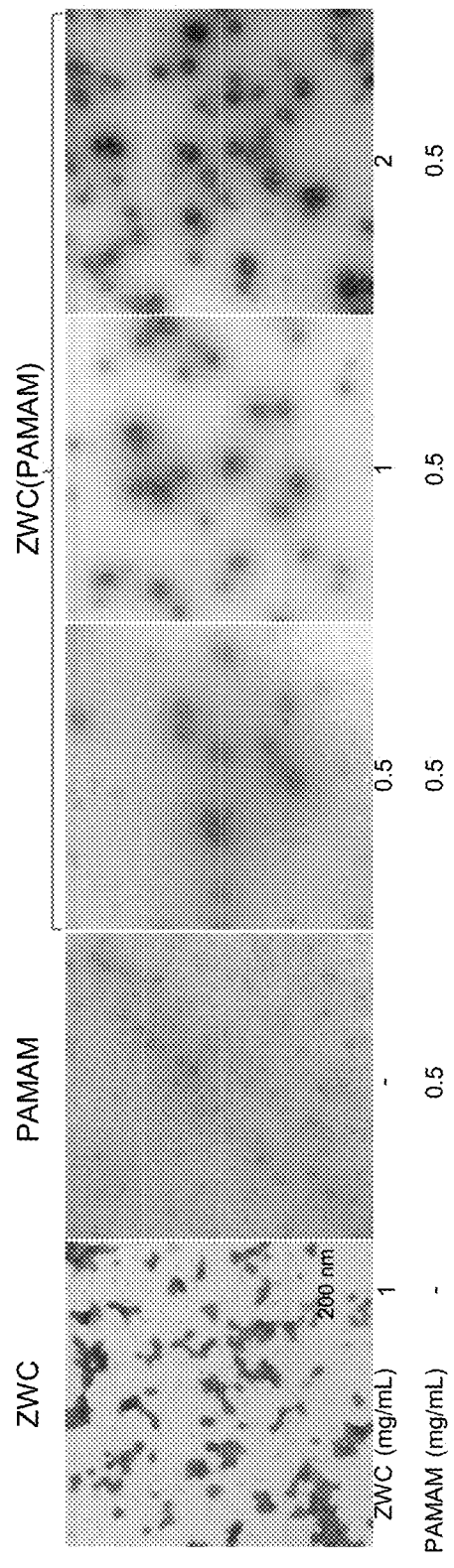
FIG. 17 shows transmission electron micrographs of PAMAM, ZWC, and ZWC(PAMAM).

ZWC(PAMAM) nanoparticle structures and each individual component were visualized with TEM after UA staining (see FIG. 17). PAMAM and ZWC were oppositely stained by UA, which is likely due to the differential affinity of UA for each component. UA breaks down into different acetate ion species, which react with both anionic and cationic groups, but with a much greater affinity for anionic groups such as phosphoryl and carboxyl groups. Therefore, ZWC (which is anionic at pH 7.4) was positively stained, whereas cationic PAMAM (which lacks phosphoryl and carboxyl groups) appeared lighter (negatively stained). In the absence of ZWC, PAMAM was observed as round white particles with a size <10 nm in diameter. In the sample prepared with ZWC and PAMAM at a 2:1 or 4:1 ratio, dark ZWC appeared around light PAMAM. In contrast, at a 1:1 ratio, numerous PAMAM appeared separately from ZWC, indicating incomplete ZWC coverage of PAMAM.

EXAMPLE 13

Hemolytic Activity and Cytotoxicity of ZWC(PAMAM) Nanoparticle Structures

To investigate the effect of ZWC coating, the hemolytic activity of ZWC(PAMAM) nanoparticle structures was compared with that of PAMAM. First, blood was collected from Spague-Dawley rats via the dorsal aorta. Then red blood cells (RBC) were isolated from blood and washed using 210 mM NaCl solution until the supernatant became free of red color. Purified RBC pellets were incubated with 900 μL of ZWC, PAMAM, or ZWC(PAMAM) nanoparticle structures in PBS at various concentrations for 1 h at 37° C. DI water (positive control) caused complete lysis in this condition. PBS was used as a negative control. Samples were centrifuged at 2000 rpm for 5 minutes following incubation. 980 μL of supernatant was removed, and the remaining RBC pellet was dissolved in 980 μL of DI water. Absorbance of the RBC solution was measured at 541 nm. Data were expressed as normalized to the PBS-treated RBC.

Figure 18:
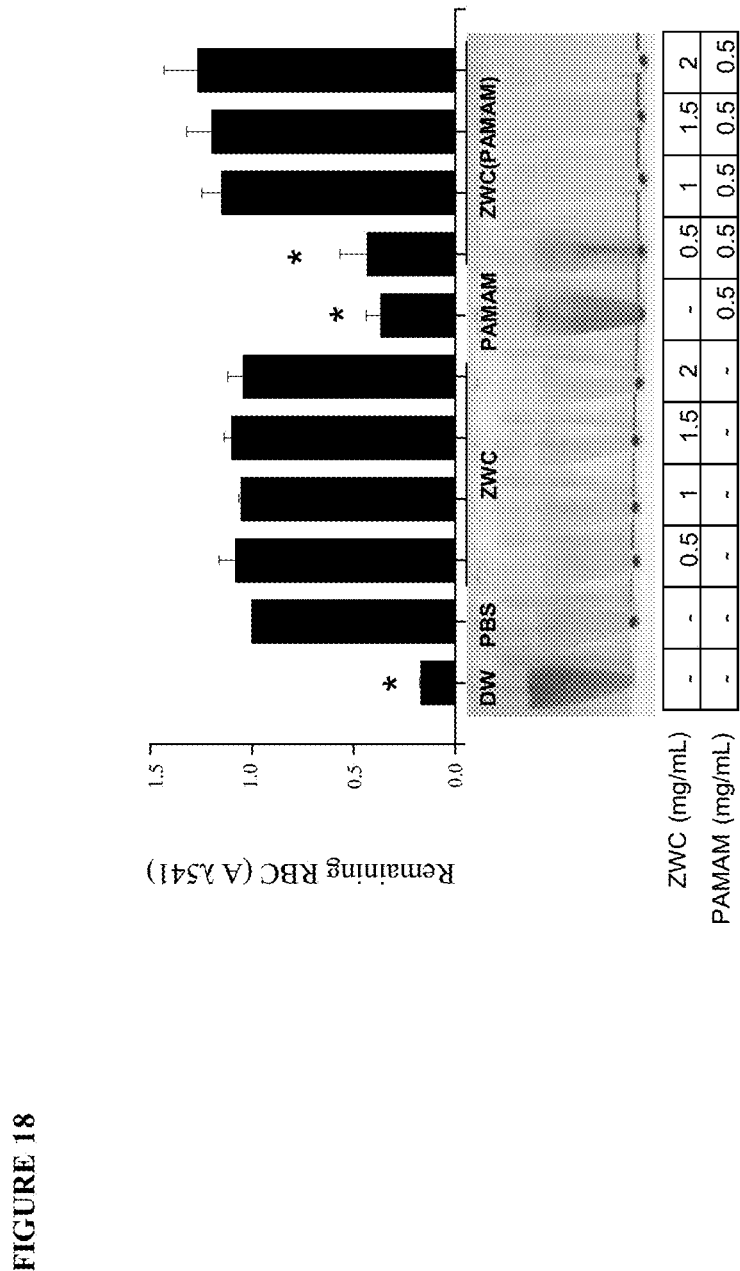
FIG. 18 shows hemolytic activity of ZWC, PAMAM, and ZWC(PAMAM). RBCs were incubated with the samples at concentrations shown in the table at 37° C. and pH 7.4 for 1 hour (A). Pictures were taken after centrifugation of the tubes at 2000 rpm for 5 min (B). The pellets are intact RBC, and the red supernatant or precipitate on the tube wall show hemoglobin released from the lysed RBC. Data are expressed in (C) as averages with standard deviations of 3 identically and independently prepared samples. *: $p<0.05$ vs. PBS.

As shown in FIG. 18, ZWC alone (at concentrations of 0.5-2 mg/mL) had no hemolytic effect on RBC. However, PAMAM at 0.5 mg/mL showed significant hemolysis, and ZWC(PAMAM) nanoparticle structures containing 0.5 mg/mL ZWC and 0.5 mg/mL PAMAM (ZWC:PAMAM=1:1) showed RBC lysis to a similar extent. On the other hand, ZWC(PAMAM) nanoparticle structures formed at higher ZWC:PAMAM ratios (between 2:1 to 4:1) exhibited no hemolysis. This result suggests that ZWC coating prevented direct interaction between PAMAM and RBC.

In addition, the cytotoxicity of ZWC, PAMAM, and ZWC(PAMAM) nanoparticle structures was evaluated using NIH 3T3 mouse fibroblast cells (ATCC, Rockville, Md.) via an MTT (3-(4,5-Dimethylthiazol-2-yl)-2,5-diphenyltetrazolium bromide) assay. Fibroblasts were cultured in DMEM high glucose medium supplemented with 10% bovine calf serum (ATCC, Rockville, Md.), 100 U/mL penicillin and 100 μg/mL streptomycin. For the MTT assay, cells were seeded in 96-well plates at a density of 10,000 cells per well. After overnight incubation, culture medium was replaced with various concentrations of ZWC (0.5, 1, 1.5, 2 mg/mL), PAMAM (0.05, 0.1, 0.5 mg/mL), or ZWC(PAMAM) nanoparticle structures (formed with combinations of ZWC and PAMAM concentrations) suspended in PBS containing 10% calf serum.

After 4 hours of incubation with the samples, the media was replaced with 100 μL of fresh medium and 15 μL of 5 mg/mL MTT, and the incubation was continued for 3.5 hours. The stop/solubilization solution was then added to dissolve the formed formazan. To avoid the interference due to turbidity of ZWC(PAMAM) nanoparticle structures, plates were centrifuged for 30 minutes at 4000 rpm, and clear supernatant was collected prior to reading. Cell viability was estimated by reading the absorbance of the solubilized formazan in the supernatant at 562 nm. The obtained absorbance was normalized to the absorbance of cells grown in complete medium without any treatment.

Figure 19:
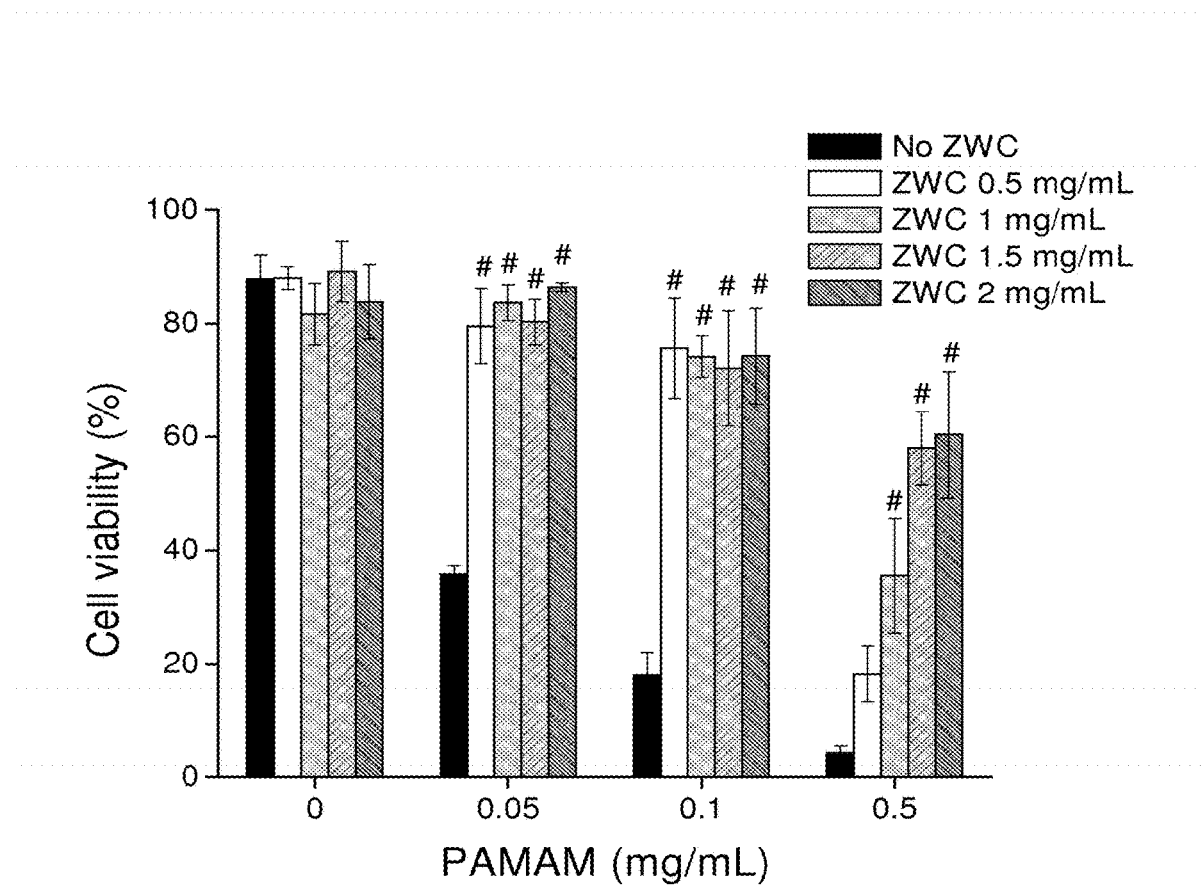
FIG. 19 shows the cell viability of ZWC, PAMAM, and ZWC(PAMAM) at various concentrations using MTT assay. Data are expressed as averages with standard deviations of 3 repeated tests. #: $p<0.005$ vs. PAMAM (No ZWC) at each concentration. Numbers indicate the final concentrations of ZWC and/or PAMAM in culture medium.

The protective effect of ZWC was confirmed by the MTT assay (see FIG. 19). ZWC had minimal cytotoxic effects on fibroblasts at all concentrations. In contrast, cell viabilities decreased to 36%, 18%, and 4% of non-treated control cells at 0.05, 0.1, and 0.5 mg/mL PAMAM, respectively. The cytotoxicity of PAMAM decreased with the addition of ZWC at the concentrations of 0.5-2 mg/mL for each level of PAMAM. At the lower PAMAM concentrations, cell viability was improved upon addition of ZWC 0.5 mg/mL, from 36% (0.05 mg/mL PAMAM) and 18% (0.1 mg/mL PAMAM) to 80% and 76%, respectively, which were comparable to the viability at ZWC 0.5 mg/mL alone. The viability did not increase beyond this level at higher concentrations of ZWC, indicating that 0.5 mg/mL ZWC was sufficient for shielding between 0.05-0.1 mg/mL PAMAM. For 0.5 mg/mL PAMAM, cell viability gradually increased in a dose-dependent manner with the increase of ZWC concentration, reaching 60% with 2 mg/mL ZWC. This result indicates that ZWC coating can protect blood cells from the toxic effect of PAMAM.

EXAMPLE 14

Confocal Microscopy Evaluation of ZWC(PAMAM) Nanoparticle Structures

To test the pH-dependent removal of ZWC derivative coating from a ZWC(PAMAM) nanoparticle structure, cell responses to the nanoparticle structure were observed at different pHs (7.4 and 6.4) using confocal microscopy. SKOV-3 ovarian carcinoma cells (ATCC, Rockville, Md.) were cultured in RPMI-1640 medium supplemented with 10% fetal bovine serum (FBS), 100 U/mL penicillin, and 100 μg/mL streptomycin. The cells were plated in 35 mm diameter glass bottom dishes at a density of 800,000 per dish. After overnight incubation, the medium was replaced with a suspension of PAMAM or ZWC(PAMAM) nanoparticle structures. Here, the PAMAM sample was prepared in PBS, and the ZWC(PAMAM) nanoparticle structures were prepared in PBS by mixing ZWC with PAMAM at a 2:1 ratio. The suspensions were supplemented with 10% FBS, and their pH was adjusted to 7.4 or 6.4 before adding to the cells. The final concentration of each component in the suspensions was 1 mg/mL ZWC derivative and/or 0.5 mg/mL PAMAM. After incubation with the treatments for 1 hour at 37° C., cells were washed twice in PBS (pH 7.4) or pH-adjusted PBS (pH 6.4) and imaged in each buffer containing 1 μL of DRAQ5 nuclear stain (Axxora, San Diego, Calif.). DRAQ5 was excited with 633 nm laser and images of cell nuclei were obtained using an Olympus FV1000 confocal microscope using a 60× objective.

Figure 20:
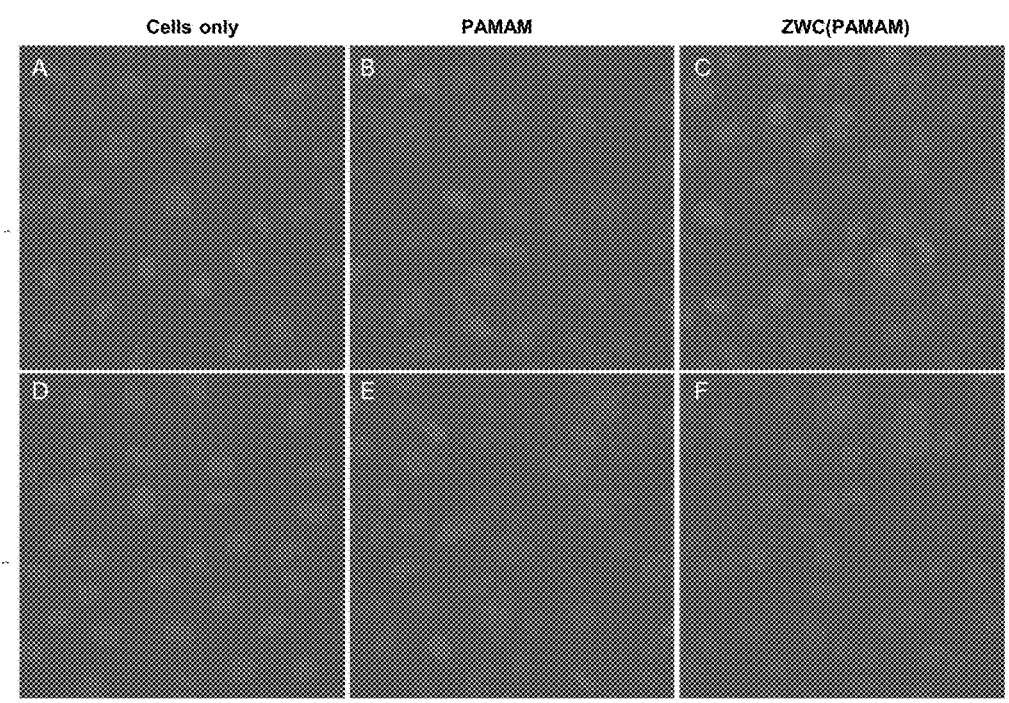
FIG. 20 shows the nuclei of cells treated with PAMAM or ZWC(PAMAM) at pH 7.4 (top) and pH 6.4 (bottom): (A, D) cells only, (B, E) PAMAM (0.5 mg/mL), and (C, F) ZWC (PAMAM) equivalent to PAMAM (0.5 mg/mL) and ZWC (1 mg/mL).

At both pHs, SKOV-3 cells treated with 0.5 mg/mL PAMAM showed punctate signals around the nuclei (see FIGS. 20B and 20E), representing nuclei fragmentation, which may be attributable to the pro-apoptotic effect of PAMAM. The cells treated with ZWC(PAMAM) at pH 7.4 (see FIG. 20C) were comparable to buffer-treated ones (see FIGS. 20A and 20D) with no signs of abnormality. In contrast, the punctate nuclear signals were seen in the cells treated with ZWC(PAMAM) at pH 6.4 (see FIG. 20F), similar to those treated with PAMAM alone (see FIGS. 20B and 20E).

EXAMPLE 15

Materials

Chitosan (CS; MW: 15 kDa; degree of deacetylation: 87%) was purchased from Polysciences (Warrington, Pa., USA). LPS, LPS-FITC conjugate, and CS with a molecular weight of 50-190 kD and a deacetylation degree of 83% were purchased from Sigma-Aldrich (St. Louis, Mo., USA). FPR-648 dye was a gift from BioActs (Incheon, Korea). PMJ2-PC mouse peritoneal macrophage cell line was purchased from ATCC (Manassas, Va., USA). Macrophage inflammatory protein (MIP)-2 enzyme-linked immunosorbent assay (ELISA) kit was purchased from R&D Systems (Minneapolis, Minn., USA). LysoTracker Red DND-99, cell culture medium and supplements were purchased from Invitrogen (Carlsbad, Calif., USA). p38 MAPK and p-p38 MAPK primary antibodies and HRP-conjugated anti-rabbit IgG were purchased from Cell Signaling Technology (Danvers, Mass., USA). All other reagents were purchased from Sigma-Aldrich.

ZWC Synthesis

ZWC was produced as described above in Example 1. Briefly, 200 mg of CS acetate was dissolved in 30 mL of water, and 70 mg of succinic anhydride (anhydride to amine ratio, An/Am ratio of 0.7) was added as solid to the CS solution while stirring. The reaction mixture was maintained at pH 6-6.5 for 1 h, stirred overnight at pH 8-9, and dialyzed against deionized water prior to lyophilization. Optionally, ZWC was reacted with 30% $H_2O_2$ under vigorous stirring for 30 or 60 min at room temperature to produce lower molecular weight ZWC (named ZWC30' and ZWC60' according to the reaction time) [15]. For quality control of ZWC, the zeta potential of ZWC solution was measured at different pH, the pI determined, and H-NMR spectra examined as described in a previous report [2].

MIP-2 Production Assay from LPS-challenged Macrophages

PMJ2-PC mouse peritoneal macrophages were grown in Dulbecco's Modified Eagle Medium (DMEM) supplemented with 5% fetal bovine serum, 5 mM HEPES, 100 units/mL of penicillin and 100 pg/mL of streptomycin (referred to as complete medium). The cells were seeded in a 24-well plate at a density of 150,000 cells per well in 1 mL of medium. After overnight incubation, LPS (from *Escherichia coli* O111:B4) was added to the medium in the final concentration of 1 μg/mL. Subsequently, 100 μL of ZWC solution was added to each well to bring the final chitosan concentration in the medium to 1 or 2 mg/mL. In control groups, PBS was added in lieu of ZWC solution. After a 24-h incubation, the plate was centrifuged at 931 rcf for 10 min to separate culture medium from the cells. The concentration of macrophage inflammatory protein (MIP)-2 in the medium was determined using an MIP-2 ELISA kit according to the manufacturer's instruction. A standard calibration curve was prepared in the range of 0-500 pg/mL. The sampled medium was diluted 10 times prior to the ELISA analysis.

Confocal Microscopy of Macrophage Uptake of ZWC

ZWC was fluorescently labeled for tracking its uptake by macrophages. Twenty five milligrams of ZWC was dissolved in 2.5 mL of 0.1 M $NaHCO_3$ buffer (pH 9.0) and mixed with 100 μL of 10 mg/mL aqueous FPR-648 dye solution ($\lambda_{Ex}$: 648 nm; $\lambda_{Em}$: 672 nm). The mixture was reacted overnight in darkness. The fluorescently labeled ZWC (ZWC*) was purified by dialysis against deionized water and lyophilized. Peritoneal macrophages were plated in 35 mm dishes at a density of 160,000 cells/$cm^2$. After 24 h, the medium was replaced with 1 mL of fresh complete medium containing 0.6 mg/mL ZWC*. After 3 h of incubation with, cells were washed twice with the medium in order to remove the free ZWC*. When lysosomes were stained, the ZWC*-laden cells were incubated in 100 nM LysoTracker Red for 30 min. After washing, Hoechst 33342 was added to 2 μg/mL 30 min prior to imaging. Confocal microscopy was performed using Nikon A1R confocal microscope equipped with a Spectra Physics 163C argon ion laser and a Coherent CUBE diode laser. ZWC* was excited with a 640 nm laser, and the emission was read from 660 to 710 nm. Cell nuclei were excited with a 408 nm laser, and the emission was read from 425 to 475 nm. LysoTracker was excited with a 561 nm laser, and the emission was read from 570 to 620 nm.

Western Blotting

PMJ2-PC peritoneal macrophages were seeded in 24-well plate with a seeding density of $1.5 \times 10^5$ cells per well in 1 mL of complete DMEM. After an overnight incubation, one tenth of medium was replaced with PBS (control group) or PBS containing 2 mg of ZWC (treatment group). After 20 h of incubation, the cells were centrifuged at 335 rcf for 5 min. After discarding the supernatant, the cells were redispersed in fresh complete medium containing 1 μg/mL LPS and incubated for 10, 20, or 45 min. The cells were then harvested and lysed in 0.25 mL of protein solubilizing mixture containing 25% sucrose, 2.5% sodium dodecyl sulfate (SDS), 25 mM Tris, 2.5 mM EDTA and 2.5% pyronin Y. Forty microliters of cell lysate was separated in 10% SDS-polyacrylamide gel and transferred to polyvinylidene fluoride membranes. The membranes were blocked with 0.5 v/v % goat serum in NP40 buffer for 0.5 h and incubated with p38 MAPK and p-p38 MAPK primary antibodies overnight at 4° C. The antibodies were detected with HRP-conjugated anti-rabbit IgG for 1 h at room temperature. Immunoreactive bands were visualized with enhanced chemiluminescence reagents (ECL) and detected by Azure C300 (Azure Biosystems, Inc., Dublin, Calif., USA).

Flow Cytometry

Flow cytometry was performed on peritoneal macrophages incubated with fluorescently labeled LPS (LPS-FITC) for different purposes. To test whether ZWC interacts with LPS, 50 μg of LPS-FITC was mixed with 10 mg of ZWC in 1 mL of 0.9% NaCl and incubated at room temperature for 1 h. ZWC was then precipitated by decreasing the solution pH to 4.8 with 0.1 M HCl and removed by a 15-min centrifugation at 9,300 rcf. Assuming that LPS-FITC was present in the supernatant, a volume of supernatant equivalent to 1 μg of LPS-FITC was sampled and added to 1 mL of the peritoneal macrophage culture in the complete medium. LPS-FITC treated in the same way without ZWC (mock-treated) was used for a control group of cells. After 10 h of incubation, cells were collected by gentle pipetting and analyzed with a BD Accuri C6 flow cytometer (San Jose, Calif., USA).

To test whether the ZWC-LPS interaction interferes with LPS binding to macrophages, LPS-FITC was added to macrophages together with ZWC, bringing their concentrations in culture to 2 μg/mL and 2 mg/mL, respectively, and incubated for 1 or 2 h at 37° C. To test whether ZWC competes with LPS for the same receptor, the macrophages were pre-treated with 2 mg/mL of ZWC for 1 h prior to the addition of LPS-FITC. After a 2-h incubation, the macrophages were collected and analyzed with a Beckman Coulter FC500 flow cytometer (Indianapolis, Ind., USA). LPS-FITC-bound macrophages were detected with an FL1 detector ($\lambda_{Ex}$: 488 nm; $\lambda_{Em}$: 525/40 nm). For all analyses, untreated cells were used as a negative control. A total of 10,000-20,000 gated events were acquired for each analysis.

Analytical Ultracentrifugation

To elucidate the shape distributions of ZWC and LPS and their interactions, sedimentation velocity experiments were conducted on a Beckman Coulter XLI analytical ultracentrifuge. LPS (or LPS-FITC) and ZWC samples were mixed and dialyzed extensively against PBS buffer at room temperature. LPS concentration was kept constant at 0.25 mg/mL, whereas ZWC concentration was varied from 0.25 to 1.25 mg/mL. The samples were then centrifuged at 201,600 or 32,256 rcf using two-sector 1.2 cm path-length carbon-filled Epon centerpieces. The experiments were conducted on an An-50 Ti rotor at 20° C. Interference scans were collected every five minutes for a total of 150 scans. LPS-FITC was measured at 495 nm in absorbance in addition to interference optics. The density and relative viscosity of the buffers were calculated with SEDNTERP version 20120828 BETA [16] to be 0.99823 g/mL and 0.01018 P, respectively. 1 s-g* distributions were analyzed using SEDFIT version 14.3e [17].

Surface Plasmon Resonance

SPR analysis was performed using a Biacore 3000 (GE Healthcare Life Sciences, Piscataway, N.J., USA) to detect the ability of ZWC to establish electrostatic and/or hydrophobic interactions with a surface. An L1 sensor chip with negatively charged carboxymethylated dextran and hydrophobic alkyl chains was used as a model surface. ZWC was dissolved in HEPES-buffered saline (HBS, pH 7.4) at a concentration of 10 µM or 100 µM and injected for 5 min at a flow rate of 4 µL/min. As a positive control, PEG550-PE was injected at a concentration of 0.5 mM for 5 min. The L1 chip was regenerated using 40 mM n-octyl 3-D-glucopyranoside prior to each injection. The running buffer was HBS, and experiments were performed at 25° C.

Administration of ZWC in Septic Animals

All animal procedures were performed according to a protocol approved by the Purdue Animal Care and Usage Committee, in accordance with the NIH Guideline for the Care and Use of Laboratory Animals. Male C57BL/6 mice at 8-9 weeks of age weighing 24.8±1.5 g were used for this study. The animals were kept at 25° C. with 12 h light-dark cycles, and food and water were allowed ad libitum. After a one-week acclimatization period, the mice were randomly divided into LPS (n=9), ZWC (n=10), and CS groups (n=10). The animals in the LPS group received an IP injection of the LPS (E. coli O111:B4, 20 mg/kg) solution in 1 mL of sterile saline, and those in the ZWC and CS groups received a mixture of LPS (20 mg/kg) and ZWC or LPS and CS (800 mg/kg) in 1 mL of sterile saline. For the observation of pre-treatment effect, ZWC or CS (800 mg/kg) was injected IP 1 h prior to the LPS injection (n=5 for each group). The animals were observed every 6-8 h up to 1 week. The body temperature was measured with a Pocket Infrared Thermometer (Braintree Scientific, Inc., Braintree, Mass., USA) at each observation, and the body weight recorded daily. Buprenorphine (0.05 mg/kg) was injected subcutaneously every 6-8 h for 2 days and when severe signs of distress (labored breathing, hunched positioning, and reluctance to move) were observed. When an animal was found dead at the time of observation, the time of death was estimated to be in the middle of the last two observation times. When an animal was found to be moribund at the time of observation, animals were euthanized by $CO_2$ asphyxiation followed by cervical dislocation. Upon necropsy, organs in the peritoneal cavity were sampled, fixed in 4% formalin, and embedded in paraffin for hematoxylin and eosin staining.

Statistical Analysis

All data were expressed as means±standard deviations. Statistical analyses were performed with GraphPad Prism 6 (La Jolla, Calif., USA). Unless specified otherwise, one-way ANOVA was performed to determine the difference among the groups, followed by pairwise comparison based on the Tukey procedure. In vivo survival data were plotted using the Kaplan-Meier method and analyzed with the Log-rank (Mantel-Cox) test. A value of $p<0.05$ was considered statistically significant.

A. Preparation of ZWC

Figure 21:
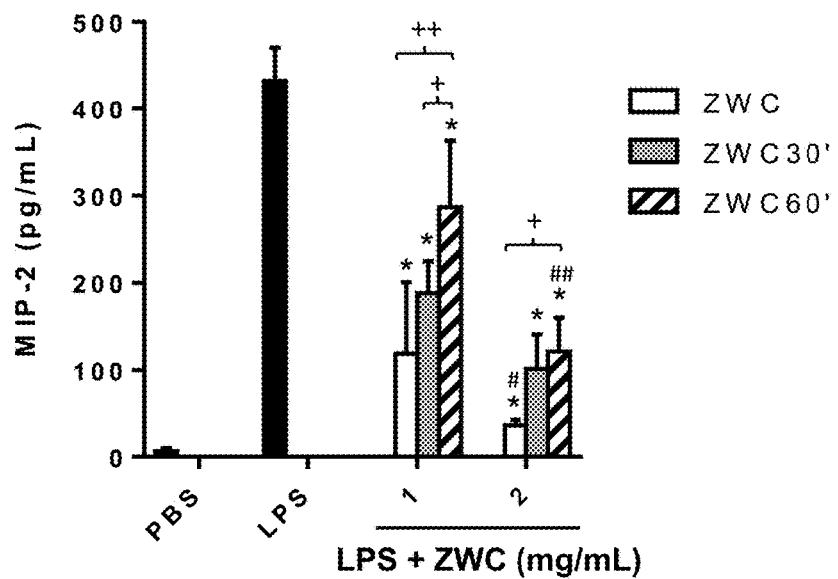
FIG. 21 shows the dose-dependent effects of ZWC, ZWC30', and ZWC60' on MIP-2 production from LPS-challenged PMJ2-PC mouse peritoneal macrophages. MIP-2 levels in the culture media of macrophages were determined by ELISA. The sampled media were diluted 10 times prior to analysis. Data are expressed as averages with standard deviations of three repeated measurements. *: $p<0.0005$ vs. LPS, #: $p<0.05$ vs. 1 mg/mL; and ##: $p<0.0001$ vs. 1 mg/mL; +: $p<0.05$; ++: $p<0.0001$ by Tukey test.

As indicated above, ZWC was produced by reacting CS and succinic anhydride with an anhydride to amine (An/Am) molar ratio of 0.7, because this product was superior to one made with a lower An/Am ratio in suppressing the production of a pro-inflammatory chemokine, macrophage inflammatory protein (MIP)-2, from LPS-challenged macrophages [3]. 53.4% of the repeating units were amidated at this ratio (data not shown). ZWC had an isoelectric point (pI) of 4.5 (data not shown) and showed good water solubility at pH's distant from the pI, unlike the parent CS, which precipitated at pH 7. Prior to the in vivo administration, ZWC was prepared in different molecular weights (MW) to find the optimal form. Lower MW ZWC's were prepared by digesting ZWC (15 kDa) with $H_2O_2$ for different times (30 or 60 min). All ZWCs (ZWC, ZWC30', and ZWC60') inhibited MIP-2 production in LPS-challenged PMJ2-PC mouse peritoneal macrophages in a dose-dependent manner; however, the undigested ZWC was more effective than the degraded ones at each concentration (FIG. 21). ZWC was also produced with a higher MW CS (50-190 kDa) but had no effect on MIP-2 production, likely due to its limited solubility in the culture medium. Accordingly, 15 kDa ZWC was used for in vivo administration.

B. In Vivo Effects of ZWC in LPS-Challenged Mice

Figure 22:
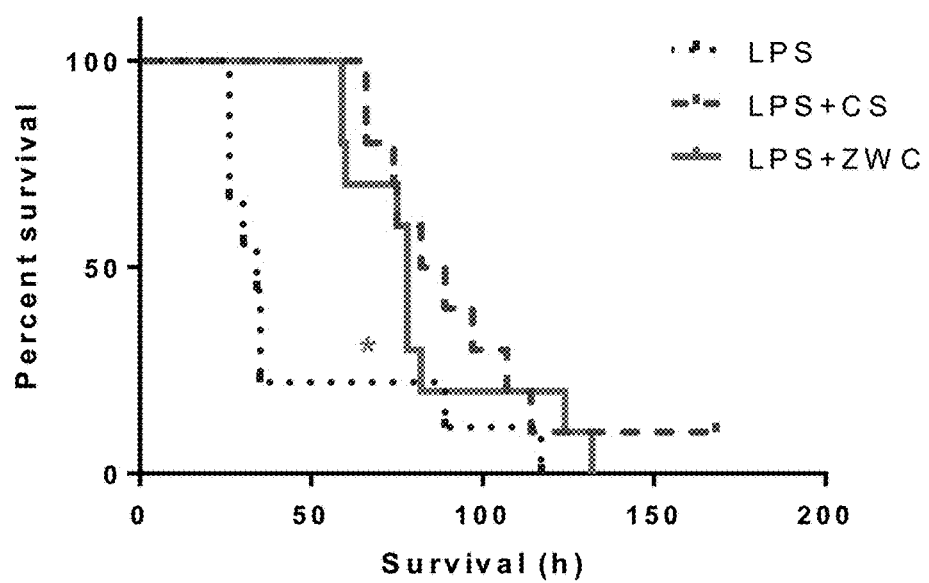
FIG. 22 shows the results of Kaplan-Meier analysis of survival. C57BL/6 mice were injected IP with LPS (20 mg/kg) and treatments (CS or ZWC, 800 mg/kg). n=9 (LPS); n=10 (CS, ZWC). LPS vs. LPS+ZWC: p=0.0465, LPS vs. LPS+CS: p=0.0634, by Log-rank (Mantel-Cox) test.

The protective effect of ZWC and CS was tested in a standard animal model of sepsis, where LPS is injected intraperitoneally (IP) to cause systemic inflammation that mimics the initial clinical features of sepsis, such as the production of pro-inflammatory cytokines, systemic hypotension, and decrease in glomerular perfusion [4]. C57BL/6 male mice were injected with LPS IP. ZWC or CS was administered IP together with LPS or 1 h prior to the LPS challenge, and the mice were observed for 1 week. Animals that received LPS indeed deteriorated quickly, showing acute hypothermia and weight loss (data not shown). With no treatment, most animals died within 48 h, with a median survival time of 34 h (FIG. 22). On the other hand, animals receiving LPS simultaneously with ZWC or CS showed median survival times of 78 h and 85.5 h, respectively (LPS vs. LPS+ZWC: p=0.0465, LPS vs. LPS+CS: p=0.0634, by Log-rank (Mantel-Cox) test). Similarly, the treatment with ZWC or CS prior to the LPS challenge increased the median survival times to 74 h (ZWC) and 82 h (CS), although statistical difference from the LPS control was not observed due to the small sample size (data not shown). In both simultaneous injection and pre-treatment, there was no significant difference between ZWC and CS-treated groups in the median survival time.

Figure 23:
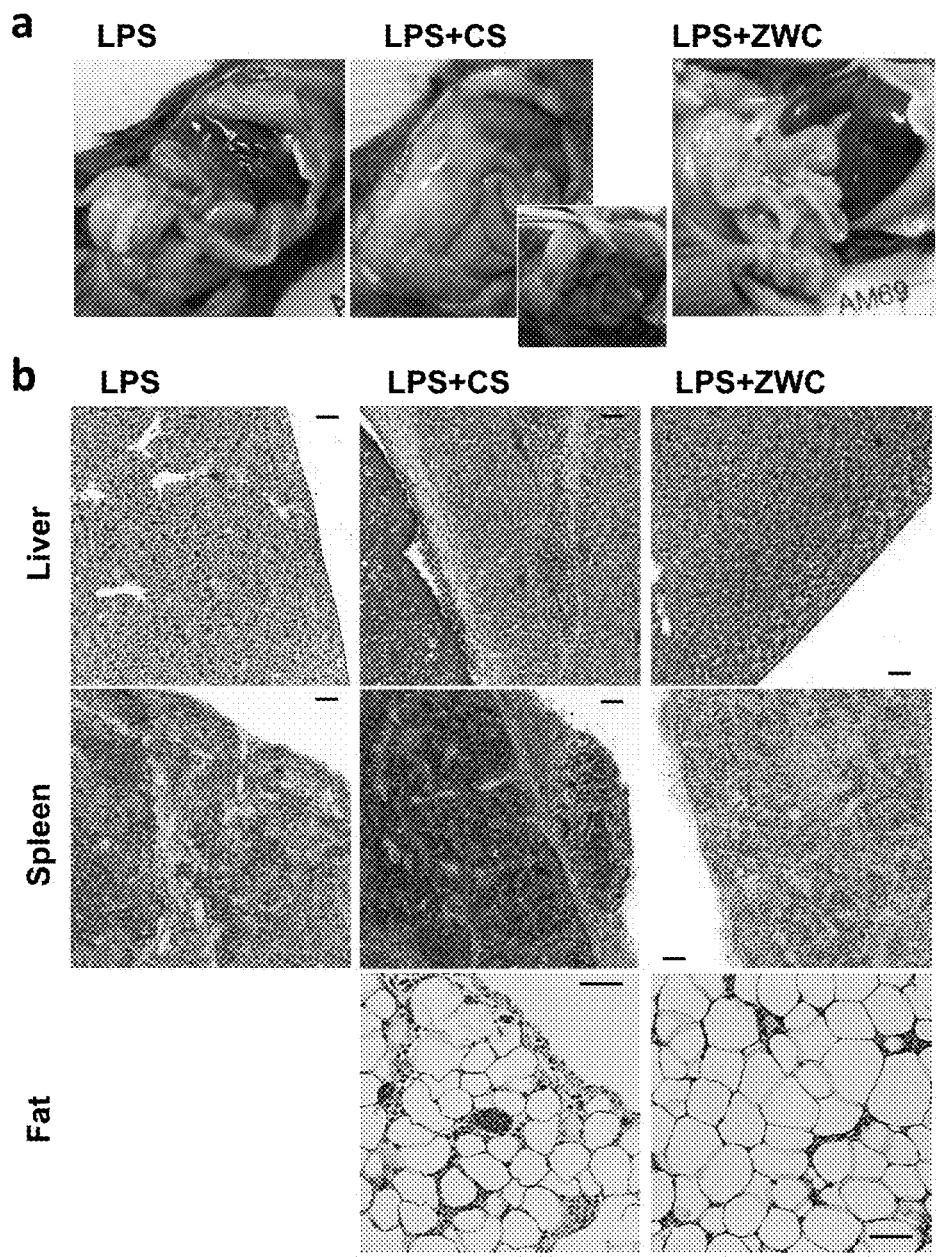
FIG. 23 shows peritoneal cavities of mice injected with LPS only, LPS+CS, and LPS+ZWC (A), and hematoxylin and eosin staining of liver, spleen, and fat sections of animals treated with LPS, LPS+CS and LPS+ZWC (B). Scale bar: 50 µm.

Although ZWC and CS appeared similarly effective in attenuating the effects of LPS in vivo, the tissue responses to these materials were different (FIG. 23A). Similar to the data reported in Example 2 above, none of 9 LPS-challenged animals showed noticeable abnormalities or adhesions upon necropsy. Liver and spleen appeared grossly normal. In contrast, animals administered with CS (LPS+CS) showed adverse tissue responses to CS. Upon necropsy, 7 out of 10 animals had portions of the abdominal viscera (liver, spleen, intestine, kidney and mesentery) encased in a mass of fibrin with focal areas of hemorrhage. In all animals examined histologically, the serosal and capsular surfaces of the spleen, the liver, and the intestine were inflamed and contained copious amounts of fibrin, blood, neutrophils admixed with macrophages, and immature granulation tissue (FIG. 23B). Large collections of globular materials, presumably CS residues, were frequently associated with these changes. A similar but less severe reaction was present in the adjacent mesenteric fat. In the most severely affected regions, the inflammation extended into the muscular wall of the intestine or parenchyma of the liver (FIG. 23B). It is noteworthy that the organs connected to CS residues were those first exposed to the IP-injected solution, which indicates that CS precipitated out before it spread throughout the peritoneal cavity. On the other hand, there were no gross signs of adhesions or inflammation in any of the 9 ZWC-treated animals (LPS+ZWC). The absence of residual materials in the peritoneal cavities of the animals treated with ZWC suggests that the IP-injected ZWC was systemically absorbed via the peritoneal capillaries. Upon histological observation, only minimal multifocal collections of fibrin were present on the capsular surface of the spleen (FIG. 23B). The benign tissue responses and systemic absorption of ZWC, clearly unlike those for CS, are likely due to ZWC's water solubility at neutral pH, which makes it desirable for systemic administration. This result is consistent with previous observation of ZWC in healthy animals [3].

C. Mechanisms of ZWC Action Against LPS

Figure 24:
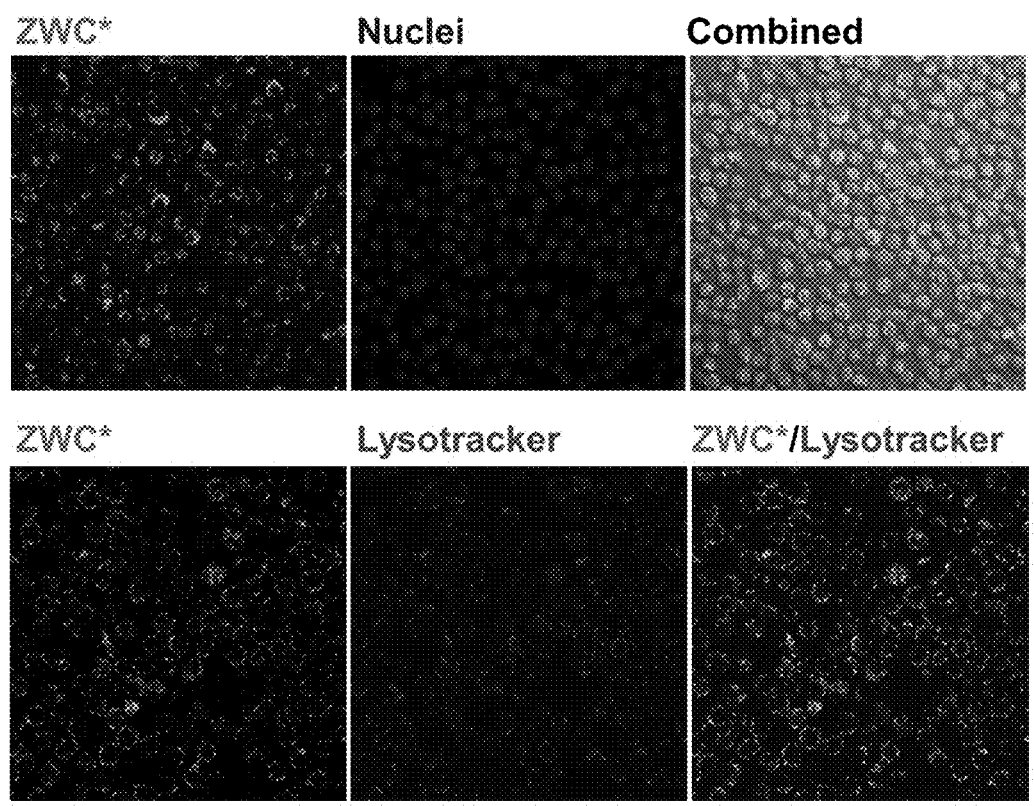
FIG. 24 shows confocal microscopy of PMJ2-PC mouse peritoneal macrophages treated with 0.6 mg/mL fluorescently labeled ZWC (ZWC*) for 3 h (A, C, D & F). Cell nuclei were stained with Hoechst (B & C) prior to imaging. For lysosome staining, macrophages were first incubated with ZWC* and further incubated with 100 nM LysoTracker Red for 30 min (E & F).

While the in vivo results in LPS-challenged animals show promise for ZWC as a systemic treatment of sepsis, its mechanism of action remains unclear. Previous work attributed the anti-inflammatory effect of ZWC in the LPS-challenged macrophages to the extracellular interaction of LPS with ZWC [3]. On the other hand, it was also observed that ZWC entered macrophages and spread in the cytoplasm in 30 min, some co-localizing with lysosomes (FIG. 24). Therefore, an effect of ZWC on macrophages themselves could not be excluded. A series of experiments were performed to investigate extracellular and intracellular effects of ZWC on LPS.

D. Evidence for Extracellular LPS-ZWC Interaction

Figure 25:
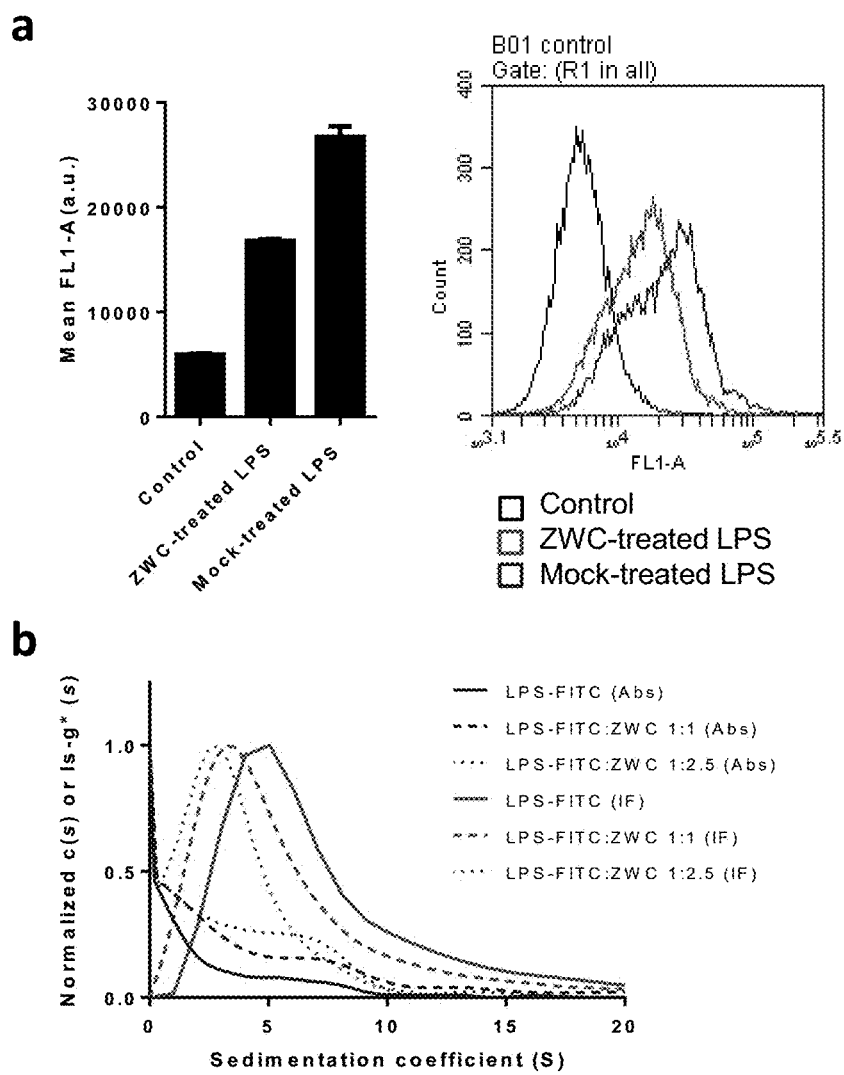
FIG. 25 shows (C) flow cytometry of PMJ2-PC mouse peritoneal macrophages treated with LPS-FITC. Gray (left peak): a control group with no treatment; red (middle peak): a group receiving LPS-FITC pre-incubated with ZWC, precipitated at pH 4.8, centrifuged, and collected in the supernatant; blue (right peak): a group receiving mock-treated LPS-FITC. The graph on the left side (A) shows averages and standard deviations of 3 measurements. All samples show significant difference from each other (Tukey test: $p<0.05$). The plot on the right side shows a representative histogram. (B) Ls-g*(s) distribution of ZWC and LPS-FITC complexes. The interference (IF) signal distribution is attributable to both ZWC and LPS-FITC. Absorbance (Abs) signal at 495 nm confirmed the presence of LPS-FITC in the dominant species.

First, to confirm that ZWC directly interacts with LPS, fluorescently labeled LPS (LPS-FITC conjugate) was incubated with ZWC for 1 h. At the end of the incubation, ZWC was removed by precipitation at pH 4.8 (close to the pI value of ZWC), and the supernatant was incubated with PMJ2-PC mouse peritoneal macrophages. As shown in FIG. 25A, these macrophages displayed lower fluorescence intensity than those incubated with mock-treated LPS-FITC (treated in the same way without ZWC: reduction of pH, centrifugation, and collection of supernatant), indicating that there was less LPS-FITC in the supernatant. This suggests that LPS-FITC was removed together with ZWC, due to a direct interaction between ZWC and LPS-FITC.

Sedimentation coefficients (S) of LPS, ZWC, and LPS-ZWC mixtures, estimated by analytical ultracentrifugation (AUC), provided additional evidence for such an interaction. Here, LPS at a fixed concentration of 0.25 mg/mL was titrated with ZWC at increasing concentrations (0.25-1.25 mg/mL) and subjected to AUC. As shown in Table 5, the LPS-ZWC complex showed much lower sedimentation coefficients than that of LPS with the increase of ZWC concentration in the mixture, approaching the values of ZWC alone.

TABLE 5

Sedimentation coefficients of LPS:ZWC mixtures

| Sample | LPS (mg/mL) | ZWC (mg/mL) | Sedimentation coefficient (S) |
|---|---|---|---|
| LPS | 0.25 | 0 | 3.3, 15, 46 |
| ZWC | 0 | 0.25 | 2.1 |
| ZWC | 0 | 0.625 | 2 |
| ZWC | 0 | 1.25 | 2 |
| LPS:ZWC (1:1) | 0.25 | 0.25 | 2.1 |
| LPS:ZWC (1:2.5) | 0.25 | 0.625 | 2 |
| LPS:ZWC (1:5) | 0.25 | 1.25 | 2 |
| LPS-FITC | 0.25 | 0 | 7.8 |
| LPS-FITC:ZWC (1:1) | 0.25 | 0.25 | 6 |
| LPS-FITC:ZWC (1:2.5) | 0.25 | 0.625 | 3.6 |

LPS, ZWC, and LPS:ZWC mixtures were spun at 201,600 ref, and LPS-FITC and LPS-FITC:ZWC mixtures were at 32,256 ref.

In order to confirm that the peaks in the 1 s-g* distributions of LPS-ZWC mixtures contained LPS, LPS was replaced with LPS-FITC and the sedimenting boundary at 495 nm and the interference were monitored simultaneously. The 1 s-g* distribution indicated that LPS-FITC was present in the dominant species, with sedimentation coefficients of 7.8, 6, and 3.6 S according to the increase of ZWC concentration (FIG. 25B; Table 5). This suggests that LPS, which tends to form multimeric self-aggregates at a concentration above the critical value (13 µg/mL [5]), disaggregated in the presence of ZWC and underwent complexation/co-sedimentation with it. A similar observation was made with LPS-CS complexes by Yermak et al [6].

E. Nature of Extracellular LPS-ZWC Interaction

Although the results of flow cytometry and AUC suggest that ZWC directly interact with LPS, this interaction may not be explained by the main mechanisms by which conventional LPS antagonists (including CS) inactivate LPS. Electrostatic or hydrophobic interactions with LPS are not likely because ZWC is hydrophilic, anionic at neutral pH, and active in a cell culture medium with a physiological ionic strength. To prove this, surface plasmon resonance (SPR) was performed with ZWC and an L1 chip (GE Healthcare Life Sciences, Piscataway, N.J., USA), which had a surface composed of carboxymethylated dextran covalently conjugated with lipophilic groups. Due to the negative charge of carboxymethylated dextran and hydrophobicity of lipophilic groups, the L1 chip served as an LPS-like platform to test the molecular binding of ZWC via electrostatic and hydrophobic interactions. According to the sensorgram, ZWC had little interaction with the L1 chip irrespective of the concentration, while a positive control (1,2-dimyristoyl-sn-glycero-3-phosphoethanolamine-N-[methoxy(polyethylene glycol)-550], $PEG_{550}$-PE) flowed at the same rate and time showed significant binding to the chip. Having excluded electrostatic or hydrophobic interactions, the most likely mechanism of the ZWC-LPS interaction is the hydrogen bond between —$NH_2$ and —NH—(C=O)—$CH_2$—$CH_2$—(C=O)—OH) groups of ZWC and the lipid A phosphates [1]. It is possible that ZWC is a more robust former of the hydrogen bond than CS, since each succinylation brings two more H-bond acceptor/donors (NH—H vs. NH—(C=O)—$CH_2$—$CH_2$—(C=O)—OH).

F. ZWC Effects on Macrophage Activation

Macrophages are the main effectors of innate immunity, responsible for the initial pro-inflammatory phase of sepsis upon systemic exposure to LPS [7,8]. Given the evidence of ZWC entry into macrophages (FIG. 24), it was suspected that ZWC may have direct effects on LPS-induced intracellular signaling in macrophages. This involves LPS binding to a receptor complex composed of CD14, toll-like receptor 4 (TLR4), and MD2, which triggers signal propagation via the IκB kinase (IKK) and mitogen activated protein kinase (MAPK) pathways, leading to activation and nuclear localization of NF-κB and AP-1 and production of pro-inflammatory cytokines [9,10]. Previous studies have shown that pre-treatment with CS oligosaccharides interferes with MAPK signaling in endothelial cells [11] and RAW264.7 macrophages [12], thereby inhibiting LPS-induced IL-6 production in those cells. A similar result was obtained with the RAW264.7 macrophages pre-treated with another water-soluble derivative of CS and then challenged with an allergen [13]. Opinions on how the CS derivatives suppress the LPS-initiated signaling events vary. While Wang et al. proposed that the CS effect was restricted to intracellular signaling [13], Du et al. demonstrated that CS oligosaccharides inhibited LPS binding to a TLR4/MD-2 receptor complex of RAW264.7 macrophages, thereby attenuating subsequent signaling pathways [14]. As a derivative of CS, ZWC may have a similar effect on LPS-macrophage binding and/or intracellular signaling; therefore, its effect was tested on both.

To investigate the ability of ZWC to interfere with LPS binding to macrophages and subsequent internalization, PMJ2-PC mouse peritoneal macrophages were incubated with LPS-FITC simultaneously with ZWC or after pre-treatment with ZWC. Simultaneous incubation would mainly probe whether LPS-binding to macrophages is inhibited due to the LPS-ZWC complexation shown in FIG. 25, whereas pre-treatment would determine whether ZWC competes with LPS for the same receptor. Flow cytometry found little difference in the FITC level in macrophages treated with LPS-FITC, whether they were treated with LPS-FITC alone, LPS-FITC and ZWC simultaneously, or pre-treated with ZWC prior to LPS-FITC addition (data not shown). This indicates that neither the formation of LPS-ZWC complex nor ZWC itself interferes with the LPS binding to macrophages.

Figure 26:
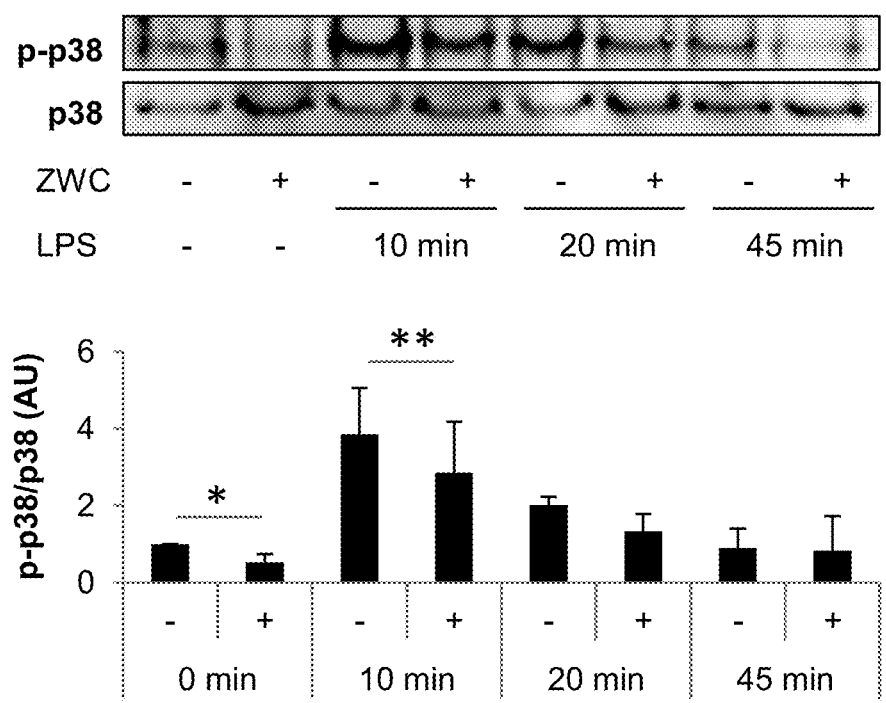
FIG. 26 shows the inhibitory effects of ZWC on LPS-induced phosphorylation of p38 in macrophages. PMJ2-PC mouse peritoneal macrophages were incubated with or without 2 mg/mL of ZWC overnight and challenged with 1 µg/mL of LPS for 10, 20, or 45 min after removing excess ZWC. Western blotting (A) was performed with macrophage cell lysates. The bar graph (B) indicates the band intensity normalized by the intensity of total p38 using ImageJ. Data are expressed as averages and standard deviations of 3 independently and identically performed experiments. *: $p<0.05$, **: $p<0.01$ by one-tailed paired t-test.

To investigate the effect of intracellular ZWC on LPS-induced signaling, the phosphorylation of p38, a prominent member of the MAPK family, was examined in macrophages treated with LPS and/or ZWC. To focus on the intracellular effect of ZWC, an LPS challenge was performed on macrophages pre-treated with ZWC (i.e., macrophages that had internalized ZWC) in the absence of excess extracellular ZWC. As shown in FIG. 26, the phospho-p38 (p-p38) level in LPS-challenged macrophages increased at 10 min and returned to the basal level at 45 min, consistent with the literature [11]; meanwhile, the ZWC-pre-treated macrophages showed a significantly reduced levels of p-p38 at 10 min, suggesting inhibitory effect of ZWC on LPS-initiated signaling pathways.

In summary, these results demonstrate that ZWC, a partially succinylated CS derivative, provided a protective effect in a mouse model of LPS-induced shock when given simultaneously with or prior to the LPS challenge. Due to its water solubility at physiological pH, the IP-injected ZWC was readily absorbed with no local residues or adverse tissue reactions at the injection site, unlike the parent CS. ZWC appeared to protect macrophages from the LPS challenge by forming a complex with LPS, thus attenuating pro-inflammatory signaling pathways. Taken together, these findings suggest that ZWC may have utility as a systemic anti-LPS agent.

\* \* \*

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES CITED

1. David, S. A. Towards a rational development of anti-endotoxin agents: novel approaches to sequestration of bacterial endotoxins with small molecules. *J. Mol. Recognit.* 14, 370-387 (2001).
2. Xu, P., Bajaj, G., Shugg, T., Van Alstine, W. G. & Yeo, Y. Zwitterionic chitosan derivatives for pH-sensitive stealth coating. *Biomacromolecules* 11, 2352-2358 (2010).
3. Bajaj, G., Van Alstine, W. G. & Yeo, Y. Zwitterionic chitosan derivative, a new biocompatible pharmaceutical excipient, prevents endotoxin-mediated cytokine release. *PLoS One* 7, e30899 (2012).
4. Yuen, P. S. T., Doi, K., Leelahavanichkul, A. & Star, R. A. Animal models of sepsis and sepsis-induced kidney injury. *J. Clin. Invest.* 119, 2868-2878 (2009).
5. Yu, L., Tan, M., Ho, B., Ding, J. L. & Wohland, T. Determination of critical micelle concentrations and aggregation numbers by fluorescence correlation spectroscopy: Aggregation of a lipopolysaccharide. *Anal. Chim. Acta* 556, 216-225 (2006).
6. Yermak, I. M. et al. Forming and immunological properties of some lipopolysaccharide-chitosan complexes. *Biochimie* 88, 23-30 (2006).
7. Cavaillon, J. M. & Adib-Conquy, M. Monocytes/macrophages and sepsis. *Crit. Care Med.* 33, S506-509 (2005).
8. Cohen, H. B. & Mosser, D. M. Extrinsic and intrinsic control of macrophage inflammatory responses. *J. Leukoc. Biol.* 94, 913-919 (2013).
9. Bode, J. G., Ehlting, C. & Haussinger, D. The macrophage response towards LPS and its control through the p38 (MAPK)-STAT3 axis. *Cell Signal.* 24, 1185-1194 (2012).
10. Lu, Y.-C., Yeh, W.-C. & Ohashi, P. S. LPS/TLR4 signal transduction pathway. *Cytokine* 42, 145-151 (2008).
11. Liu, H. T. et al. Chitosan oligosaccharides inhibit the expression of interleukin-6 in lipopolysaccharide-induced human umbilical vein endothelial cells through p38 and ERK1/2 protein kinases. *Basic Clin. Pharmacol. Toxicol.* 106, 362-371 (2009).
12. Ma, P. et al. Chitosan oligosaccharides inhibit LPS-induced over-expression of IL-6 and TNF-α in RAW264.7 macrophage cells through blockade of mitogen-activated protein kinase (MAPK) and PI3K/Akt signaling pathways. *Carbohydr. Polym.* 84, 1391-1398 (2011).
13. Chen, C. L., Wang, Y. M., Liu, C. F. & Wang, J. Y. The effect of water-soluble chitosan on macrophage activation and the attenuation of mite allergen-induced airway inflammation. *Biomaterials* 29, 2173-2182 (2008).
14. Qiao, Y. et al. Chitosan oligosaccharides suppressant LPS binding to TLR4/MD-2 receptor complex. *Carbohydr. Polym.* 82, 405-411 (2010).
15. Liu, K. C. & Yeo, Y. Zwitterionic chitosan-polyamidoamine dendrimer complex nanoparticles as a pH-sensitive drug carrier. *Mol. Pharmaceut.* 10, 1695-1704 (2013).
16. University of New Hampshire, Biomolecular Interaction Technologies Center, http://sednterp.unh.edu/ (Date of access: 15 Oct. 2015)
17. Schuck, P. Size-distribution analysis of macromolecules by sedimentation velocity ultracentrifugation and lamm equation modeling. *Biophys. J.* 78, 1606-1619 (2000).

What is claimed is:

1. A method of suppressing an inflammatory response in a subject having a bacterial infection, said method comprising administering a therapeutically effective amount of a zwitterionic derivative of chitosan to a subject having a bacterial infection, wherein the inflammatory response is induced in the subject by bacterial lipopolysaccharide (LPS), wherein the zwitterionic derivative of chitosan has an anhydride to amine (An/Am) ratio of 0.3 to 0.7, and wherein the zwitterionic derivative of chitosan was synthesized by partial amidation of a chitosan with succinic anhydride.

2. The method of claim 1, wherein the inflammatory response is a pro-inflammatory response of activated macrophages.

3. The method of claim 1, wherein the inflammatory response is pro-inflammatory cytokine production.

4. The method of claim 3, wherein the cytokine is IL-6.

5. The method of claim 3, wherein the cytokine is TNF-α.

6. A method of suppressing cytokine or chemokine production in a subject having a bacterial infection, said method comprising administering a therapeutically effective amount of a zwitterionic derivative of chitosan to a subject having a bacterial infection, wherein cytokine or chemokine production is induced in the subject by bacterial lipopolysaccharide (LPS), wherein the zwitterionic derivative of chitosan has an anhydride to amine (An/Am) ratio of 0.3 to 0.7, and wherein the zwitterionic derivative of chitosan was synthesized by partial amidation of a chitosan with succinic anhydride.

7. The method of claim 6, wherein the cytokine or chemokine production is by white blood cells.

8. The method of claim 6, wherein the cytokine or chemokine production is by one or more of monocytes, neutrophils, eosinophils, basophils, lymphocytes, macrophages, B cells, T cells, natural killer cells, dendritic cells, and follicular dendritic cells.

9. The method of claim 6, wherein the cytokine production is the production of pro-inflammatory cytokines.

10. The method of claim 6, wherein the cytokine production is IL-6.

11. The method of claim 6, wherein the cytokine production is TNF-α.

12. The method of claim 6, wherein the cytokine production is Macrophage Inflammatory Protein 2 (MIP-2) production.

13. The method of claim 9, wherein the pro-inflammatory cytokines are one or more of interleukin-1 β(IL-1β), interleukin-6 (IL-6), interleukin-12(IL-12), interferon-γ(IFN-γ), and tumor necrosis factor alpha (TNF-α).

14. A method of suppressing cytokine or chemokine production in a subject having a bacterial infection, said method comprising the step of administering a therapeutically effective amount of a nanoparticle structure to a subject having a bacterial infection, wherein the nanoparticle structure comprises a zwitterionic derivative of chitosan and a dendrimer, wherein the cytokine or chemokine production is induced by lipopolysaccharide (LPS), wherein the zwitterionic derivative of chitosan has an anhydride to amine (An/Am) ratio of 0.3 to 0.7, and wherein the zwitterionic derivative of chitosan was synthesized by partial amidation of a chitosan with succinic anhydride.

15. The method of claim 14, wherein the cytokine or chemokine production is by activated macrophages.

16. The method of claim 14, wherein the chitosan binds directly to the LPS.

17. The method of claim 14, wherein the cytokine is IL-6.

18. The method of claim 14, wherein the cytokine is TNF-α.

19. The method of claim 14, wherein the chemokine is MIP-2.

20. The method of claim 14, wherein the zwitterionic derivative of chitosan has an isoelectric point (pI) between about 4 and about 7.

* * * * *